US011560430B2

(12) United States Patent
Chen et al.

(10) Patent No.: US 11,560,430 B2
(45) Date of Patent: *Jan. 24, 2023

(54) ANTI-PD-1 ANTIBODIES AND USES THEREOF

(71) Applicant: Tayu Huaxia Biotech Medical Group Co., LTD, Beijing (CN)

(72) Inventors: Lieping Chen, Beijing (CN); Liqun Luo, Beijing (CN)

(73) Assignee: Tayu Huaxia Biotech Medical Group Co., LTD, Beijing (CN)

( * ) Notice: Subject to any disclaimer, the term of this patent is extended or adjusted under 35 U.S.C. 154(b) by 597 days.

This patent is subject to a terminal disclaimer.

(21) Appl. No.: 16/543,310

(22) Filed: Aug. 16, 2019

(65) Prior Publication Data

US 2020/0115454 A1 Apr. 16, 2020

Related U.S. Application Data

(63) Continuation of application No. 16/252,418, filed on Jan. 18, 2019, now Pat. No. 10,465,007, which is a continuation of application No. PCT/CN2018/073383, filed on Jan. 19, 2018.

(30) Foreign Application Priority Data

Jan. 20, 2017 (CN) .......................... 201710046148.2

(51) Int. Cl.
*C07K 16/28* (2006.01)
*A61K 39/395* (2006.01)
*A61P 35/00* (2006.01)
*A61P 37/00* (2006.01)
*A61P 31/00* (2006.01)
*A61P 19/02* (2006.01)
*A61P 37/02* (2006.01)
*C12N 15/63* (2006.01)
*C12N 15/85* (2006.01)
*A61K 39/00* (2006.01)

(52) U.S. Cl.
CPC .......... *C07K 16/2827* (2013.01); *A61P 19/02* (2018.01); *A61P 31/00* (2018.01); *A61P 35/00* (2018.01); *A61P 37/00* (2018.01); *A61P 37/02* (2018.01); *C07K 16/2818* (2013.01); *C12N 15/63* (2013.01); *C12N 15/85* (2013.01); *A61K 2039/505* (2013.01); *C07K 2317/21* (2013.01); *C07K 2317/24* (2013.01); *C07K 2317/33* (2013.01); *C07K 2317/52* (2013.01); *C07K 2317/565* (2013.01); *C07K 2317/73* (2013.01); *C07K 2317/76* (2013.01); *C07K 2317/92* (2013.01); *C12N 2015/8518* (2013.01)

(58) Field of Classification Search
None
See application file for complete search history.

(56) References Cited

U.S. PATENT DOCUMENTS

| | | |
|---|---|---|
| 4,444,887 A | 4/1984 | Hoffmann |
| 4,694,778 A | 9/1987 | Learn |
| 4,716,111 A | 12/1987 | Osband |
| 4,816,397 A | 3/1989 | Boss |
| 4,816,567 A | 3/1989 | Cabilly |
| 4,946,778 A | 8/1990 | Ladner et al. |
| 4,980,286 A | 12/1990 | Morgan |
| 5,225,539 A | 7/1993 | Winter |
| 5,258,498 A | 11/1993 | Huston |
| 5,413,923 A | 5/1995 | Kucherlapati |
| 5,530,101 A | 6/1996 | Queen et al. |
| 5,545,806 A | 8/1996 | Lonberg |
| 5,565,332 A | 10/1996 | Hoogenboom |
| 5,569,825 A | 10/1996 | Lonberg |
| 5,585,089 A | 12/1996 | Queen et al. |
| 5,625,126 A | 4/1997 | Lonberg |
| 5,633,425 A | 5/1997 | Lonberg |
| 5,658,570 A | 8/1997 | Newman |
| 5,661,016 A | 8/1997 | Lonberg |
| 5,693,761 A | 12/1997 | Queen et al. |
| 5,693,762 A | 12/1997 | Queen et al. |
| 5,693,780 A | 12/1997 | Newman |
| 5,756,096 A | 5/1998 | Newman |
| 5,807,715 A | 9/1998 | Morrison |
| 5,814,318 A | 9/1998 | Lonberg |
| 5,892,019 A | 4/1999 | Schlom et al. |
| 5,939,598 A | 8/1999 | Kucherlapati |
| 6,150,584 A | 11/2000 | Kucherlapati |
| 6,190,370 B1 | 2/2001 | Tsui |
| 6,420,140 B1 | 7/2002 | Hori |
| 6,458,592 B1 | 10/2002 | Jakobovits |
| 8,735,553 B1 | 5/2014 | Li et al. |
| 10,465,007 B2 * | 11/2019 | Chen ..................... C12N 15/85 |

(Continued)

FOREIGN PATENT DOCUMENTS

| | | |
|---|---|---|
| CN | 102264762 A | 11/2011 |
| CN | 104250302 A | 12/2014 |

(Continued)

OTHER PUBLICATIONS

D'Angelo et al. (2018) Frontiers in Immunology 9: 395; p. 1-13.*

(Continued)

*Primary Examiner* — Ilia I Ouspenski

(74) *Attorney, Agent, or Firm* — Morrison & Foerster LLP

(57) ABSTRACT

Provided are anti-PD-1 antibodies or fragments thereof. In various example, the antibodies or fragments thereof includes a heavy chain variable region comprising heavy chain complementarity determining regions HCDR1, HCDR2, and HCDR3, and a light chain variable region comprising light chain complementarity determining regions LCDR1, LCDR2, and LCDR3. Methods of using the antibodies or fragments thereof for treating and diagnosing diseases such as cancer, infection or immune disorders are also provided.

17 Claims, 14 Drawing Sheets

Specification includes a Sequence Listing.

(56) References Cited

U.S. PATENT DOCUMENTS

| | | |
|---|---|---|
| 2006/0270045 A1 | 11/2006 | Cregg |
| 2015/0203579 A1 | 7/2015 | Papadopoulos |
| 2016/0159905 A1 | 6/2016 | Abdiche |
| 2017/0240644 A1 | 8/2017 | Zhou |
| 2018/0051085 A1 | 2/2018 | Chang et al. |
| 2019/0023782 A1 | 1/2019 | Chen |
| 2019/0127478 A1 | 5/2019 | Ekimova |
| 2019/0144543 A1 | 5/2019 | Chen |
| 2021/0261665 A1* | 8/2021 | Chen ............... A61P 37/00 |

FOREIGN PATENT DOCUMENTS

| | | |
|---|---|---|
| CN | 104479020 A | 4/2015 |
| CN | 104945508 A | 9/2015 |
| CN | 105026428 A | 11/2015 |
| CN | 105061597 A | 11/2015 |
| CN | 105175544 A | 12/2015 |
| CN | 105566496 A | 5/2016 |
| CN | 106008714 A | 10/2016 |
| CN | 107922494 A | 4/2018 |
| CN | 108203464 A | 6/2018 |
| EP | 0239400 B1 | 8/1994 |
| EP | 0592106 B1 | 11/2004 |
| EP | 0519596 B1 | 2/2005 |
| EP | 3081576 A1 | 10/2016 |
| EP | 3486257 A1 | 5/2019 |
| WO | 198704462 A1 | 7/1987 |
| WO | WO199109967 A1 | 7/1991 |
| WO | WO199110741 A1 | 7/1991 |
| WO | WO199633735 A1 | 10/1996 |
| WO | WO199634096 A1 | 10/1996 |
| WO | WO199816654 A1 | 4/1998 |
| WO | WO199824893 A2 | 6/1998 |
| WO | WO199824893 A3 | 8/1998 |
| WO | WO199846645 A2 | 10/1998 |
| WO | WO199850433 A2 | 11/1998 |
| WO | WO199852976 A1 | 11/1998 |
| WO | WO199850433 A3 | 2/1999 |
| WO | WO199846645 A3 | 4/1999 |
| WO | WO200034317 A2 | 6/2000 |
| WO | WO200034317 A3 | 8/2000 |
| WO | WO2008156712 A1 | 12/2008 |
| WO | 2010029435 A1 | 3/2010 |
| WO | WO2010036959 A2 | 4/2010 |
| WO | WO2010036959 A3 | 9/2010 |
| WO | 2014179664 A2 | 11/2014 |
| WO | WO2014206107 A1 | 12/2014 |
| WO | 2014179664 A3 | 2/2015 |
| WO | WO2015085847 A1 | 6/2015 |
| WO | WO2015112900 A1 | 7/2015 |
| WO | 2015119930 A1 | 8/2015 |
| WO | 2016014688 A2 | 1/2016 |
| WO | 2016014688 A3 | 3/2016 |
| WO | 2016089873 A1 | 6/2016 |
| WO | WO2016197497 A1 | 12/2016 |
| WO | 2017016497 A1 | 2/2017 |
| WO | 2017019846 A1 | 2/2017 |
| WO | 2017024465 A1 | 2/2017 |
| WO | 2017055547 A1 | 4/2017 |
| WO | 2017058115 A1 | 4/2017 |
| WO | WO2017201766 A1 | 11/2017 |
| WO | 2018013017 A1 | 1/2018 |
| WO | 2018053106 A1 | 3/2018 |
| WO | WO2018133842 A1 | 7/2018 |
| WO | 2020015722 A1 | 1/2020 |

OTHER PUBLICATIONS

Chen et al. (2015) J Clin Invest. 125(9): 3384-3391.*
Arnon, R. et al. (1985). "Monoclonal Antibodies For Immunotargeting Of Drugs In Cancer Therapy," in Monoclonal Antibodies And Cancer Therapy, Reisfeldet al. (eds.), pp. 243-256.
Bird, R.E. et al. (1988). "Single-Chain Antigen-Binding Proteins," Science 242(4877):423-426.
Buchwald, H. et al. (Oct. 1980). "Long-Term, Continuous Intravenous Heparin Administration By An Implantable Infusion Pump In Ambulatory Patients With Recurrent Venous Thrombosis," Surgery 88:507-516.
Chothia, C. et al. (1998). "Structural Determinants in the Sequences of Immunoglobulin Variable Domain," J. Mol. Biol. 278:457-479.
Chothia, C. et al. (Aug. 20, 1987). "Canonical Structures for the Hypervariable Regions of Immunoglobulins," J. Mol. Biol. 196(4):901-917.
Coligan, J.E. et al. (1991). Current Protocols in Immunology, Coligan et al., Eds., Green Publishing Associates and Wiley-lnterscience, John Wiley and Sons, New York., 26 pages.
Dong, H. et al. (Dec. 1999). "B7-H1, A Third Member Of The B7 Family, Co-Stimulates T-Cell Proliferation and Interleukin-10 Secretion," Nature Med. 5(12):1365-1369.
Dong, H. et al. (2002). "Tumor-Associated B7-HI Promotes T-Cell Apoptosis: A Potential Mechanism Of Immune Evasion," Nature Medicine 8(8):793-800.
During, M.J et al. (Apr. 1989). "Controlled Release Of Dopamine From A Polymeric Brain Implant: In Vivo Characterization," Ann. Neural. 25(4):351-356.
Gillies, S.D. et al. (Dec. 20, 1989). "High-Level Expression Of Chimeric Antibodies Using Adapted cDNA Variable Region Cassettes," J. Immunol. Methods 125(1-2):191-202.
Goodson, J. M. (1984). "Chapter 6: Dental Applications," in Medical Applications of Controlled Release 2:115-138.
Hamers-Casterman, C. et al. (Jun. 3, 1993). "Naturally Occurring Antibodies Devoid Of Light Chains," Nature 363 (6428):446-448.
Hellstrom, K.E. et al. (1987). "Antibodies For Drug Delivery," in Controlled Drug Delivery (2nd Ed.), Robinson et al., (eds.), Marcel Dekker, Inc., pp. 623-653.
Howard III, M.A. et al. (Jul. 1989). "Intracerebral Drug Delivery In Rats With Lesion-Induced Memory Deficits," J. Neurosurg. 71(1):105-112.
Huston, J.R. et al. (Aug. 1988). "Protein engineering of antibody binding sites: recovery of specific activity in an anti-digoxin single-chain Fv analogue produced in *Escherichia coli*," Proc. Natl. Acad. Sci. U.S.A. 85(16)5879-5883.
Huston, J.S. et al. (1991). "Protein Engineering Of Single-Chain Fv Analogs and Fusion Proteins," Methods in Enzymology 203:46-88.
International Search Report and Written Opinion, dated Apr. 13, 2018, for PCT Application No. PCT/CN2018/073383, filed Jan. 19, 2018.
International Search Report, dated Apr. 23, 2018, for PCT Application No. PCT/CN2018/073437, filed Jan. 19, 2018.
Jespers, L.S. et al. (Sep. 12. 1994). "Guiding the Selection of Human Antibodies From Phage Display Repertoires to a Single Epitope of an Antigen," Bio/Technology 72:898-903.
Joliot, A. et al. (Mar. 1991). "Antennapedia Homeobox Peptide Regulates Neural Morphogenesis," Proc. Natl. Acad. Sci. USA 88:1864-1868.
Langer, R. (Sep. 28, 1990). "New Methods Of Drug Delivery," Science 249(4976):1527-1533.
Langer, R. et al. (1983). "Chemical and Physical Structure of Polymers as Carriers for Controlled Release of Bioactive Agents: A Review," Macromol. Sci. Rev. Macromol. Chem. 23:61-126.
Levy, R.J. et al. (Apr. 12, 1985). "Inhibition of Calcification Of Bioprosthetic Heart Valves By Local Controlled-Release Diphosphonate," Science 228(4696):190-192.
Lonberg, N. (1995). "Human Antibodies From Transgenic Mice," Int. Rev. Immunol. 13(1):65-93.
Morrison, S.L. (Sep. 1985). "Transfectomas Provide Novel Chimeric Antibodies," Science 229 (4719):1202-1207.
Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.
Morrison, S.L. et al. (1988). "Genetically Engineered Antibody Molecules," Adv. Immunol. 44:65-92.
Neuberger, M.S. et al. (Dec. 13, 1984). "Recombinant antibodies processing novel effector functions," Nature 312:604-608.

(56) References Cited

OTHER PUBLICATIONS

Newman, R. et al. (Nov. 1992). "'"Primatization" Of Recombinant Antibodies For Immunotherapy Of Human Diseases: A Macaque/Human Chimeric Antibody Against Human CD4," Biotechnology 10(10):1455-1460.
NM-005018.2-Homo Sapiens Programmed Cell Death 1 (PDCD1), mRNA.
Non-Final Office Action, dated May 15, 2019, for U.S. Appl. No. 16/252,418, filed Jan. 18, 2019, 4 pages.
Ol, V.T et al. (1986). "Chimeric Antibodies," Bio Techniques 4:214-219.
Order, S.E. (1985). "Analysis, Results, And Future Prospective Of The Therapeutic Use Of Radiolabeled Antibody In Cancer Therapy", in Monoclonal Antibodies For Cancer Detection And Therapy, Baldwin et al. (eds.). Academic Press pp. 303-316.
Padlan, E.A. (Feb. 1994). "Anatomy Of The Antibody Molecule," Molec. Immun. 31(3):169-217.
Padlan, E.D. (1991). "A Possible Procedure for Reducing the Immunogenicity of Antibody Variable Domains While Preserving Their Ligand-Binding Properties," Mol. Immunol. 28(4/5):489-498.
Riechmann, L. et al. (1988). "Reshaping Human Antibodies For Therapy," Nature 332:323-329.
Roguska, M.A. et al. (Feb. 1, 1994). "Humanization Of Murine Monoclonal Antibodies Through Variable Domain Resurfacing," Proc. Natl. Acad. Sci. USA 91(3):969-973.
Roux, K.H. et al (1998). "Comparisons of the Ability of Human IgG3 Hinge Mutants, IgM, IgE, and IgA2, to Form Small Immune Complexes: A Role for Flexibility and Geometry," J. Immunol. 161:4083-4090.
Saudek, CD. et al. (Aug. 31, 1989). "A Preliminary Trial Of The Programmable Implantable Medication System For Insulin Delivery," N. Engl. J. Med. 321(9):574-579.
Sefton, M.V. (1989). "Implantable Pumps," in CRC Crit. Ref. Biomed. Eng. 14(3):201-240.
Shu, L. et al. (Sep. 1, 1993). "Secretion Of A Single-Gene-Encoded Immunoglobulin From Myeloma Cells," Proc. Natl. Acad. Sci. USA 90(17)7995-7999.
Skerra, A. et al. (May 20, 1988). "Assembly Of A Functional Immunoglobulin Fv Fragment In *Escherichia coli*," Science 240(4855):1038-1041.
Studnicka, G.M. et al. (Jun. 1994). "Human-Engineered Monoclonal Antibodies Retain Full Specific Binding Activity By Preserving Non-CDR complementarity-Modulating Residues," Protein Engineering 7(6):805-814.
Takeda, S. et al. (Apr. 4-10, 1985). "Construction Of Chimaeric Processed Immunoglobulin Genes Containing Mouse Variable And Human Constant Region Sequences," Nature 314(6010):452-454.
Thorpe, (1985). "Antibody Carriers Of Cytotoxic Agents In Cancer Therapy: A Review," in Monoclonal Antibodies '84 Biological And Clinical Applications, Pinchera et al. (eds.), pp. 475-506.
Thorpe, P.E. et al. (1982). "The Preparation And Cytotoxic Properties Of Antibody-Toxin Conjugates," Immunol. Rev. 62:119-158.
Treat et al. (1989)."Liposome Encapsulated Doxrubicin Preliminary Results Of Phase I and Phase II Trials," in Liposomes in the Therapy of Infectious Disease and Cancer, Lopez-Berestein and Fidler (eds.), Liss, New York, pp. 353-365.
Verhoeyen, M. et al. (Mar. 25, 1988). "Reshaping Human Antibodies: Grafting an Antilysozyme Activity," Science 239:1534-1536.
Ward, E.S. et al. (Oct. 12, 1989). "Binding Activities Of A Repertoire Of Single Immunoglobulin Variable Domains Secreted From *Escherichia coli*," Nature 334:544-554.
Wu, G.Y. et al. (1987). "Receptor-mediated in Vitro Gene Transformation by a Soluble DNA Carrier System," J. Biol. Chem. 262(10):4429-4432.
Yao, S. et al. (May 27, 2011). "B7-H2 Is a Costimulatory Ligand for CD28 in Human," Immunity. 34(5):729-740.
Endo, Y. et al. (2003). "High-Throughput, Genome-Scale Protein Production Method Based On The Wheat Germ Cell-Free Expression System," Biotechnol. Adv. 21:695-713.
Fumiya, H. et al. (Feb. 1, 2005). "Blockade of B7-H1 and PD-1 By Monoclonal Antibodies Potentiates Cancer Therapeutic Immunity," Cancer Research 65(3):1089-1096.
International Preliminary Report on Patentability, dated Jan. 19, 2021, for PCT Application No. PCT/CN2019/096679, filed Jul. 19, 2019, 7 pages.
International Preliminary Report on Patentability, dated Jul. 23, 2019, for PCT Application No. PCT/CN2018/073383, filed Jan. 19, 2018, 6 pages.
International Preliminary Report On Patentability, dated Jul. 23, 2019, for PCT Application No. PCT/CN2018/073437, filed Jan. 19, 2018, 6 pages.
International Search Report and Written, dated Oct. 25, 2019, for PCT Application No. PCT/CN2019/096679, filed Jul. 19, 2019, 12 pages.
Lefranc, M.-P. et al., (2015, e-pub. Nov. 5, 2014). "IMGT®, The International ImMunoGeneTics Information System® 25 Years On," Nucleic Acids Res, 43:D413-0422.
Remington's Pharmaceutical Sciences. (1980). 16th edition, Osol, A. Ed, pp. 1-2, (Table of Contents Only).
Running Deer, J. et al. (May-Jun. 2004, e-pub. Mar. 10, 2004). "High-Level Expression Of Proteins In Mammalian Cells Using Transcription Regulatory Sequences From The Chinese Hamster EF-1Alpha Gene," Biotechnol. Prog. 20(3):880-889.
Sambrook, J. et al. (2001). Molecular Cloning: A Laboratory Manual Cold Spring Harbor Laboratory Press, Cold Spring Harbor,N. Y., 3rd ed., 1 page, Table of Contents.
Sitaraman, K. et al. (2009). "High-Throughput Protein Expression Using Cell-Free System," Methods Mol. Biol. 498:229-244.
Spirin, A.S. (Oct. 2004). "High-Throughput Cell-Free Systems for Synthesis of Functionally Active Proteins," Trends Biotechnol. 22(10):538-545.
Schalper, K.A. et al. (Jan. 1, 2014). "Programmed Deth-1/programmed Detha-1 Ligand Axis as a Therapeutic Target in Oncology: Current Insights," Journal of Receptor, Ligand and Channel Research 8:1-7.

\* cited by examiner 1. 5'RASE a-hPD-1(TY101) VL
2. 5'RASE a-hPD-1(TY101) VH
3. 5'RASE TFR Primer (+ Ctrl)
4. Universal Primer A Mix (UPM) only (- Ctrl)
5. Gene-specific primers (GSP) VL only (- Ctrl)
6. Gene-specific primers (GSP) VH only (- Ctrl)

A. Binding activity of rDNA antibody

B. Blocking ability of rDNA antibody

ANTI-PD-1 ANTIBODIES AND USES THEREOF

CROSS REFERENCE TO RELATED APPLICATIONS

This application is a continuation application of U.S. patent application Ser. No. 16/252,418, filed Jan. 18, 2019, which is a continuation application of International Application No. PCT/CN2018/073383, filed internationally on Jan. 19, 2018, which claims the benefit of Chinese Application No. 201710046148.2, filed Jan. 20, 2017.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 792572000601SEQLIST.txt, date recorded: Aug. 13, 2019, size: 34 KB).

BACKGROUND

The cDNA of programmed cell death 1 (PD-1) was isolated in 1992 from a murine T cell hybridoma and a hematopoietic progenitor cell line undergoing apoptosis. Genetic ablation studies showed that deficiencies in PD-1 resulted in different autoimmune phenotypes in various mouse strains. PD-1-deficient allogeneic T cells with transgenic T cell receptors (TCRs) exhibited augmented responses to alloantigens, indicating that the PD-1 on T cells plays a negative regulatory role in response to antigen.

Several studies contributed to the discovery of the molecules that interact with PD-1. In 1999, the B7 homolog one (B7-H1, also called programmed death-ligand 1 [PD-L1]) was identified independently from PD-1 using molecular cloning and human expressed-sequence tag database searches based on its homology with B7 family molecules and it was shown that B7-H1 acts as an inhibitor of human T cell responses in vitro. These two independent lines of studies merged one year later when Freeman, Wood and Honjo's laboratories showed that B7-H1 (hereafter referred to as PD-L1) is a binding and functional partner of PD-1. Next it was determined that PD-L1-deficient mice (PD-L1 KO mice) were prone to the induction of autoimmune diseases although this strain of mice did not spontaneously develop such diseases. It becomes clear later that the PD-L1/PD-1 interaction plays a dominant role in the suppression of T cell responses in vivo, especially in the tumor microenvironment.

The instant initial study showed that tumor-associated PD-L1 facilitates apoptosis of activated T cells (Dong H. et al. Tumor-associated B7-H1 promotes T-cell apoptosis: a potential mechanism of immune evasion. *Nature medicine.* 2002; 8(8):793-800) and also stimulates IL-10 production in human peripheral blood T cells (Dong H, et al., B7-H1, a third member of the B7 family, co-stimulates T-cell proliferation and interleukin-10 secretion. *Nature medicine.* 1999; 5(12):1365-9) to mediate immune suppression. It is now known that the effects of PD-L1 on immune suppression are far more complicated. In addition to T cell apoptosis and IL-10 induction, PD-L1 can also induce T cell dysfunction through a variety of mechanisms. The PD pathway was also shown to promote T cell anergy in vitro and in vivo.

Recently, the FDA approved two PD-1 mAbs to treat human cancers, one from Bristol-Myers Squibb (Opdivo, nivolumab, MDX-1106, BMS-936558, ONO-4538) and the other from Merck (Keytruda, pembrolizumab, lambrolizumab, MK-3475). Additionally, multiple mAbs to either PD-1 or PD-L1 are under active development in hundreds of clinical trials involving thousands of patients. Thus far, anti-PD therapy generates significant clinical benefits by inducing regression of advanced and metastatic tumors and improved survival. More importantly, anti-PD therapy can have durable effects, tolerable toxicity, and show to be applicable to a broad spectrum of cancer types, especially in solid tumors. These clinical findings further validate the principles of the PD pathway blockade and put anti-PD therapy in a unique category distinct from personized or tumor type-specific therapy. Due to its distinct and non-overlapping mechanism with other cancer therapies, anti-PD therapy is on the way to combine with nearly all cancer treatment methods in an attempt to further amplify therapeutic efficacy. In addition to the combination with various cancer immunotherapy approaches such as cancer vaccine, costimulation and coinhibition antibody and adoptive cell therapy, various clinical trials are also initiated to combine anti-PD therapy with chemotherapy, radiotherapy and targeted therapy.

Anti-PD therapy has taken center stage in immunotherapies against human cancer, especially for solid tumors. This therapy is distinct from the prior immune therapeutic agents which largely aim to boost systemic immune responses or to generate de novo immunity against cancer; instead, anti-PD therapy modulates immune responses at the tumor site, targets tumor-induced immune defects, and repairs ongoing immune responses. While the clinical success of anti-PD therapy for the treatment of a variety of human cancers has validated this approach, we are still learning from this pathway and the associated immune responses, which will aid in the discovery and design of new clinically applicable approaches in cancer immunotherapy.

SUMMARY

The present disclosure provides anti-PD-1 antibodies that exhibited excellent binding and inhibitory activities on PD-1 proteins. One of the tested ones even showed stronger binding activities than two regulatorily proved anti-PD-1 antibody products.

In accordance with one embodiment of the present disclosure, therefore, provided is an isolated antibody or fragment thereof having specificity to a human programmed cell death protein 1 (PD-1), wherein the antibody or fragment thereof comprises a heavy chain variable region comprising heavy chain complementarity determining regions HCDR1, HCDR2, and HCDR3, and a light chain variable region comprising light chain complementarity determining regions LCDR1, LCDR2, and LCDR3, wherein the HCDR1, HCDR2, HCDR3, LCDR1, LCDR2, and LCDR3 are selected from the group consisting of: (a) HCDR1: GFTFSSYT (SEQ ID NO: 1), HCDR2: ISHGGGDT (SEQ ID NO: 2), HCDR3: ARHSGYERGYYYVMDY (SEQ ID NO: 3), LCDR1: ESVDYYGFSF (SEQ ID NO: 4), LCDR2: AAS (SEQ ID NO: 5), LCDR3: QQSKEVPW (SEQ ID NO: 6); (b) HCDR1: GYTFTSYT (SEQ ID NO: 7), HCDR2: INPTTGYT (SEQ ID NO: 8), HCDR3: ARDDAYYSGY (SEQ ID NO: 9), LCDR1: ENIYSNL (SEQ ID NO: 10), LCDR2: AAK (SEQ ID NO: 11), LCDR3: QHFWGTPWT (SEQ ID NO: 12); and (c) HCDR1: GFAFSSYD (SEQ ID NO: 13), HCDR2: ITIGGGTT (SEQ ID NO: 14), HCDR3: ARHRYDYFAMDN (SEQ ID NO: 15), LCDR1:

ENVDNYGINF (SEQ ID NO: 16), LCDR2: VSS (SEQ ID NO: 17), LCDR3: QQSKDVPW (SEQ ID NO: 18).

In some embodiments, the antibody or fragment of the present disclosure further comprises a heavy chain constant region, a light chain constant region, an Fc region, or the combination thereof. In some embodiments, the light chain constant region is a kappa or lambda chain constant region.

The antibody or fragment thereof of can be an isotype of IgG, IgM, IgA, IgE or IgD, in some embodiments. In some embodiments, the isotype is IgG1, IgG2, IgG3 or IgG4. In some embodiments, the antibody or fragment thereof is a chimeric antibody, a humanized antibody, or a fully human antibody.

In some embodiments, the antibody or fragment thereof comprises a heavy chain variable region comprising the amino acid sequence of SEQ ID NO: 35, SEQ ID NO: 37, SEQ ID NO: 39, or an amino acid sequence having at least 95% sequence identity to SEQ ID NO: 35, SEQ ID NO: 37, or SEQ ID NO: 39. In some embodiments, the antibody or fragment thereof of comprises a light chain variable region comprising the amino acid sequence of SEQ ID NO: 41, SEQ ID NO: 43, SEQ ID NO: 45, or an amino acid sequence having at least 95% sequence identity to SEQ ID NO: 41, SEQ ID NO: 43, or SEQ ID NO: 45.

In another embodiment, the present disclosure provides an isolated antibody or fragment thereof having specificity to a human programmed cell death protein 1 (PD-1), wherein the antibody or fragment thereof comprises a heavy chain variable region comprising heavy chain complementarity determining regions HCDR1, HCDR2, and HCDR3, and a light chain variable region comprising light chain complementarity determining regions LCDR1, LCDR2, and LCDR3, wherein the HCDR1, HCDR2, HCDR3, LCDR1, LCDR2, and LCDR3 are selected from the group consisting of (a) HCDR1: GFTFSSYT (SEQ ID NO: 1), HCDR2: ISHGGGDT (SEQ ID NO: 2), HCDR3: ARHSGYER-GYYYVMDY (SEQ ID NO: 3), LCDR1: ESVDYYGFSF (SEQ ID NO: 4), LCDR2: AAS (SEQ ID NO: 5), LCDR3: QQSKEVPW (SEQ ID NO: 6); (b) HCDR1: GYTFTSYT (SEQ ID NO: 7), HCDR2: INPTTGYT (SEQ ID NO: 8), HCDR3: ARDDAYYSGY (SEQ ID NO: 9), LCDR1: ENIYSNL (SEQ ID NO: 10), LCDR2: AAK (SEQ ID NO: 11), LCDR3: QHFWGTPWT (SEQ ID NO: 12); (c) HCDR1: GFAFSSYD (SEQ ID NO: 13), HCDR2: ITIGGGTT (SEQ ID NO: 14), HCDR3: ARHRYDYFAMDN (SEQ ID NO: 15), LCDR1: ENVDNYGINF (SEQ ID NO: 16), LCDR2: VSS (SEQ ID NO: 17), LCDR3: QQSKDVPW (SEQ ID NO: 18); and (d) HCDR1, HCDR2, HCDR3, LCDR1, LCDR2, and LCDR3 as shown in (a)-(c) but at least one of which includes one, two, or three amino acid addition, deletion, conservative amino acid substitution or the combinations thereof.

In some embodiments, the HCDR1, HCDR2, HCDR3 LCDR1, LCDR2, and LCDR3 are as shown in any one of (a)-(c) but one of which includes a conservative amino acid substitution. In some embodiments, the HCDR1, HCDR2, HCDR3, LCDR1, LCDR2, and LCDR3 are as shown in any one of (a)-(c) but two of which each includes a conservative amino acid substitution. In some embodiments, the HCDR1, HCDR2, HCDR3, LCDR1, LCDR2, and LCDR3 are as shown in any one of (a)-(c) but three of which each includes a conservative amino acid substitution.

Also provided, in one embodiment, is a composition comprising the antibody or fragment thereof of the present disclosure and a pharmaceutically acceptable carrier. Still further provided, in one embodiment, is an isolated cell comprising one or more polynucleotide encoding the antibody or fragment thereof.

Uses and methods are also provided. In one embodiment, provided is a use of the antibody or fragment thereof of the present disclosure for the manufacture of a medicament for the treatment of cancer. The cancer can be selected from the group consisting of bladder cancer, liver cancer, colon cancer, rectal cancer, endometrial cancer, leukemia, lymphoma, pancreatic cancer, small cell lung cancer, non-small cell lung cancer, breast cancer, urethral cancer, head and neck cancer, gastrointestinal cancer, stomach cancer, esophageal cancer, ovarian cancer, renal cancer, melanoma, prostate cancer and thyroid cancer. Also provided is a method of treating cancer in a patient in need thereof, comprising administering to the patient the antibody or fragment thereof the present disclosure.

In another embodiment, the present disclosure provides a method of treating cancer or infection in a patient in need thereof, comprising (a) treating a cell, in vitro, with the antibody or fragment thereof of the present disclosure; and (b) administering the treated cell to the patient. In some embodiments, the cell is a T cell.

In another embodiment, provided is a use of the antibody or fragment thereof of any one of the present disclosure for the manufacture of a medicament for the treatment of an infection. In some embodiments, the infection is viral infection, bacterial infection, fungal infection or infection by a parasite.

In yet another embodiment, provided is a use of the antibody or fragment thereof of the present disclosure for the manufacture of a medicament for the treatment of an immune disorder. In some embodiments, the immune disorder is selected from the group consisting of infection, endotoxic shock associated with infection, arthritis, rheumatoid arthritis, asthma, COPD, pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, arthritis, meningoencephalitis, autoimmune uveitis, immune mediated inflammatory disorders of the central and peripheral nervous system, multiple sclerosis, lupus and Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, pancreatitis, trauma, graft-versus-host disease, transplant rejection, ischaemic diseases, myocardial infarction, atherosclerosis, intravascular coagulation, bone resorption, osteoporosis, osteoarthritis, periodontitis, hypochlorhydia, and infertility related to lack of fetal-maternal tolerance.

DETAILED DESCRIPTION

Definitions

Figure 1:
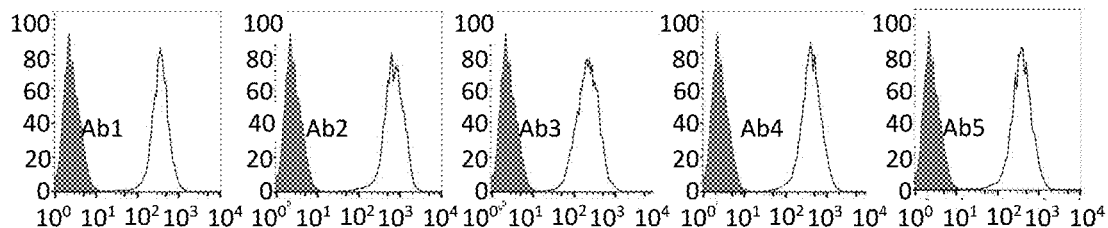
FIG. 1 shows that all five hPD-1 mAb isotypes can bind to hPD-1 with high specificity.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

The term "isolated" as used herein with respect to cells, nucleic acids, such as DNA or RNA, refers to molecules separated from other DNAs or RNAs, respectively, that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to cells or polypeptides which are isolated from other cellular proteins or tissues. Isolated polypeptides is meant to encompass both purified and recombinant polypeptides.

As used herein, the term "recombinant" as it pertains to polypeptides or polynucleotides intends a form of the polypeptide or polynucleotide that does not exist naturally, a non-limiting example of which can be created by combining polynucleotides or polypeptides that would not normally occur together.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Biologically equivalent polynucleotides are those having the above-noted specified percent homology and encoding a polypeptide having the same or similar biological activity.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., salt-bridge) of the reference sequence.

Hybridization reactions can be performed under conditions of different "stringency". In general, a low stringency hybridization reaction is carried out at about 40° C. in about 10× SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching. The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as $F(ab')_2$, $F(ab)_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy ($V_H$) and light chains ($V_L$) of immunoglobulins. In some aspects, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgG_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda (K, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VK) and heavy (VH) chain portions determine antigen recognition and specificity. Conversely, the constant domains of the light chain (CK) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CK domains actually comprise the carboxy-terminus of the heavy and light chain, respectively.

As indicated above, the variable region allows the antibody to selectively recognize and specifically bind epitopes on antigens. That is, the VK domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VK chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Castermanet al., Nature 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see "Sequences of Proteins of Immunological Interest," Kabat, E., et al., U.S. Department of Health and Human Services, (1983); and Chothia and Lesk, J. Mol Biol., 196:901-917 (1987)).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol Biol. 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth in the table below as a comparison. The exact residue numbers which encompass a particular CDR will vary depending on the sequence and size of the CDR. Those skilled in the art can routinely determine which residues comprise a particular CDR given the variable region amino acid sequence of the antibody.

|        | Kabat  | Chothia |
|--------|--------|---------|
| CDR-H1 | 31-35  | 26-32   |
| CDR-H2 | 50-65  | 52-58   |
| CDR-H3 | 95-102 | 95-102  |
| CDR-L1 | 24-34  | 26-32   |
| CDR-L2 | 50-56  | 50-52   |
| CDR-L3 | 89-97  | 91-96   |

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering"

refers to the numbering system set forth by Kabat et al., U.S. Dept. of Health and Human Services, "Sequence of Proteins of Immunological Interest" (1983).

In addition to table above, the Kabat number system describes the CDR regions as follows: CDR-H1 begins at approximately amino acid 31 (i.e., approximately 9 residues after the first cysteine residue), includes approximately 5-7 amino acids, and ends at the next tryptophan residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids; and ends at the sequence W-G-X-G, where X is any amino acid. CDR-L1 begins at approximately residue 24 (i.e., following a cysteine residue); includes approximately 10-17 residues; and ends at the next tryptophan residue. CDR-L2 begins at approximately the sixteenth residue after the end of CDR-L1 and includes approximately 7 residues. CDR-L3 begins at approximately the thirty third residue after the end of CDR-L2 (i.e., following a cysteine residue); includes approximately 7-11 residues and ends at the sequence F or W-G-X-G, where X is any amino acid.

Antibodies disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of ordinary skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an $IgG_1$ molecule and a hinge region derived from an $IgG_3$ molecule. In another example, a heavy chain constant region can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., *J. Immunol* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CK regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g. mouse or primate) and the constant region is human.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Anti-PD-1 Antibodies

The present disclosure provides anti-PD-1 antibodies with high affinity to the human PD-1 protein. The tested antibodies exhibited potent binding and inhibitory activities and are useful for therapeutic and diagnostics uses. Further, one of the humanized antibodies tested (TY101) exhibited significantly higher binding affinities than two FDA approved anti-hPD-1 antibodies.

One embodiment of the present disclosure, therefore, provides an anti-PD-1 antibody or fragment thereof, which antibody or fragment thereof can specifically bind to a human Programmed death 1 (PD-1) protein.

In accordance with one embodiment of the present disclosure, provided is an antibody that includes the heavy chain and light chain variable domains with the CDR regions as one of the CDR groups in Table 1.

TABLE 1

Sequences of the CDR regions

| CDR Groups | Sequences (SEQ ID NO:) |
|---|---|
| CDR group 1 | HCDR1: GFTFSSYT (1) |
| | HCDR2: ISHGGGDT (2) |
| | HCDR3: ARHSGYERGYYYVMDY (3) |
| | LCDR1: ESVDYYGFSF (4) |
| | LCDR2: AAS (5) |
| | LCDR3: QQSKEVPW (6) |

TABLE 1-continued

Sequences of the CDR regions

| CDR Groups | Sequences (SEQ ID NO:) |
|---|---|
| CDR group 2 | HCDR1: GYTFTSYT (7) |
| | HCDR2: INPTTGYT (8) |
| | HCDR3: ARDDAYYSGY (9) |
| | LCDR1: ENIYSNL (10) |
| | LCDR2: AAK (11) |
| | LCDR3: QHFWGTPWT (12) |
| CDR group 3 | HCDR1: GFAFSSYD (13) |
| | HCDR2: ITIGGGTT (14) |
| | HCDR3: ARHRYDYFAMDN (15) |
| | LCDR1: ENVDNYGINF (16) |
| | LCDR2: VSS (17) |
| | LCDR3: QQSKDVPW (18) |

For instance, in one embodiment, provided is an isolated antibody or fragment thereof having specificity to a human programmed cell death protein 1 (PD-1), wherein the antibody or fragment thereof comprises a heavy chain variable region comprising heavy chain complementarity determining regions HCDR1, HCDR2, and HCDR3, and a light chain variable region comprising light chain complementarity determining regions LCDR1, LCDR2, and LCDR3, wherein the HCDR1, HCDR2, HCDR3, LCDR1, LCDR2, and LCDR3 are HCDR1: GFTFSSYT (SEQ ID NO: 1), HCDR2: ISHGGGDT (SEQ ID NO: 2), HCDR3: ARHSGYERGYYYVMDY (SEQ ID NO: 3), LCDR1: ESVDYYGFSF (SEQ ID NO: 4), LCDR2: AAS (SEQ ID NO: 5), LCDR3: QQSKEVPW (SEQ ID NO: 6).

For instance, in one embodiment, provided is an isolated antibody or fragment thereof having specificity to a human programmed cell death protein 1 (PD-1), wherein the antibody or fragment thereof comprises a heavy chain variable region comprising heavy chain complementarity determining regions HCDR1, HCDR2, and HCDR3, and a light chain variable region comprising light chain complementarity determining regions LCDR1, LCDR2, and LCDR3, wherein the HCDR1, HCDR2, HCDR3, LCDR1, LCDR2, and LCDR3 are HCDR1: GYTFTSYT (SEQ ID NO: 7), HCDR2: INPTTGYT (SEQ ID NO: 8), HCDR3: ARDDAYYSGY (SEQ ID NO: 9), LCDR1: ENIYSNL (SEQ ID NO: 10), LCDR2: AAK (SEQ ID NO: 11), LCDR3: QHFWGTPWT (SEQ ID NO: 12).

For instance, in one embodiment, provided is an isolated antibody or fragment thereof having specificity to a human programmed cell death protein 1 (PD-1), wherein the antibody or fragment thereof comprises a heavy chain variable region comprising heavy chain complementarity determining regions HCDR1, HCDR2, and HCDR3, and a light chain variable region comprising light chain complementarity determining regions LCDR1, LCDR2, and LCDR3, wherein the HCDR1, HCDR2, HCDR3, LCDR1, LCDR2, and LCDR3 are HCDR1: GFAFSSYD (SEQ ID NO: 13), HCDR2: ITIGGGTT (SEQ ID NO: 14), HCDR3: ARHRYDYFAMDN (SEQ ID NO: 15), LCDR1: ENVDNYGINF (SEQ ID NO: 16), LCDR2: VSS (SEQ ID NO: 17), LCDR3: QQSKDVPW (SEQ ID NO: 18).

As demonstrated in the experimental examples, the antibodies that contained these CDR regions, whether mouse, humanized or chimeric, had potent PD-1 binding and inhibitory activities. Further computer modeling indicated that certain residues within the CDR can be modified to retain or improve the property of the antibodies. In some embodiments, an anti-PD-1 antibody of the present disclosure includes the VH and VL CDR as listed in Table 1, with one, two or three further modifications. Such modifications can be addition, deletion or substation of amino acids.

In some embodiments, the modification is substitution at no more than one hot spot position from each of the CDRs. In some embodiments, the modification is substitution at one, two or three such hot spot positions. In one embodiment, the modification is substitution at one of the hot spot positions. Such substitutions, in some embodiments, are conservative substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

| Amino Acid Similarity Matrix | | | | | | | | | | | | | | | | | | | |
|---|---|---|---|---|---|---|---|---|---|---|---|---|---|---|---|---|---|---|---|
| | C | G | P | S | A | T | D | E | N | Q | H | K | R | V | M | I | L | F | Y | W |
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −3 | −3 | −4 | −4 | −2 | −4 | 0 | −4 | −5 | −2 | −2 | −1 | −1 | 7 | 10 | |
| F | −4 | −5 | −5 | −3 | −4 | −3 | −6 | −5 | −4 | −5 | −2 | −5 | −4 | −1 | 0 | 1 | 2 | 9 | | |
| L | −6 | −4 | −3 | −3 | −2 | −2 | −4 | −3 | −3 | −2 | −2 | −3 | −3 | 2 | 4 | 2 | 6 | | | |
| I | −2 | −3 | −2 | −1 | −1 | 0 | −2 | −2 | −2 | −2 | −2 | −2 | −2 | 4 | 2 | 5 | | | | |
| M | −5 | −3 | −2 | −2 | −1 | −1 | −3 | −2 | 0 | −1 | −2 | 0 | 0 | 2 | 6 | | | | | |
| V | −2 | −1 | −1 | −1 | 0 | 0 | −2 | −2 | −2 | −2 | −2 | −2 | −2 | 4 | | | | | | |
| R | −4 | −3 | 0 | 0 | −2 | −1 | −1 | −1 | 0 | 1 | 2 | 3 | 6 | | | | | | | |
| K | −5 | −2 | −1 | 0 | −1 | 0 | 0 | 0 | 1 | 1 | 0 | 5 | | | | | | | | |
| H | −3 | −2 | 0 | −1 | −1 | −1 | 1 | 1 | 2 | 3 | 6 | | | | | | | | | |
| Q | −5 | −1 | 0 | −1 | 0 | −1 | 2 | 2 | 1 | 4 | | | | | | | | | | |
| N | −4 | 0 | −1 | 1 | 0 | 0 | 2 | 1 | 2 | | | | | | | | | | | |
| E | −5 | 0 | −1 | 0 | 0 | 0 | 3 | 4 | | | | | | | | | | | | |
| D | −5 | 1 | −1 | 0 | 0 | 0 | 4 | | | | | | | | | | | | | |
| T | −2 | 0 | 0 | 1 | 1 | 3 | | | | | | | | | | | | | | |
| A | −2 | 1 | 1 | 1 | 2 | | | | | | | | | | | | | | | |
| S | 0 | 1 | 1 | 1 | | | | | | | | | | | | | | | | |
| P | −3 | −1 | 6 | | | | | | | | | | | | | | | | | |
| G | −3 | 5 | | | | | | | | | | | | | | | | | | |
| C | 12 | | | | | | | | | | | | | | | | | | | |

| Conservative Amino Acid Substitutions | |
|---|---|
| For Amino Acid | Substitution With |
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-GluGln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

Non-limiting examples of VH are provided in SEQ ID NO: 27, SEQ ID NO: 31, SEQ ID NO: 35, SEQ ID NO: 37, and SEQ ID NO: 39. SEQ ID NO: 27 is a murine VH. SEQ ID NO: 31 is VH of a chimeric antibody, and SEQ ID NO: 35, SEQ ID NO: 37, and SEQ ID NO: 39 are humanized.

Non-limiting examples of VL are provided in SEQ ID NO: 29, SEQ ID NO: 33, SEQ ID NO: 41, SEQ ID NO: 43, and SEQ ID NO: 45. SEQ ID NO: 29 is a murine VL. SEQ ID NO: 33 is VL of a chimeric antibody, and SEQ ID NO: 41, SEQ ID NO: 43, and SEQ ID NO: 45 are humanized.

In some embodiments, the anti-PD-1 antibody of the present disclosure includes a VH of in SEQ ID NO: 27, SEQ ID NO: 31, SEQ ID NO: 35, SEQ ID NO: 37, or SEQ ID NO: 39, a VL of SEQ ID NO: 29, SEQ ID NO: 33, SEQ ID NO: 41, SEQ ID NO: 43, or SEQ ID NO: 45, or their respective biological equivalents. A biological equivalent of a VH or VL is a sequence that includes the designated amino acids while having an overall 80%, 85%, 90%, 95%, 98% or 99% sequence identity. A biological equivalent of SEQ ID NO: 27, for instance, can be a VH that has an overall 80%, 85%, 90%, 95%, 98% or 99% sequence identity to SEQ ID NO: 27 but retains the CDRs.

It will also be understood by one of ordinary skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, or 99% identical to the starting sequence.

In certain embodiments, the antibody comprises an amino acid sequence or one or more moieties not normally associated with an antibody. Exemplary modifications are described in more detail below. For example, an antibody of the disclosure may comprise a flexible linker sequence, or may be modified to add a functional moiety (e.g., PEG, a drug, a toxin, or a label).

Antibodies, variants, or derivatives thereof of the disclosure include derivatives that are modified, i.e., by the covalent attachment of any type of molecule to the antibody such that covalent attachment does not prevent the antibody from binding to the epitope. For example, but not by way of limitation, the antibodies can be modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

In some embodiments, the antibodies may be conjugated to therapeutic agents, prodrugs, peptides, proteins, enzymes, viruses, lipids, biological response modifiers, pharmaceutical agents, or PEG.

The antibodies may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

The antibodies can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

The antibodies can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). Techniques for conjugating various moieties to an antibody are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al., (eds.), Marcel Dekker, Inc., pp. 623-53 (1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", Immunol. Rev. (52:119-58 (1982)).

Bi-Functional Molecules

PD-1 is an immune checkpoint molecule and is also a tumor antigen. As a tumor antigen targeting molecule, an antibody or antigen-binding fragment specific to PD-1 can be combined with a second antigen-binding fragment specific to an immune cell to generate a bispecific antibody.

In some embodiments, the immune cell is selected from the group consisting of a T cell, a B cell, a monocyte, a macrophage, a neutrophil, a dendritic cell, a phagocyte, a natural killer cell, an eosinophil, a basophil, and a mast cell. Molecules on the immune cell which can be targeted include, for example, CD3, CD16, CD19, CD28, and CD64. Other examples include PD-1, CTLA-4, LAG-3 (also known as CD223), CD28, CD122, 4-1BB (also known as CD137), TIM3, OX-40 or OX4OL, CD40 or CD4OL, LIGHT, ICOS/ICOSL, GITR/GITRL, TIGIT, CD27, VISTA, B7H3, B7H4, HEVM or BTLA (also known as CD272), killer-cell immunoglobulin-like receptors (KIRs), and CD47. Specific examples of bispecificity include, without limitation, PD-L1/PD-1, PD-1/LAG3, PD-1/TIGIT, and PD-1/CD47.

As an immune checkpoint inhibitor, an antibody or antigen-binding fragment specific to PD-1 can be combined with a second antigen-binding fragment specific to a tumor antigen to generate a bispecific antibody. A "tumor antigen" is an antigenic substance produced in tumor cells, i.e., it triggers an immune response in the host. Tumor antigens are useful in identifying tumor cells and are potential candidates for use in cancer therapy. Normal proteins in the body are not antigenic. Certain proteins, however, are produced or overexpressed during tumorigenesis and thus appear "foreign" to the body. This may include normal proteins that are well sequestered from the immune system, proteins that are normally produced in extremely small quantities, proteins that are normally produced only in certain stages of development, or proteins whose structure is modified due to mutation.

An abundance of tumor antigens are known in the art and new tumor antigens can be readily identified by screening. Non-limiting examples of tumor antigens include EGFR, Her2, EpCAM, CD20, CD30, CD33, CD47, CD52, CD133, CD73, CEA, gpA33, Mucins, TAG-72, CIX, PSMA, folate-binding protein, GD2, GD3, GM2, VEGF, VEGFR, Integrin, $\alpha V\beta 3$, $\alpha 5\beta 1$, ERBB2, ERBB3, MET, IGF1R, EPHA3, TRAILR1, TRAILR2, RANKL, FAP and Tenascin.

In some aspects, the monovalent unit has specificity to a protein that is overexpressed on a tumor cell as compared to a corresponding non-tumor cell. A "corresponding non-tumor cell" as used here, refers to a non-tumor cell that is of the same cell type as the origin of the tumor cell. It is noted that such proteins are not necessarily different from tumor antigens. Non-limiting examples include carcinoembryonic antigen (CEA), which is overexpressed in most colon, rectum, breast, lung, pancreas and gastrointestinal tract carcinomas; heregulin receptors (HER-2, neuor c-erbB-2), which is frequently overexpressed in breast, ovarian, colon, lung, prostate and cervical cancers; epidermal growth factor receptor (EGFR), which is highly expressed in a range of solid tumors including those of the breast, head and neck, non-small cell lung and prostate; asialoglycoprotein receptor; transferrin receptor; serpin enzyme complex receptor, which is expressed on hepatocytes; fibroblast growth factor receptor (FGFR), which is overexpressed on pancreatic ductal adenocarcinoma cells; vascular endothelial growth factor receptor (VEGFR), for anti-angiogenesis gene therapy; folate receptor, which is selectively overexpressed in 90% of nonmucinous ovarian carcinomas; cell surface glycocalyx; carbohydrate receptors; and polymeric immunoglobulin receptor, which is useful for gene delivery to respiratory epithelial cells and attractive for treatment of lung diseases such as Cystic Fibrosis. Non-limiting examples of bispecificity in this respect include PD-1/EGFR, PD-1/Her2, PD-1/CD33, PD-1/CD133, PD-1/CEA and PD-1NEGF.

Different format of bispecific antibodies are also provided. In some embodiments, each of the anti-PD-1 fragment and the second fragment each is independently selected from a Fab fragment, a single-chain variable fragment (scFv), or a single-domain antibody. In some embodiments, the bispecific antibody further includes a Fc fragment.

Bifunctional molecules that include not just antibody or antigen binding fragment are also provided. As a tumor antigen targeting molecule, an antibody or antigen-binding fragment specific to PD-1, such as those described here, can be combined with an immune cytokine or ligand optionally through a peptide linker. The linked immune cytokines or ligands include, but not limited to, IL-2, IL-3, IL-4, IL-5, IL-6, IL-7, IL-10, IL-12, IL-13, IL-15, GM-CSF, TNF-α, CD4OL, OX4OL, CD27L, CD3OL, 4-1BBL, LIGHT and GITRL. Such bi-functional molecules can combine the immune checkpoint blocking effect with tumor site local immune modulation.

Polynucleotides Encoding the Antibodies and Methods of Preparing the Antibodies

The present disclosure also provides isolated polynucleotides or nucleic acid molecules (e.g., SEQ ID NO: 22, 22, 24, 26, 28, 30, 32, 34, 36, 38, 40, 42, 44 and 46) encoding the antibodies, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

In certain embodiments, the prepared antibodies will not elicit a deleterious immune response in the animal to be treated, e.g., in a human. In one embodiment, antigen-binding polypeptides, variants, or derivatives thereof of the disclosure are modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci. USA* 57:6851-6855 (1984); Morrison et al., *Adv. Immunol.* 44:65-92 (1988); Verhoeyen et al., *Science* 239:1534-1536 (1988); Padlan, *Molec. Immun.* 25:489-498 (1991); Padlan, *Molec. Immun.* 31:169-217 (1994), and U.S. Pat. Nos.: 5,585,089, 5,693, 761, 5,693,762, and 6,190,370, all of which are hereby incorporated by reference in their entirety.

De-immunization can also be used to decrease the immunogenicity of an antibody. As used herein, the term "de-immunization" includes alteration of an antibody to modify T-cell epitopes (see, e.g., International Application Publication Nos.: WO/9852976 A1 and WO/0034317 A2). For example, variable heavy chain and variable light chain sequences from the starting antibody are analyzed and a human T-cell epitope "map" from each V region showing the location of epitopes in relation to complementarity-determining regions (CDRs) and other key residues within the sequence is created. Individual T-cell epitopes from the T-cell epitope map are analyzed in order to identify alternative amino acid substitutions with a low risk of altering activity of the final antibody. A range of alternative variable heavy and variable light sequences are designed comprising combinations of amino acid substitutions and these sequences are subsequently incorporated into a range of binding polypeptides. Typically, between 12 and 24 variant antibodies are generated and tested for binding and/or function. Complete heavy and light chain genes comprising modified variable and human constant regions are then cloned into expression vectors and the subsequent plasmids introduced into cell lines for the production of whole antibody. The antibodies are then compared in appropriate biochemical and biological assays, and the optimal variant is identified.

The binding specificity of antigen-binding polypeptides of the present disclosure can be determined by in vitro assays such as immunoprecipitation, radioimmunoassay (RIA) or enzyme-linked immunoabsorbent assay (ELISA).

Alternatively, techniques described for the production of single-chain units (U.S. Pat. No. 4,694,778; Bird, *Science* 242:423-442 (1988); Huston et al., *Proc. Natl. Acad. Sci. USA* 55:5879-5883 (1988); and Ward et al., *Nature* 334:544-554 (1989)) can be adapted to produce single-chain units of the present disclosure. Single-chain units are formed by linking the heavy and light chain fragments of the Fv region via an amino acid bridge, resulting in a single-chain fusion peptide. Techniques for the assembly of functional Fv fragments in *E. coli* may also be used (Skerra et al., *Science* 242: 1038-1041 (1988)).

Examples of techniques which can be used to produce single-chain Fvs (scFvs) and antibodies include those described in U.S. Pat. Nos. 4,946,778 and 5,258,498; Huston et al., *Methods in Enzymology* 203:46-88 (1991); Shu et al., *Proc. Natl. Sci. USA* 90:1995-1999 (1993); and Skerra et al., *Science* 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, Science 229:1202 (1985); Oi et al., BioTechniques 4:214 (1986); Gillies et al., J. Immunol. Methods 125:191-202 (1989); U.S. Pat. Nos. 5,807,715; 4,816,567; and 4,816397, which are incorporated herein by reference in their entireties.

Humanized antibodies are antibody molecules derived from a non-human species antibody that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen-binding. These framework substitutions are identified by methods well known in the art, e.g., by modeling of the interactions of the CDR and framework residues to identify framework residues important for antigen-binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., Proc. Natl. Sci. USA 91:969-973 (1994)), and chain shuffling (U.S. Pat. No. 5,565,332, which is incorporated by reference in its entirety).

Completely human antibodies are particularly desirable for therapeutic treatment of human patients. Human antibodies can be made by a variety of methods known in the art including phage display methods using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, seeLonberg and Huszar Int. Rev. Immunol. 73:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies which recognize a selected epitope can also be generated using a technique referred to as "guided selection." In this approach a selected non-human monoclonal antibody, e.g., a mouse antibody, is used to guide the selection of a completely human antibody recognizing the same epitope. (Jespers et al., Bio/Technology 72:899-903 (1988). See also, U.S. Pat. No. 5,565,332, which is incorporated by reference in its entirety.)

In another embodiment, DNA encoding desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as E. coli cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

Additionally, using routine recombinant DNA techniques, one or more of the CDRs of the antigen-binding polypeptides of the present disclosure, may be inserted within framework regions, e.g., into human framework regions to humanize a non-human antibody. The framework regions may be naturally occurring or consensus framework regions, and preferably human framework regions (see, e.g., Chothia et al., J. Mol. Biol. 278:457-479 (1998) for a listing of human framework regions). Preferably, the polynucleotide generated by the combination of the framework regions and CDRs encodes an antibody that specifically binds to at least one epitope of a desired polypeptide, e.g., LIGHT. Preferably, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present disclosure and within the skill of the art.

In addition, techniques developed for the production of "chimeric antibodies" (Morrison et al., *Proc. Natl. Acad. Sci. USA:* 851-855 (1984); Neuberger et al., *Nature* 372:604-608 (1984); Takeda et al., *Nature* 314:452-454 (1985)) by splicing genes from a mouse antibody molecule, of appropriate antigen specificity, together with genes from a human antibody molecule of appropriate biological activity can be used. As used herein, a chimeric antibody is a molecule in which different portions are derived from different animal species, such as those having a variable region derived from a murine monoclonal antibody and a human immunoglobulin constant region.

Yet another highly efficient means for generating recombinant antibodies is disclosed by Newman, *Biotechnology* 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

Alternatively, antibody-producing cell lines may be selected and cultured using techniques well known to the skilled artisan. Such techniques are described in a variety of laboratory manuals and primary publications. In this respect, techniques suitable for use in the disclosure as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

Additionally, standard techniques known to those of skill in the art can be used to introduce mutations in the nucleotide sequence encoding an antibody of the present disclosure, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference variable heavy chain region, CDR-H1, CDR-H2, CDR-H3, variable light chain region, CDR-L1, CDR-L2, or CDR-L3. Alternatively, mutations can be introduced randomly along all or part of the coding sequence, such as by saturation mutagenesis, and the resultant mutants can be screened for biological activity to identify mutants that retain activity.

Cancer Treatment

As described herein, the antibodies, variants or derivatives of the present disclosure may be used in certain treatment and diagnostic methods.

The present disclosure is further directed to antibody-based therapies which involve administering the antibodies of the disclosure to a patient such as an animal, a mammal, and a human for treating one or more of the disorders or conditions described herein. Therapeutic compounds of the disclosure include, but are not limited to, antibodies of the disclosure (including variants and derivatives thereof as described herein) and nucleic acids or polynucleotides encoding antibodies of the disclosure (including variants and derivatives thereof as described herein).

The antibodies of the disclosure can also be used to treat or inhibit cancer. PD-1can be overexpressed in tumor cells. Tumor-derived PD-1 can bind to PD-L1 on immune cells thereby limiting antitumor T-cell immunity. Results with small molecule inhibitors, or monoclonal antibodies targeting PD-1 in murine tumor models, indicate that targeted PD-1 therapy is an important alternative and realistic approach to effective control of tumor growth. As demonstrated in the experimental examples, the anti-PD-1 antibodiesactivated the adaptive immune response machinery, which can lead to improved survival in cancer patients.

Accordingly, in some embodiments, provided are methods for treating a cancer in a patient in need thereof. The method, in one embodiment, entails administering to the patient an effective amount of an antibody of the present disclosure. In some embodiments, at least one of the cancer cells (e.g., stromal cells) in the patient expresses, over-express, or is induced to expressPD-1. Induction of PD-1 expression, for instance, can be done by administration of a tumor vaccine or radiotherapy.

Tumors that express the PD-1 protein include those of bladder cancer, non-small cell lung cancer, renal cancer, breast cancer, urethral cancer, colorectal cancer, head and neck cancer, squamous cell cancer, Merkel cell carcinoma, gastrointestinal cancer, stomach cancer, oesophageal cancer, ovarian cancer, renal cancer, and small cell lung cancer. Accordingly, the presently disclosed antibodies can be used for treating any one or more such cancers.

Cellular therapies, such as chimeric antigen receptor (CAR) T-cell therapies, are also provided in the present disclosure. A suitable cell can be used, that is put in contact with an anti-PD-1 antibody of the present disclosure (or alternatively engineered to express an anti-PD-1 antibody of the present disclosure). Upon such contact or engineering, the cell can then be introduced to a cancer patient in need of a treatment. The cancer patient may have a cancer of any of the types as disclosed herein. The cell (e.g., T cell) can be, for instance, a tumor-infiltrating T lymphocyte, a CD4+ T cell, a CD8+ T cell, or the combination thereof, without limitation.

In some embodiments, the cell was isolated from the cancer patient him- or her-self. In some embodiments, the cell was provided by a donor or from a cell bank. When the cell is isolated from the cancer patient, undesired immune reactions can be minimized.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, thyroid cancer, endometrial cancer, melanoma, prostate cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

Treatment of Infections and Immune Disorders

As demonstrated in the experimental examples, the antibodies of the present disclosure can activate immune response which can then be useful for treating infections.

Infection is the invasion of an organism's body tissues by disease-causing agents, their multiplication, and the reaction of host tissues to these organisms and the toxins they produce. An infection can be caused by infectious agents such as viruses, viroids, prions, bacteria, nematodes such as parasitic roundworms and pinworms, arthropods such as ticks, mites, fleas, and lice, fungi such as ringworm, and other macroparasites such as tapeworms and other helminths. In one aspect, the infectious agent is a bacterium, such as Gram negative bacterium. In one aspect, the infectious agent is virus, such as DNA viruses, RNA viruses, and reverse transcribing viruses. Non-limiting examples of viruses include Adenovirus, Coxsackievirus, Epstein-Barr virus, Hepatitis A virus, Hepatitis B virus, Hepatitis C virus, Herpes simplex virus, type 1, Herpes simplex virus, type 2, Cytomegalovirus, Human herpesvirus, type 8, HIV, Influenza virus, Measles virus, Mumps virus, Human papillomavirus, Parainfluenza virus, Poliovirus, Rabies virus, Respiratory syncytial virus, Rubella virus, Varicella-zoster virus.

Also provided, in some embodiments, are methods or uses of the antibody or fragment thereof for the treatment of an immune disorder. Non-limiting examples of immune disorder includeinfection, endotoxic shock associated with infection, arthritis, rheumatoid arthritis, asthma, COPD, pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, arthritis, meningoencephalitis, autoimmune uveitis, immune mediated inflammatory disorders of the central and peripheral nervous system, multiple sclerosis, lupus and Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, pancreatitis, trauma, graft-versus-host disease, transplant rejection, ischaemic diseases, myocardial infarction, atherosclerosis, intravascular coagulation, bone resorption, osteoporosis, osteoarthritis, periodontitis, hypochlorhydia, and infertility related to lack of fetal-maternal tolerance.

The antibodies of the present disclosure can also be used to treat an infectious disease caused by a microorganism, or kill a microorganism, by targeting the microorganism and an immune cell to effect elimination of the microorganism. In one aspect, the microorganism is a virus including RNA and DNA viruses, a Gram positive bacterium, a Gram negative bacterium, a protozoa or a fungus.

A specific dosage and treatment regimen for any particular patient will depend upon a variety of factors, including the particular antibodies, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the antibodies, variants or include but are not limited to intradermal, intramuscular, intraperitoneal, intravenous, subcutaneous, intranasal, epidural, and oral routes. The antigen-binding polypeptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, rectally, parenterally, intracistemally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the antibodies of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the antibodies polypeptides or compositions of the disclosure locally to the area in need of treatment; this may be achieved by, for example, and not by way of limitation, local infusion during surgery, topical application, e.g., in conjunction, with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the disclosure, care must be taken to use materials to which the protein does not absorb.

In another embodiment, the antibodies or composition can be delivered in a vesicle, in particular a liposome (see Langer, 1990, *Science* 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the antigen-binding polypeptide or composition can be delivered in a controlled release system. In one embodiment, a pump may be used (see Sefton, 1987, *CRC Crit. Ref. Biomed. Eng.* 14:201; Buchwald et al., 1980, *Surgery* 88:507; Saudek et al., 1989, *N Engl. J. Med.* 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, *Macromol. Sci. Rev. Macromol. Chem.* 23:61; see also Levy et al., 1985, *Science* 228:190; During et al., 1989, *Ann. Neurol.* 25:351; Howard et al., 1989,1 *Neurosurg.* 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (1990, *Science* 249:1527-1533).

In a specific embodiment where the composition of the disclosure comprises a nucleic acid or polynucleotide encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, *Proc. Natl. Acad. Sci. USA* 88:1864-1868), etc. Alternatively, a nucleic acid can be introduced intracellularly and incorporated within host cell DNA for expression, by homologous recombination.

The amount of the antibodies of the disclosure which will be effective in the treatment, inhibition and prevention of an inflammatory, immune or malignant disease, disorder or condition can be determined by standard clinical techniques. In addition, in vitro assays may optionally be employed to help identify optimal dosage ranges. The precise dose to be employed in the formulation will also depend on the route of administration, and the seriousness of the disease, disorder or condition, and should be decided according to the judgment of the practitioner and each patient's circumstances. Effective doses may be extrapolated from dose-response curves derived from in vitro or animal model test systems.

As a general proposition, the dosage administered to a patient of the antigen-binding polypeptides of the present disclosure is typically 0.1 mg/kg to 100 mg/kg of the patient's body weight, between 0.1 mg/kg and 20 mg/kg of the patient's body weight, or 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the disclosure may be reduced by enhancing uptake and tissue penetration (e.g., into the brain) of the antibodies by modifications such as, for example, lipidation.

The methods for treating an infectious or malignant disease, condition or disorder comprising administration of an antibody, variant, or derivative thereof of the disclosure are typically tested in vitro, and then in vivo in an acceptable animal model, for the desired therapeutic or prophylactic activity, prior to use in humans. Suitable animal models, including transgenic animals, are well known to those of ordinary skill in the art. For example, in vitro assays to demonstrate the therapeutic utility of antigen-binding polypeptide described herein include the effect of an antigen-binding polypeptide on a cell line or a patient tissue sample. The effect of the antigen-binding polypeptide on the cell line and/or tissue sample can be determined utilizing techniques known to those of skill in the art, such as the assays disclosed elsewhere herein. In accordance with the disclosure, in vitro assays which can be used to determine whether administration of a specific antigen-binding polypeptide is indicated, include in vitro cell culture assays in which a patient tissue sample is grown in culture, and exposed to or otherwise administered a compound, and the effect of such compound upon the tissue sample is observed.

Various delivery systems are known and can be used to administer an antibody of the disclosure or a polynucleotide encoding an antibody of the disclosure, e.g., encapsulation in liposomes, microparticles, microcapsules, recombinant cells capable of expressing the compound, receptor-mediated endocytosis (see, e.g., Wu and Wu, 1987, *J. Biol. Chem.* 262:4429-4432), construction of a nucleic acid as part of a retroviral or other vector, etc.

Diagnostic Methods

Over-expression of PD-1 is observed in certain tumor samples, and patients having PD-1-over-expressing cells are likely responsive to treatments with the anti-PD-1 antibodies of the present disclosure. Accordingly, the antibodies of the present disclosure can also be used for diagnostic and prognostic purposes.

A sample that preferably includes a cell can be obtained from a patient, which can be a cancer patient or a patient desiring diagnosis. The cell be a cell of a tumor tissue or a tumor block, a blood sample, a urine sample or any sample from the patient. Upon optional pre-treatment of the sample, the sample can be incubated with an antibody of the present disclosure under conditions allowing the antibody to interact with a PD-1 protein potentially present in the sample. Methods such as ELISA can be used, taking advantage of the anti-PD-1 antibody, to detect the presence of the PD-1 protein in the sample.

Presence of the PD-1 protein in the sample (optionally with the amount or concentration) can be used for diagnosis of cancer, as an indication that the patient is suitable for a treatment with the antibody, or as an indication that the patient has (or has not) responded to a cancer treatment. For a prognostic method, the detection can be done at once, twice or more, at certain stages, upon initiation of a cancer treatment to indicate the progress of the treatment.

Compositions

The present disclosure also provides pharmaceutical compositions. Such compositions comprise an effective amount of an antibody, and an acceptable carrier. In some embodiments, the composition further includes a second anticancer agent (e.g., an immune checkpoint inhibitor).

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

EXAMPLES

Example 1

Generation of Human Monoclonal Antibodies Against Human PD-1

Cloning of Full-Length Human PD-1 cDNA

Human T lymphocytes were isolated from human peripheral blood lymphocytes (PBMC) with MACS beads (MiltenyiBiotec). Total RNA was extracted from human T cells with RNeasy Mini Kit (QIAGEN) and cDNA was obtained by reverse-transcription PCR (SuperScript First-Strand Synthesis System, Invitrogen). Full length cDNA encoding the hPD-1 was generated by RT-PCR using the sense primer (5'-CTGTCTAGAATGCAGATCCCACAGGCGCC, SEQ ID NO: 47) and anti-sense primer (5'-GGATCCTCAGAGGGGCCAAGAGCAGT, SEQ ID NO: 48) from human T cell mRNA. The sequences were verified by DNA sequencing and comparing with NCBI database (NM-005018.2).

Establish hPD-1 stable expression cell line: After digestion with XbaI and BamH I, the hPD-1 PCR fragments were cloned into pcDNA3.1(−) vector (Invitrogen). Then pcDNA-hPD-1 full-length plasmids were transfected into Chinese hamster ovary (CHO) cells using lipofectamine 2000 (Invitrogen). Cell lines stably expressing hPD-1(CHO/hPD-1) were selected by G418 and screened by flow cytometry.

Production of human PD-1 Ig fusion protein: The cDNA of hPD-1 mIg and hPD-1 hIg fusion protein containing extracellular domain of hPD-1 was amplified by PCR from pcDNA-hPD-1 full-length by specific primers. The PCR fragments digested with EcoR I and BgI II were fused to CH2-CH3 domain of mouse IgG2a heavy chain in the expression plasmid pmIgG or human IgG1 heavy chain in the expression plasmid phIgG (H Dong et al. Nat Med. 1999; 5:1365-1369). The protein in the culture supernatant was purified by a protein A Sepharose column (HiTrap Protein A HP, GE healthcare). The purified protein was confirmed by SDA-PAGE electrophoresis.

Generation of Monoclonal Antibody: The 8-10 weeks old female Balb/c mice were immunized subcutaneously (s.c.) at multiple sites with 200 μl of emulsion comprising 100 μg of hPD-1 mIg fusion protein and complete Freund's adjuvant (CFA) (Sigma-Aldrich). 3 weeks later mice were immunized with 50-100 μg of protein with incomplete Freund's adjuvant (IFA) (Sigma-Aldrich) by s.c.for a total of three times. Mice were bled 2 weeks after each immunization for serum titer testing. When the titer is sufficient, the mice were boosted with 60 μg of protein in PBS by intraperitoneal injection (i.p.). The hybridomas were obtained by fusing immunized mouse spleen cells and 5P2/0-Ag14 myeloma cell line (from ATCC). Boosted mouse was sacrificed by carbon dioxide and spleen was harvestedaseptically. Whole spleen was dissociated into single-cell suspensions and red blood cells were lysed by ACK buffer. 5P2/0-Ag14 myeloma and spleen cells were mixed at 1:1 ratio in a 50 ml conical centrifuge tubes. After centrifuge, supernatant was discarded and cell fusion was performed with 50% polyethylene glycol (Roche). The fused cells were cultured for 8-10 days in HAT selection medium, the hybridoma culture supernatants were screened for binding to hPD-1 expressing cells with a high throughput transfection and screening systems (S Yao et al. Immunity. 2011; 34(5):729-40) and the positive clones were confirmed by flow cytometry analysis. Thesubcloning of positive hybridoma was performed using the limiting dilution technique for at least 5 times to achieve a purely monoclonal culture.

Example 2

Characterization of PD-1 Monoclonal Antibodies

Isotype of the MAbs: The isotype of mAbs was identified using Mouse Immunoglobutin Isotyping Kit (BD Biosciences). All the five PD-1 mAbs were identified to be IgG1 isotype and κ chain.

Figure 2:
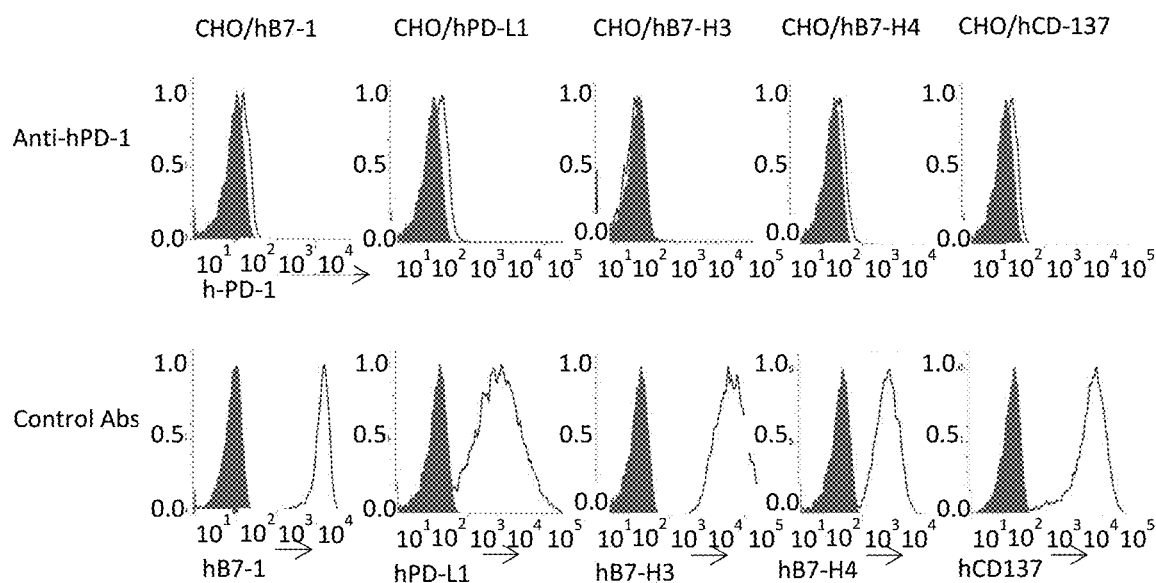
FIG. 2 shows that anti-hPD-1 does not bind with hB7-1, hPD-L1, hB7-H3, hB7-H4 and hCD137.

The binding specificity of anti-hPD-1: The CHO cells that express hPD-1(CHO/hPD-1) on surface were used to determine the specificity of PD-1mAbs by flow cytometry. CHO/hPD-1 cells were incubated anti-PD-1 mAbs on ice. After incubation, the cells were washed and further incubated with anti-mIgG-APC (eBiosciences). Flow cytometry analysis was performed using a FACSVerse (BD Biosciences). The data showed that all the five hPD-1 mAbs bound with high specificity to hPD-1 (FIG. 1). To exclude the possibility that the hPD-1 mAbs bind other proteins, CHO cells transfected hB7-1, hPD-L1, hB7-H3, hB7-H4, hCD137 or other protein molecules were stained with anti-hPD-1 mAb by flow cytometric analysis. These cells were also stained with their respective positive antibodies respectively as positive control. The data demonstrated that anti-PD-1 mAbdid not bind these tested proteins (FIG. 2)

Species cross reactivity: To assess the species-specificities of the anti-hPD-1 mAbs, the peripheral blood mononuclear cell (PBMC) of cynomolgus monkey (from Guangdong landau Biotechnology Company) were isolated from peripheral blood with Ficoll (Sigma-Aldrich). The PBMC were suspended in RPMI 1640 medium containing 10% FCS and put into a 24 well-plate which pre-coated 1 μg/ml of anti-hCD3. The cells cultured for two days. The cells were stained with anti-hPD-1 first. After wash, the cells were stained with anti-mIgG-APC and CD3-FITC; CD8-PerCP for flow cytometry analysis. In addition, the cross reactivity of the mAbs to mouse PD-1 was determined by flow cytometry using mouse PD-1 transfected CHO cells (CHO/mPD-1).

Figure 3:
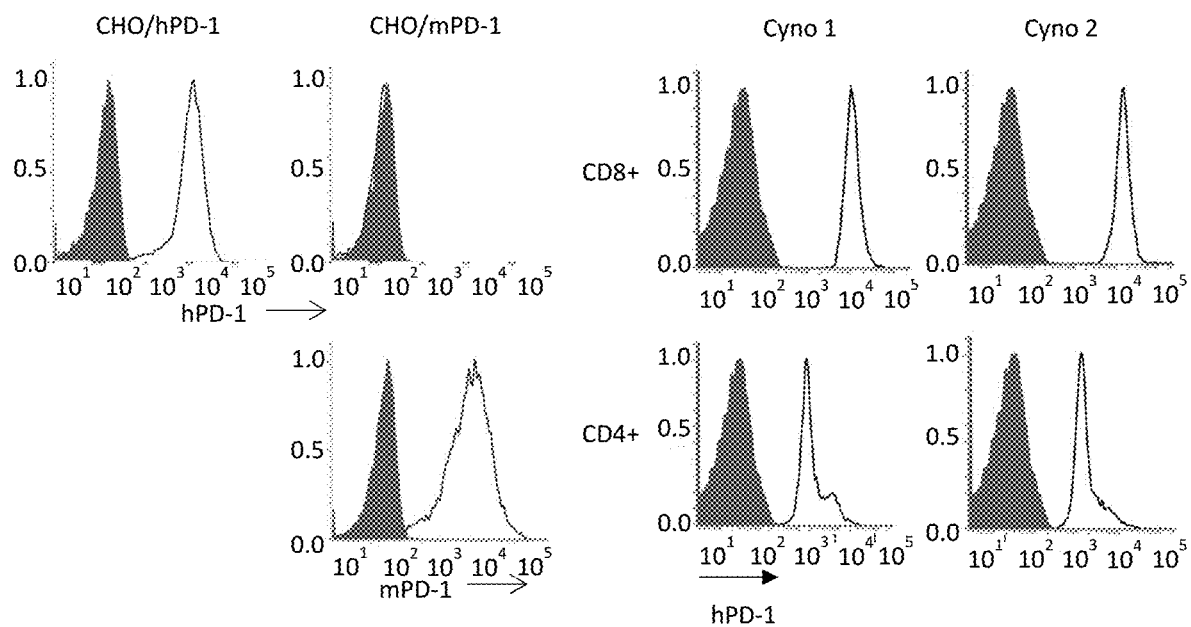
FIG. 3 shows that hPD-1 mAb can bind to both human and cynomolgus monkey cell PD-1 proteins without displaying cross-binding to mPD-1.

The data demonstrated that anti-hPD-1mAb can bind to PD-1proteinson both human and cynomolgus monkey T cell, no cross-binding was found to mouse PD-1(FIG. 3).

Ligand blockade: To examine the blockade of ligand binding, 100 ng of hPDlhIg fusion protein were pre-incubated with indicated dose of mAb (400, 300, 200, 100, 50 ng/10 ul) or control Ig for 30 min at 4° C., then used to stain CHO/hB7-H1 cells. The cells were washed and further stained withgoat anti-hIgG-APC. The blocking effect was assessed with flow cytometry.

Figure 4:
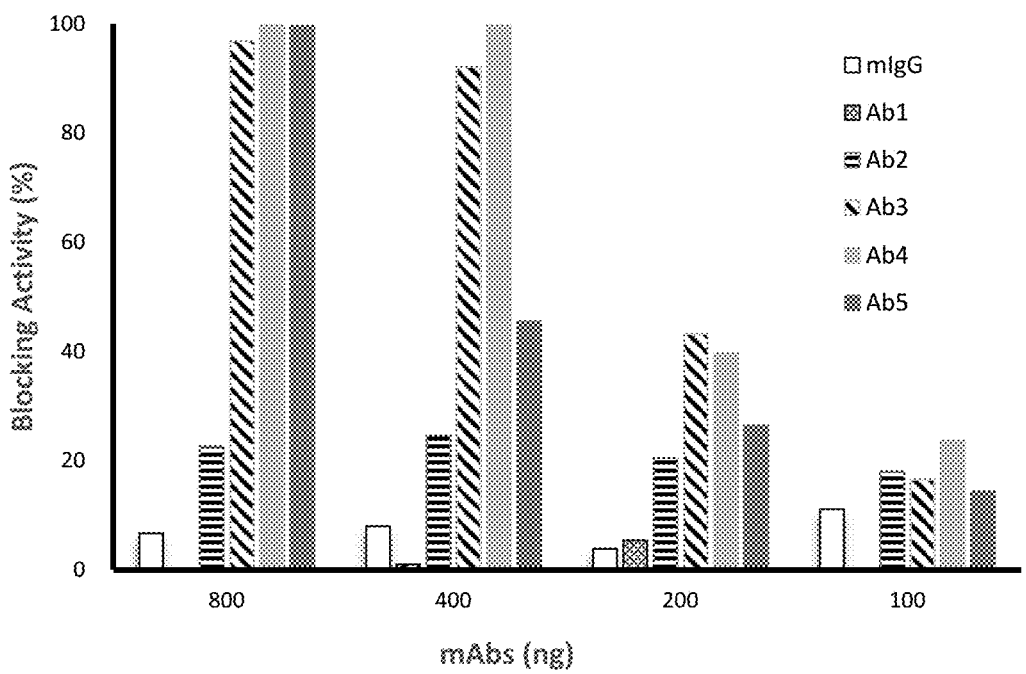
FIG. 4 shows that hPD-1 mAbs can have a blocking effect on the binding of hPD-1 to hPD-L1 dependant on dosage.

The data demonstrated that anti-hPD-1 mAbs 1 and 2 (Ab1 and Ab2) have no effect on ligand blockade. Ab3, Ab4 and Ab5 can block the hPD-1 fusion protein bind to hPD-L1 in a dose-dependent manner (FIG. 4).

Competitive binding assay: Competitive binding assay was performed to investigate where these mAbs recognize same or different binding sites of hPD-1 protein. CHO/hPD-1 cells were pre-incubated with excessive amount (10 μg) of five PD-1 mAbs respectively at 4° C. for 30 min. After wash, the cells were incubated 50 ng of different biotin labeled mAbs at 4° C. for 20 min. The binding effect of mAbs was measured using flow cytometry analysis.

Figure 5:
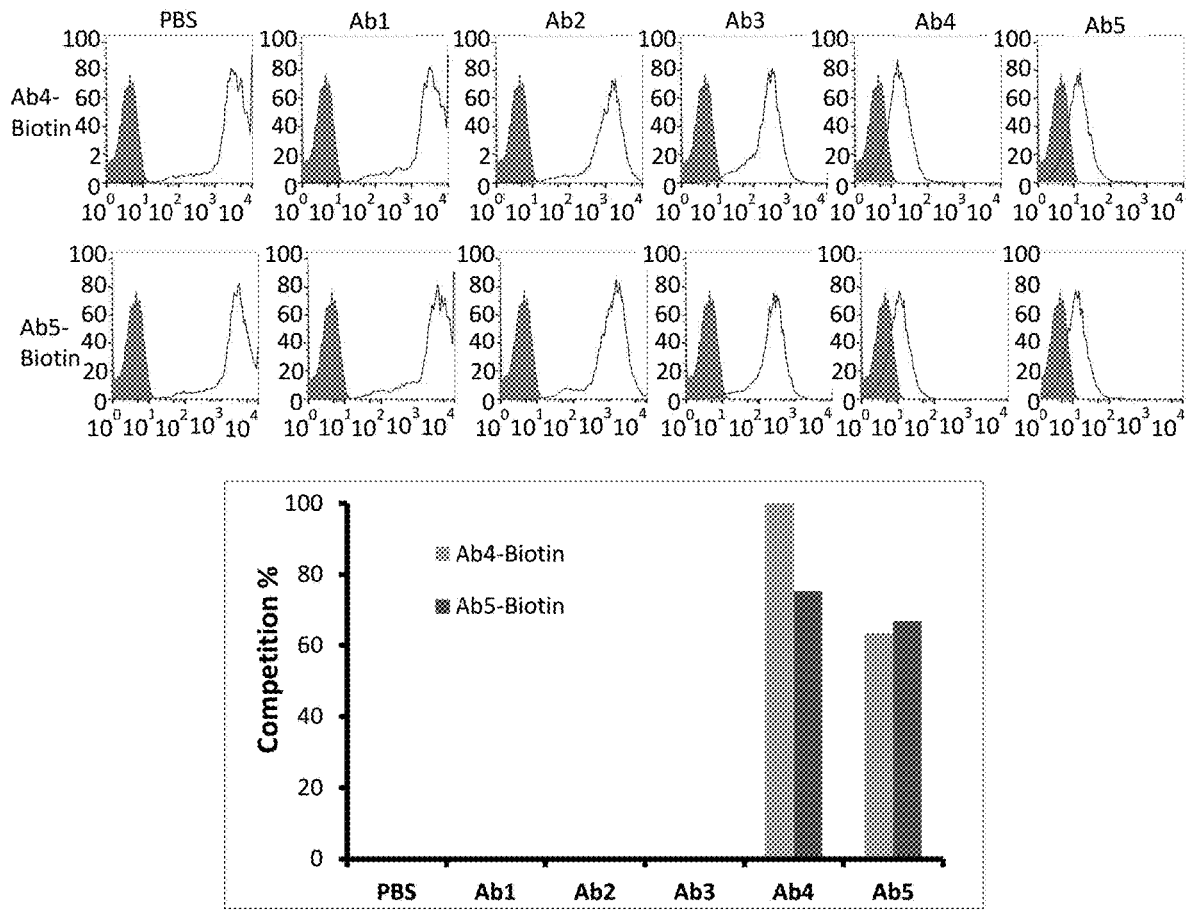
FIG. 5 shows abrogating and blocking effects of hPD-1 mAbs when observed in a competitive-binding environment.

Flow cytometry analysis showed that Ab4 and Ab5 completely abrogated each other binding to hPD-1 proteins, a saturated dose of Ab3 had partly block effect to Ab4 and Ab5 binding and Ab1 and Ab2 had no block effect on binding of Ab4 and Ab5 to hPD-1 (FIG. 5). Therefore, the binding sites on PD-1 for Ab4 and Ab5 may overlap. Ab1 or Ab2 and Ab4 or Ab5 binds to PD-1 through different interfaces, which also validated by ligand blockade test.

Example 3

Sequencing of Anti-PD-1 Antibody-Producing Hybridomas and Antibody Humanization

Figure 6:
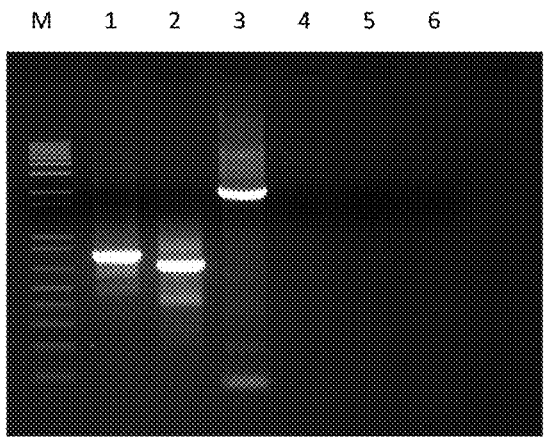
FIG. 6 shows the results of gel electrophoresis analysis confirming RACE products.

Sequencing of anti-PD-1 antibody-producing hybridomas: 1×10$^7$ hybridoma cells were harvest and washed with PBS. Messenger RNAs were extracted from hybridomas using RAeasy Mini Kit (Qiagen). RACE-Ready first-Strand cDNAs were synthesized using SMARTer RACE cDNA Amplification Kit (Clontech). Following reverse transcription, 5' RACE PCR reactions were performed with ready cDNA as template and with 5' universal primer (UPM) provided by the kit and 3'gene specific primers (GSP1) designed by the mouse IgG1 heavy chain variable region and κ light chain gene sequences. RACE products were determined by gel electrophoresis analysis (FIG. 6). PCR productions were cloned into a T vector using Zero Blunt TOPO PCR Cloning Kit (Invitrogen). After transformation, the plasmids were verified by sequencing analysis. The antibody gene fragments were analyzed by using VBASE2 http://www.vbase2.org). The sequences are disclosed in the (Table 2).

TABLE 2

Sequences of Murine antibodies

| Name (SEQ ID NO:) | Sequence (underlined bold shows CDR) |
|---|---|
| Murine Ab2 VH (19) | SQVQLQQSGAELARPGASVKMSCKASGYTFTSYTMHWVKQRPGQGLEWIGYINPTTGYTN YNQKFKDKANPTTGYTNYNQKFKDKATLTADKSSSTAYMQLSSLTSEDSAVYYCARDDAY YSGYWGQGTTLTVSS |
| Murine Ab2 VH (20) | TCCCAGGTCCAGCTGCAGCAGTCTGGGGCTGAACTGGCAAGACCTGGGGCCTCAGTGAAG ATGTCCTGCAAGGCTTCTGGCTACACCTTTACTAGTTACACGATGCACTGGGTAAAACAG AGGCCTGGACAGGGTCTGGAATGGATTGGATACATTAATCCTACTACTGGTTATACTAAT TACAATCAGAAGTTCAAGGACAAGGCCACATTGACTGCAGACAAATCCTCCAGCACAGCC TACATGCAATTGAGCAGCCTGACATCTGAGGACTCTGCAGTCTATTACTGTGCAAGAGAT GATGCTTACTACTCGGGCTACTGGGGCCAAGGCACCACTCTCACAGTCTCCTCA |

TABLE 2-continued

Sequences of Murine antibodies

| Name (SEQ ID NO:) | Sequence (underlined bold shows CDR) |
|---|---|
| Murine Ab2 VK (21) | DIQMTQSPASLSVSVGETVTITCRASENIYSNLAWYRQKQGKSPQLLVYAAKNLADGVPSRFSGSGSGTQYSLKINSLQSEDFGSYYCQHFWGTPWTFGGGTKLEIKR |
| Murine Ab2 VK (22) | GACATCCAGATGACTCAGTCTCCAGCCTCCCTATCTGTATCTGTGGGAGAAACTGTCACCATCACATGTCGAGCAAGTGAGAATATTTACAGTAATTTAGCATGGTATCGGCAGAAACAGGGAAAATCTCCTCAGCTCCTGGTCTATGCTGCAAAAAACTTAGCAGATGGTGTGCCATCAAGGTTCAGTGGCAGTGGATCAGGCACACAGTATTCCCTCAAGATCAACAGCCTGCAGTCTGLAGATTTTGGGAGTTATTACTGTCAACATTTTTGGGGTACTCCGTGGACGTTCGGTGGAGGCACCAAGCTGGAAATCAAACGG |
| Murine Ab3 VH (23) | VQLVESGGGLVKPGGSLKLSCAASGFAFSSYDMSWVRQTPEKRLVWVAYITIGGGTTYYSDTVKRLVWVAYITIGGGTTYYSDTVKGRFTISRDNAKNTLYLQMSSLKSEDTAMYYCARHRYDYFAMDNWGHGTSVTVSS |
| Murine Ab3 VH (24) | GAAGTGCAGCTGGTGGAGTCGGGGGGAGGCTTAGTGAAGCCTGGAGGGTCCCTGAAACTCTCCTGTGCAGCCTCTGGATTCGCTTTCAGTAGCTATGACATGTCTTGGGTTCGCCAGACTCCGGAGAAGAGGCTGGTGTGGGTCGCATACATTACTATTGGTGGTGGCACCACCTACTATTCAGACACTGTGAAGGGCCGATTCACCATCTCCAGAGACAATGCCAAGAACACCCTGTACCTGCAAATGAGCAGTCTGAAGTCTGAGGACACAGCCATGTATTACTGTGCAAGACATAGGTACGATTACTTCGCTATGGACAACTGGGGTCATGGAACCTCAGTCACCGTCTCCTCA |
| Murine Ab3 VK (25) | DIVLTQSPASLAVSLEHRATISCQASENVDNYGINFMNWFQHKPAQPPQLLIYVSSNLGSGVPAKFSGSGSGTDFSLNIHPMEEDDTAMYFCQQSKDVPWTFSGGTKLEIKR |
| Murine Ab3 VK (26) | GACATTGTGCTGACCCAATCTCCAGCTTCTTTGGCTGTGTCTCTAGAGCACAGGGCCACCATCTCCTGCCAAGCCAGCGAAAATGTTGATAATTATGGCATTAATTTTATGAACTGGTTCAACACAAACCAGCACAGCCACCCCAACTCCTCATCTATGTTTCATCCAACCTAGGATCCGGGGTCCCTGCCAAGTTTAGTGGCAGTGGGTCTGGAACAGACTTCAGCCTCAACATCCATCCTATGGAAGAAGATGATACTGCAATGTATTTCTGTCAGCAAAGTAAGGACGTTCCGTGGACGTTCAGTGGAGGCACCAAACTGGAAATCAAACGG |
| Murine Ab4 VH (27) | EVKLVESGGGLVQPGGSLKLSCAASGFTFSSYTMSWIRQTPEKRLEWVAYISHGGGDTYYPDTVKGRFTISRDNAKNTLYLQMSSLKSEDTAMYYCARHSGYERGYYYVMDYWGQGTSVTVSS |
| Murine Ab4 VH (28) | GAAGTGAAGTTGGTGGAGTCTGGGGGAGGTTTAGTGCAGCCTGGAGGGTCCCTGAAACTCTCCTGTGCAGCCTCTGGATTCACTTTCAGTAGCTATACCATGTCTTGGATTCGCCAGACTCCAGAGAAGAGGCTGGAGTGGGTCGCATACATTAGTCATGGTGGTGGTGACACCTACTATCCAGACACTGTAAAGGGCCGATTCACCATCTCCAGGGACAATGCCAAGAACACCCTGTACCTGCAAATGAGCAGTCTGAAGTCTGAGGACACGGCCATGTATTACTGTGCAAGACATAGTGGTTACGAGAGGGGATATTACTATGTTATGGATTACTGGGGTCAAGGAACCTCAGTCACCGTCTCCTCA |
| Murine Ab4 VK (29) | DIVLTQFPTSLAVSLGQRATISCRASESVDYYGFSFINWFQQKPGQPPKLLIYAASNQGSGVPARFGGSGSGTDFSLNIHPMEEDDTAMYFCQQSKEVPWTFGGGTKLEIK |
| Murine Ab4 VK (30) | GACATTGTGCTGACCCAATTTCCAACTTCTTTGGCTGTGTCTCTAGGGCAGAGGGCCACCATCTCCTGCAGAGCCAGCGAAAGTGTTGATTACTATGGCTTTAGTTTTATAAACTGGTTCAACAGAAACCAGGACAGCCACCCAAACTCCTCATCTATGCTGCATCCAACAGGGATCCGGGGTCCCTGCCAGGTTTGGTGGCAGTGGGTCTGGACAGACTTCAGCCTCAACATCCATCCTATGGAGGAGGATGATACTGCAATGTATTTCTGTCAGCAAAGTAAGGAGGTTCCGTGGACGTTCGGTGGAGGCACCAAGCTGGAAATCAAACGG |

Protein expression and function determination of recombinant antibody: To ensure the correctness of the recombinant antibody sequence, the full length sequences of recombinant antibody heavy chain and light chain were cloned into pcDNA3.1 vectors respectively and transiently transfected HEK 293T cells. The proteins from cell culture supernatant were purified with protein G sepharose column (GE healthcare) for function assess.

Figure 7:
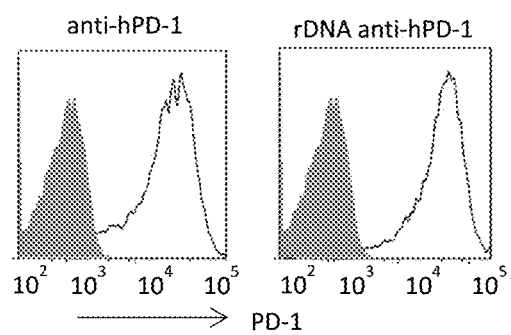
FIG. 7 shows the ability of recombinant DNA antibodies to bind PD-1 (A), and their blocking effect on the binding ability of PD-1 to PD-L1 (B).
Figure 7:
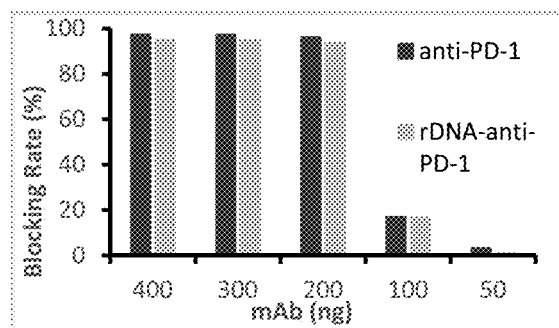

The cytometry analysis data demonstrated that the recombinant antibodies can bind hPD-1 protein and can block the hPD-1 fusion protein bind to PD-L1 protein (FIG. 7, panels A, B)

Anti-human PD-1 antibodies humanization: Humanization was performed based on the variable heavy chain (VH) and variable light chain (VL) sequences of anti-hPD-1 hybridomas. Generally, a mouse-human chimeric mAb which composed of parental mouse VH and VL sequences and human IgG4-S228P constant region and human κ chain were constructed firstly. After identifying the character of chimeric antibody, three VL and three VL humanized sequences were designed and used to make the nine humanized antibodies. The sequences list in (Tables 3A and 3B).

TABLE 3A

Chimeric antibody (human IgG4-S228P backbone)

| Name (SEQ ID NO:) | Sequence (underlined bold shows CDR) |
|---|---|
| Chimeric heavy chain (31) | EVKLVESGGGLVQPGGSLKLSCAASGFTFSSYTMSWIRQTPEKRLEWVAYISHGGGDTYYPDTVKGRFTISRDNAKNTLYLQMSSLKSEDTAMYYCARHSGYERGYYYVMDYWGQGTSVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| Chimeric heavy chain (32) | CGAAGTGAAGTTGGTGGAGTCTGGGGGAGGTTTAGTGCAGCCTGGAGGGTCCCTGAAACTCTCCTGTGCAGCCTCTGGATTCACTTTCAGTAGCTATACCATGTCTTGGATTCGCCAGACTCCAGAGAAGAGGCTGGAGTGGGTCGCATACATTAGTCATGGTGGTGGTGACACCTACTATCCAGACACTGTAAAGGGCCGATTCACCATCTCCAGGGACAATGCCAAGAACACCCTGTACCTGCAAATGAGCAGTCTGAAGTCTGAGGACACGGCCATGTATTACTGTGCAAGACATAGTGGTTACGAGAGGGGATATTACTATGTTATGGATTACTGGGGTCAAGGAACCTCAGTCACCGTCTCCTCAGCTAGCACCAAGGGCCCCAGCGTGTTTCCTCTCGCTCCCTGCAGCCGGAGCACATCCGAGAGCACCGCTGCTCTGGGCTGTCTCGTGAAGGACTACTTCCCTGAACCCGTCACCGTCAGCTGGAATAGCGGCGCCCTGACATCCGGCGTCCACACATTCCCCGCTGTCCTGCAGAGCAGCGGCCTGTACAGCCTGAGCTCCGTGGTCACCGTGCCTAGCAGCAGCCTGGGAACAAAGACCTACACCTGCAACGTGGACCATAAGCCCTCCAACACCAAGGTGGACAAGCGGGTGGAATCCAAGTATGGACCCCCCTGTCCTCCTTGCCCTGCTCCTGAATTTCTCGGAGGCCCCTCCGTCTTCCTGTTTCCCCCCAAGCCCAAGGACACCCTGATGATCTCCCGGACACCCGAAGTCACCTGCGTCGTGGTGGATGTCAGCCAGGAAGATCCCGAGGTGCAGTTCAACTGGTACGTGGACGGAGTGGAGGTGCATAACGCCAAAACCAAGCCCAGGGAAGAGCAGTTCAACAGCACCTATCGGGTCGTGTCCGTGCTCACCGTCCTGCATCAGGATTGGCTCAACGGCAAGGAGTACAAGTGCAAGGTGTCCAACAAGGGCCTGCCCTCCTCCATCGAGAAGACCATCTCCAAGGCTAAGGGCCAACCTCGGGAGCCCCAAGTGTATACCCTCCCTCCCAGCCAGGAGGAGATGACCAAGAATCAAGTGAGCCTGACCTGCCTCGTGAAGGGATTTTACCCCTCCGACATCGCTGTGGAATGGGAAAGCAATGGCCAACCTGAGAACAACTACAAGACCACACCCCCCGTGCTGGACTCCGATGGCTCCTTCTTCCTGTACAGCAGGCTGACCGTGGACAAATCCCGGTGGCAAGAGGGAAACGTGTTCAGCTGCTCCGTGATGCACGAGGCTCTCCACAACCACTACACCCAGAAGAGCCTCTCCCTGAGCCTCGGCAAGTAGTAA |
| Chimeric light chain (33) | DIVLTQFPTSLAVSLGQRATISCRASESVDYYGFSFINWFQQKPGQPPKLLIYAASNQGSGVPARFGGSGSGTDFSLNIHPMEEDDTAMYFCQQSKEVPWTFGGGTKLEIKRTVAAPSVFIFPPSDEQLKSGTASVVCLLNNFYPREAKVQWKVDNALQSGNSQESVTEQQDSKDSTYSLTSTLTLSKADYEKHKVYACEVTHQGLSSPVTKSFNRGEC |
| Chimeric light chain (34) | AGACATTGTGCTGACCCAATTTCCAACTTCTTTGGCTGTGTCTCTAGGGCAGAGGGCCACCATCTCCTGCAGAGCCAGCGAAAGTGTTGATTACTATGGCTTTAGTTTTATAAACTGGTTCCAACAGAAACCAGGACAGCCACCCAAACTCCTCATCTATGCTGCATCCAACCAGGGATCCGGGGTCCCTGCCAGGTTTGGTGGCAGTGGGTCTGGGACAGACTTCAGCCTCAACATCCATCCTATGGAGGAGGATGATACTGCAATGTATTTCTGTCAGCAAAGTAAGGAGGTTCCGTGGACGTTCGGTGGAGGCACCAAGCTGGAAATCAAGCGGACCGTGGCCGCCCCCAGCGTGTTCATCTTCCCTCCCAGCGACGAGCAGCTGAAGTCTGGCACCGCCAGCGTGGTGTGCCTGCTGAACAACTTCTACCCCCGCGAGGCCAAGGTGCAGTGGAAGGTGGACAACGCCCTGCAGAGCGGCAACAGCCAGGAGAGCGTGACCGAGCAACAGGACTCCAAGGACAGCACCTACAGCCTGACCAGCACCCTGACCCTGAGCAAGGCCGACTACGAGAAGCACAAGGTGTACGCCTGCGAGGTGACCCACCAGGGACTGTCTAGCCCCGTGACCAAGAGCTTCAACCGGGGCGAGTGCTAA |

TABLE 3B

Humanized heavy chain and light chain variable regions

| Name (SEQ ID NO:) | Sequence (underlined bold shows CDR) |
| --- | --- |
| VH variant a (35) | EVQLVESGGGLVQPGGSLRLSCAASGFTFSSYTMSWVRQAPGKGLEWVSYISHGGGDTYY ADSVKGRFTISRDNSKNTLYLQMNSLRAEDTAVYYCARHSGYERGYYYVMDYWGQGTLVT VSSA |
| VH variant a (36) | CGAAGTGCAGCTGGTGGAATCTGGCGGCGGACTGGTGCAGCCTGGCGGATCTCTGAGACT GTCTTGTGCCGCCTCCGGCTTCACCTTCTCCAGCTACACCATGTCCTGGGTGCGACAGGC TCCTGGCAAGGGCCTGGAATGGGTGTCCTACATCTCTCACGGCGGAGGCGACACCTACTA CGCCGACTCTGTGAAGGGCCGGTTCACCATCTCCCGGGACAACTCCAAGAACACCCTGTA CCTGCAGATGAACTCCCTGCGGGCCGAGGACACCGCCGTGTACTACTGTGCTCGGCACTC TGGCTACGAGCGGGGCTACTACTACGTGATGGACTACTGGGGCCAGGGCACCCTCGTGAC CGTGTCATCTGCT |
| VH variant b (37) | EVQLVESGGGLVQPGGSLRLSCAASGFTFSSYTMSWVRQAPGKGLEWVSYISHGGGDTYY PDSVKGRFTISRDNSKNTLYLQMNSLRAEDTAVYYCARHSGYERGYYYVMDYWGQGTLVT VSS |
| VH variant b (38) | CGAAGTGCAGCTGGTGGAATCTGGCGGCGGACTGGTGCAGCCTGGCGGATCTCTGAGACT GTCTTGTGCCGCCTCCGGCTTCACCTTCTCCAGCTACACCATGTCCTGGGTGCGACAGGC TCCTGGCAAGGGCCTGGAATGGGTGTCCTACATCTCTCACGGCGGAGGCGACACCTACTA CCCCGACTCTGTGAAGGGCCGGTTCACCATCTCCCGGGACAACTCCAAGAACACCCTGTA CCTGCAGATGAACTCCCTGCGGGCCGAGGACACCGCCGTGTACTACTGTGCTCGGCACTC TGGCTACGAGCGGGGCTACTACTACGTGATGGACTACTGGGGCCAGGGCACCCTCGTGAC CGTGTCATCTGCT |
| VH variant c (39) | EVKLLESGGGLVQPGGSLRLSCAASGFTFSSYTMSWVRQAPGKGLEWVSYISHGGGDTYY PDSVKGRFTISRDNSKGGDTYYPDSVKGRFTISRDNSKNTLYLQMNSLRAEDTAVYYCAR HSGYERGYYYVMDYWGKGTTVTVSSA |
| VH variant c (40) | GAAGTGAAGCTGCTGGAATCTGGCGGCGGACTGGTGCAGCCTGGCGGATCTCTGAGACTG TCTTGTGCCGCCTCCGGCTTCACCTTCTCCAGCTACACCATGTCCTGGGTGCGACAGGCT CCTGGCAAGGGCCTGGAATGGGTGTCCTACATCTCTCACGGCGGAGGCGACACCTACTAC CCCGACTCTGTGAAGGGCCGGTTCACCATCTCCCGGGACAACTCCAAGAACACCCTGTAC CTGCAGATGAACTCCCTGCGGGCCGAGGACACCGCCGTGTACTACTGTGCTCGGCACTCT GGCTACGAGCGGGGCTACTACTACGTGATGGACTACTGGGGCAAGGGCACCACCGTGACC GTGTCATCTGCT |
| VK variant a (41) | DIVMTQSPDSLAVSLGERATINCKSSESVDYYGFSFLNWFQQKPGQPPKLLIYAASNRES GVPDRFSGSGSGTDFTLTISSLQAEDVAVYYCQQSKEVPWTFGQGTKLEIKR |
| VK variant a (42) | AGACATCGTGATGACCCAGTCCCCCGACTCCCTGGCTGTGTCTCTGGGCGAGAGAGCCAC CATCAACTGCAAGTCCTCCGAGTCCGTGGACTACTACGGCTTCTCCTTCCTGAACTGGTT CCAGCAGAAGCCCGGCCAGCCCCCTAAGCTGCTGATCTACGCCGCCTCCAACCGCGAGTC TGGCGTGCCCGATAGATTCTCCGGCTCTGGCTCTGGCACCGACTTTACCCTGACCATCAG CTCCCTGCAGGCCGAGGATGTGGCCGTGTACTACTGCCAGCAGTCCAAAGAGGTGCCCTG GACCTTCGGCCAGGGCACAAAGCTGGAAATCAAGCGG |
| VK variant b (43) | DIVMTQSPDSLAVSLGERATINCKASESVDYYGFSFLNWFQQKPGQPPKLLIYAASNRES GVPDRFSGSGSGTDFTLTISSLQAEDVAVYYCQQSKEVPWTFGQGTKLEIKR |
| VK variant b (44) | AGACATCGTGATGACCCAGTCCCCCGACTCCCTGGCTGTGTCTCTGGGCGAGAGAGCCAC CATCAACTGCAAGGCCTCCGAGTCCGTGGACTACTACGGCTTCTCCTTCCTGAACTGGTT CCAGCAGAAGCCCGGCCAGCCCCCTAAGCTGCTGATCTACGCCGCCTCCAACCGCGAGTC TGGCGTGCCCGATAGATTCTCCGGCTCTGGCTCTGGCACCGACTTTACCCTGACCATCAG CTCCCTGCAGGCCGAGGATGTGGCCGTGTACTACTGCCAGCAGTCCAAAGAGGTGCCCTG GACCTTCGGCCAGGGCACAAAGCTGGAAATCAAGCGG |
| VK variant c (45) | DIQLTQSPDSLSVSLGERATINCKASESVDYYGFSFLNWFQQKPGQPPKLLIYAASNRQS GVPDRFSGSGSGTDFTLTISSLQAEDVAVYFCQQSKEVPWTFGQGTKLEIKR |
| VK variant c (46) | GACATCCAGCTGACCCAGTCCCCCGACTCCCTGTCTGTGTCTCTGGGCGAGAGAGCCACC ATCAACTGCAAGGCCTCCGAGTCCGTGGACTACTACGGCTTCTCCTTCCTGAACTGGTTC CAGCAGAAGCCCGGCCAGCCCCCTAAGCTGCTGATCTACGCCGCCTCCAACCGCCAGTCT GGCGTGCCCGATAGATTCTCCGGCTCTGGCTCTGGCACCGACTTTACCCTGACCATCAGC TCCCTGCAGGCCGAGGATGTGGCCGTGTACTTCTGCCAGCAGTCCAAAGAGGTGCCCTGG ACCTTCGGCCAGGGCACAAAGCTGGAAATCAAGCGG |

Example 4

Characteristics and Functions of Humanized Antibodies

The binding activity of the humanized antibodies: CHO/hPD-1 cells were incubated with serially diluted mAbs. The binding effects of nine humanized antibodies to PD-1 protein were assessed using flow cytometry analysis and compared to chimeric parental antibody.

Figure 8:
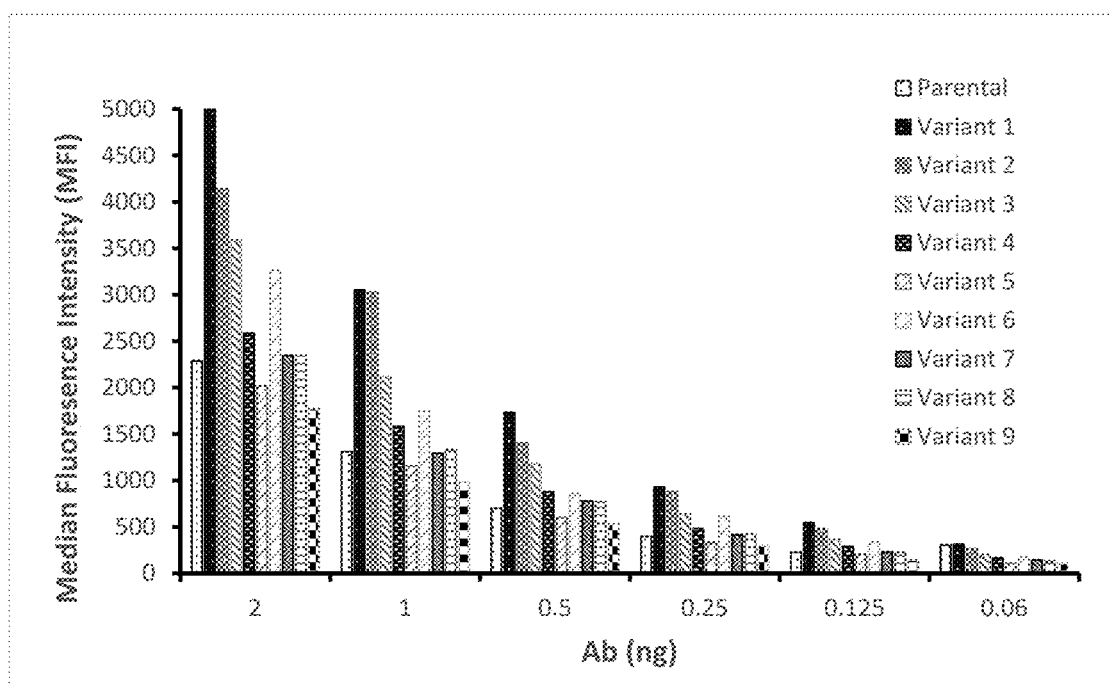
FIG. 8 shows that nine humanized antibodies displayed various binding affinities to PD-1 including both higher and lower than the parental antibody.

The flow cytometry analysis results showed that the binding activity of some mutant combinations is higher than that parental antibody; some are same or slightly lower than parental antibody (FIG. 8). The mutant combinations are listed in Table 4 below.

| Name | VH variant | VK variant |
|---|---|---|
| Variant 1 | a | a |
| Variant 2 | a | b |
| Variant 3 (TY101) | a | c |
| Variant 4 | b | a |
| Variant 5 | b | b |
| Variant 6 | b | c |
| Variant 7 | c | a |
| Variant 8 | c | b |
| Variant 9 | c | c |

The blocking ability of the humanized antibodies: The ability of the humanized antibodies to block the binding hPD-1 to hPD-L1 was measured. 100 ng of hPD1 mIg were pre-incubated with different dose of humanized antibodies in 10 μl of PBS for 30 min at 4° C. then used to stain CHO/hB7-H1 cells. The cells were washed and further stained with goat anti mIgG-APC. The blocking effect was assessed with flow cytometry. Using a similar method, the ability of the humanized antibodies to block the binding hPD-1 to hPD-L2 was measured.

Figure 9:
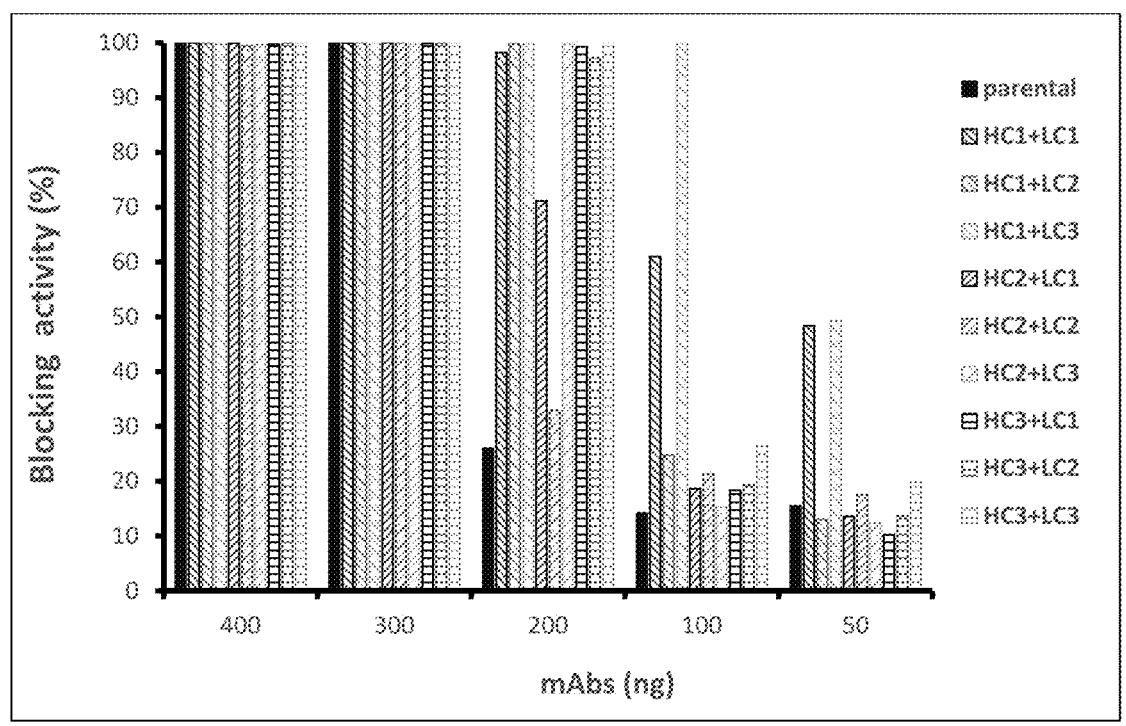
FIG. 9 shows that humanized antibodies can have a blocking effect on the binding ability of PD-1 to PD-L1.
Figure 10:
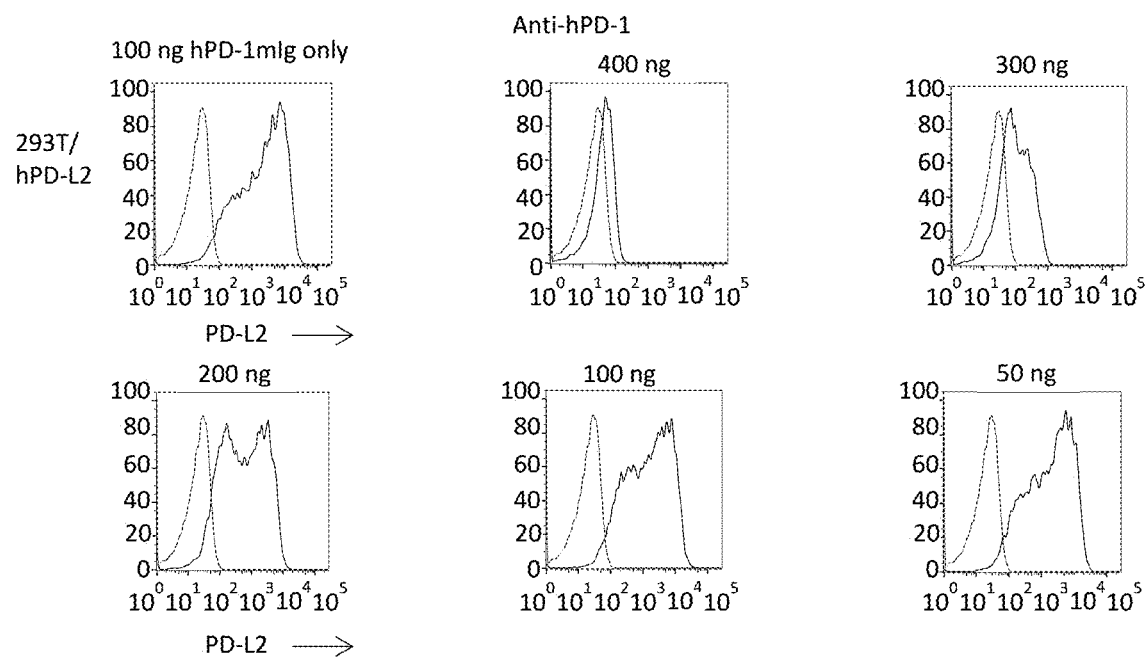
FIG. 10 shows that humanized antibodies can have a blocking effect on the binding ability of PD-1 to PD-L2.
Figure 10:
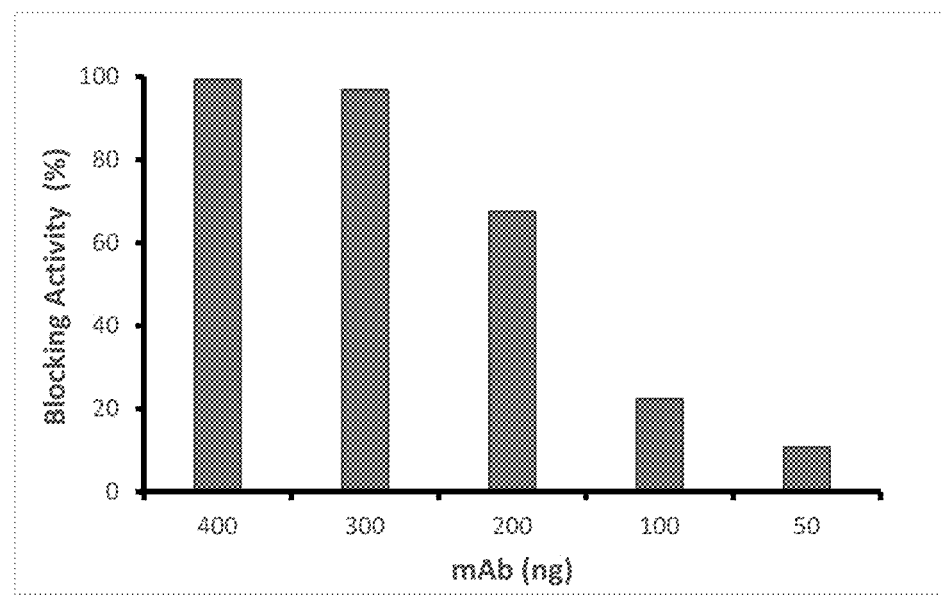

The results showed that binding of hPD-1 mIg to CHO/hPD-L1 cells was inhibited in a dose-dependent manner by all the humanized antibodies. Some mutant combinations have higher blocking capacity than chimeric parental antibody (FIG. 9). The results also showed that the binding of hPD-1 mIg to CHO/hPD-L2 cells was also blocked (FIG. 10).

Binding affinity and kinetics determination of the humanized antibodies: The binding affinity and kinetics of the humanized PD-1 mAbs interact with hPD-1 protein was assessed with Biacore T100 (GE Healthcare Life Sciences). The hPD-1 mIg proteins were immobilized on the sensor chip CM5 by amine coupling. The filtrated humanized antibodies were diluted with HBS-EP Buffer pH7.4 (GE Healthcare Life Sciences) and subsequently injected over the hPD-1 mIg-immobilized surface. Nine different concentrations were tested for each sample. Detailed binding kinetic parameters (association rate, Ka, dissociation rate, Kd, and affinity constant, KD) can be determined by full kinetic analysis.

The analysis data showed that there was no significant difference in the binding rate (Ka) between the mutant combinations and the chimeric parental antibody. Three mutant combinations (3, 6,9) were close to the chimeric parental antibody at the dissociation rate (Kd). All the humanized antibodies have strong affinity with KD values in the low nanomolar range ($10^{-10}$ M). Two mutant combinations (3, 6) KD values closed to the chimeric parental antibody ($9.89 \times 10^{-11}$ M) (Table 4).

TABLE 4

Binding affinity and kinetics determination of the humanized antibodies

| | ka (1/Ms) | Kd (1/s) | KD (M) |
|---|---|---|---|
| Parental | 2.88E+05 | 2.85E−05 | 9.89E−11 |
| Variant 1 | 2.10E+05 | 6.15E−05 | 2.93E−10 |
| Variant 2 | 2.10E+05 | 7.64E−05 | 3.63E−10 |
| Variant 3 | 2.42E+05 | 2.33E−05 | 9.63E−11 |
| Variant 4 | 1.19E+05 | 6.29E−05 | 3.38E−10 |
| Variant 5 | 2.11E+05 | 6.94E−05 | 3.29E−10 |
| Variant 6 | 2.48E+05 | 2.23E−05 | 8.98E−11 |
| Variant 7 | 2.18E+05 | 6.48E−05 | 2.91E−10 |
| Variant 8 | 2.22E+05 | 7.95E−05 | 3.58E−10 |
| Variant 9 | 2.59E+05 | 3.20E−05 | 1.23E−10 |

Enhancing effect of anti-PD-1 on allo $CD8^+CTL$ killingPD-L1 positive tumor cells in vitro: Based on the anti-tumor mechanism of anti-PD-1 antibody, this example designed an in vitro model to determine the enhancing effect of anti-PD-1 antibodies to tumor cell killing by human allogeneic CD8+ cytotoxic lymphocytes (allo $CD8^+$ CTL). Firstly, the $CD8^+$ lymphocytes were isolated from human PBMC and cultured with irradiated human melanoma transfected hB7-1 cells (624 Mel/B7-1) to produce allo$CD8^+$cyto CTL. Then allo $CD8^+$ CTL cells were co-cultured with overnight-cultured 624 Mel/hPD-L1 tumor cells in a 96-well plate for 5 days in the presence of humanized antibodies or control Ig. The cells in plate wells were stained with 0.5% crystal violet and the plate was read with ELISA reader at 540 nm. The killing activity was calculated based on the survival of the tumor cells.

$$\% \text{ Cytotoxicity} = \frac{\text{Absorbance of 100\% viable cell control wells} - \text{absorbance of test wells}}{\text{Absorbance of 100\% viable cell control wells}} \times 100$$

Figure 11:
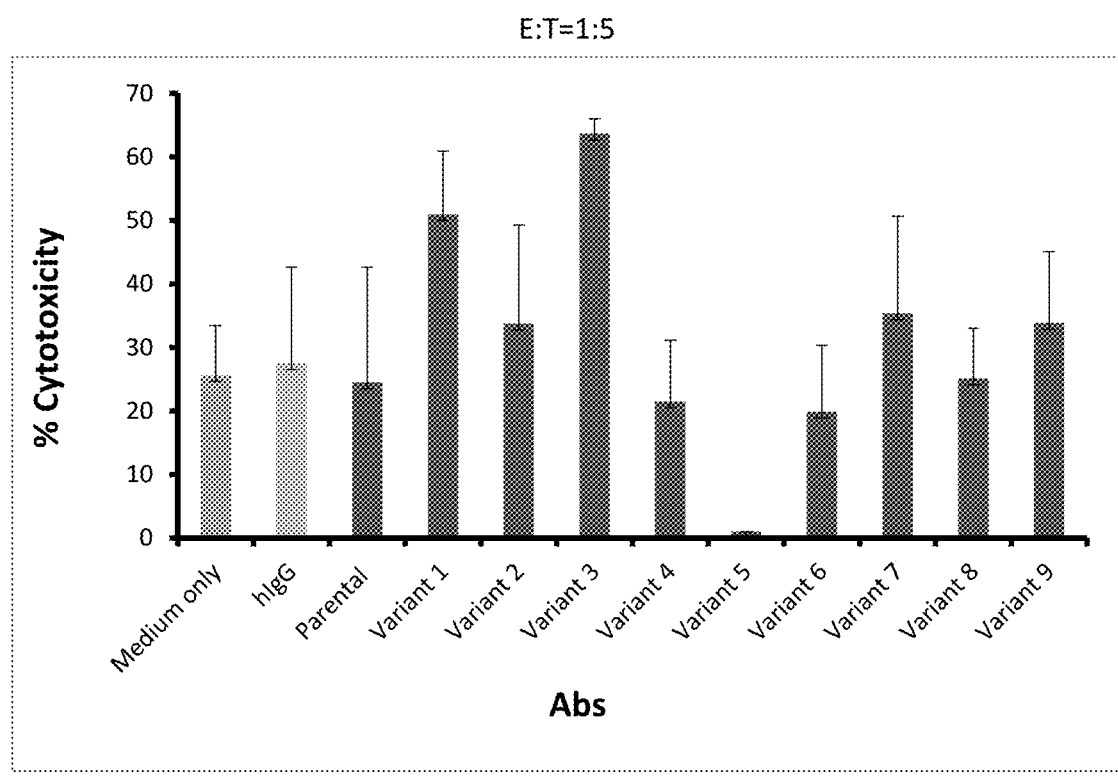
FIG. 11 shows that humanized mAbs augment cytotoxicity of allo CD8+ CTL cells against cancer cells in vitro.

The results demonstrated that some mutant combinations could enhance the ability of allo CTL cells killing tumor cells in vitro (FIG. 11).

The best set of mutant combinations (Variant 3) was selected and the protein coding sequences were cloned into suitable expression vectors and were transferred into CHO cells to product anti-hPD-1 antibody that is referred to also as TY101.

Example 5

The Characteristics of TY101 in Cancer Immunotherapy

Cytokine-enhanced mixed lymphocyte reaction (MRL) in PBMC. Human peripheral bloodmononuclear cells (PBMCs) from healthy individuals were isolated by density gradient centrifugation using the Ficoll-Hypaque. PBMCs from healthy donor 1 were irradiated with X-rays at doses of 40 Gy as stimulator cells. T lymphocytes were isolated with human Pan T cell Isolation Kit (MiltenylBiotec) from healthy donor 2 as responder cells. Responder cells and stimulator cells were resuspended in complete RPMI media containing 10% FCS and seeded $2.5 \times 10^5$ responder cells and $1.25 \times 10^5$ stimulator cells (R/S=2) per wellinto 96-well plate in the presence of serial dilutions of TY101 or hIgG control. The cells were cultured at 37° C. for 5 days in a humidified incubator with 5% CO2. Proliferative activity of T cells was assessed by Cell Counting Kit-8 (Dojindo Molecular Technologies, Inc) on day 5. To detect cytokines, culture supernatants were collected on day 3 and day 5. Cytokine analysis was performed using the Human Th1/Th2/Th17 Cytometric Bead Array kit (CBA; BD Biosciences).

Figure 12:
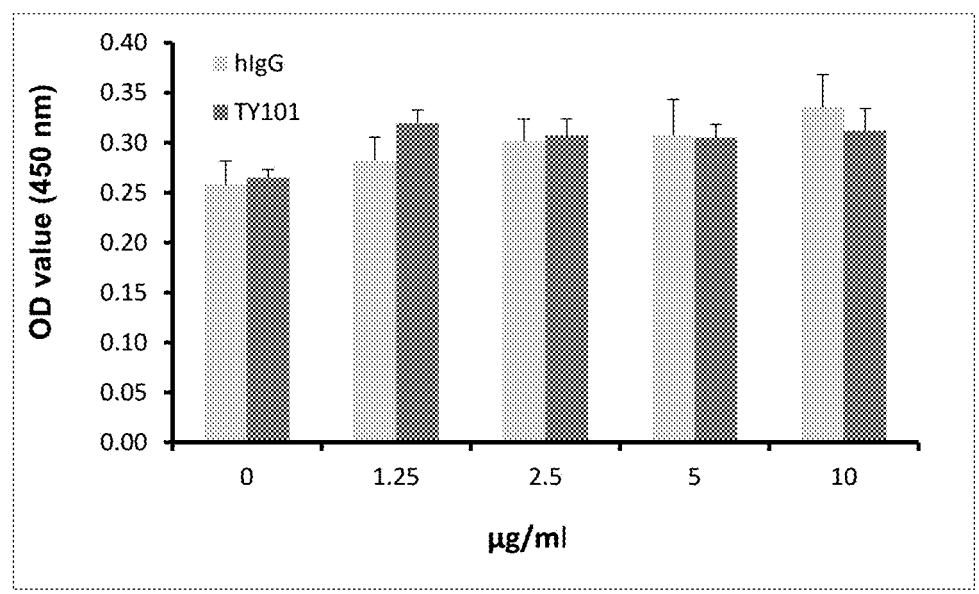
FIG. 12 shows proliferative response of MLR to anti-hPD-1 antibodies.
Figure 13:
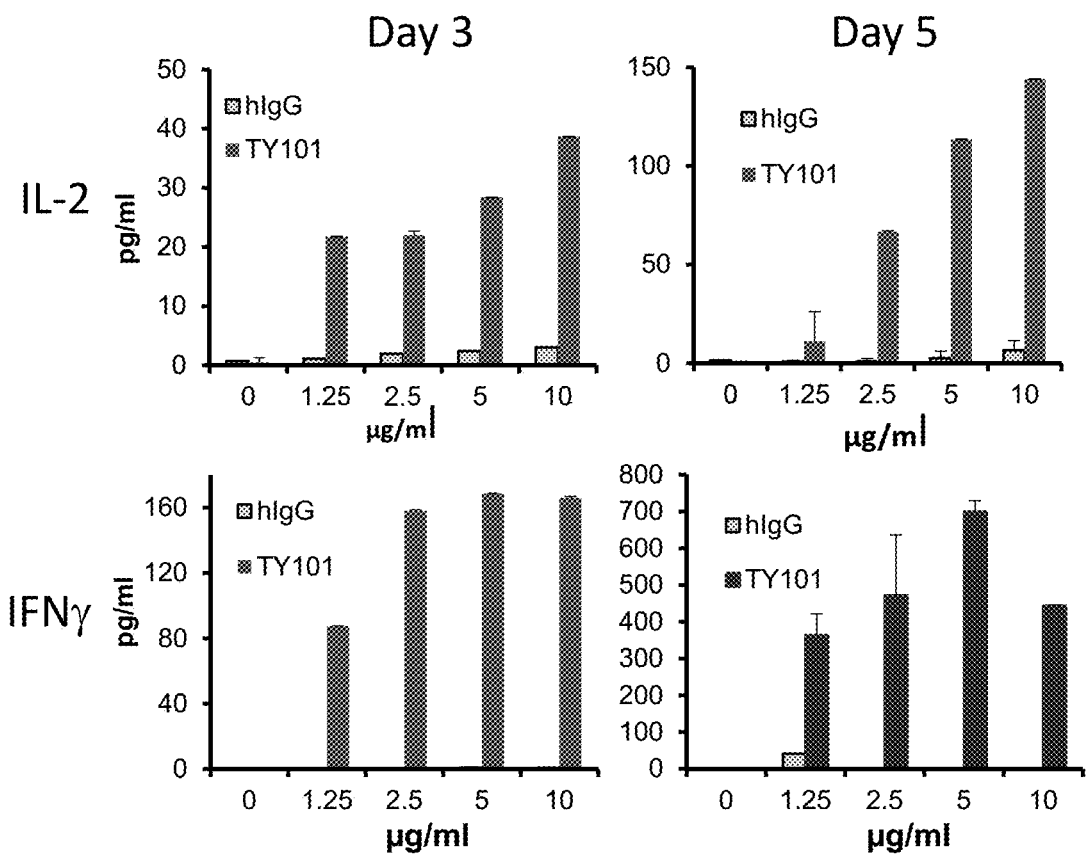
FIG. 13 shows IL-2 and IFNγ expression profile in MLR culture supernatants.

The results demonstrated that T cells proliferative response upon to TY101 was similar to hIgG (FIG. 12). Interestingly, the cytokines IL-2 and IFNγ production was significantly increased in the culture supernatant of MLR administered with TY 101 compared to with hIgG (FIG. 13).

Blocking the expression of PD-1 on T lymphocytes. The expression of PD-L1 on tumor cells can induce PD-1 expression on tumor-infiltrating lymphocytes (TIL) in tumor microenvironment and trigger PD-1-dependent immune suppression. This example designed an in vitro model to determine if TY101 can inhibit the hPD-1 expression on human lymphocyte when culture with hPD-L1 transfected tumor cells. Human T lymphocytes isolated from human PBMC were cultured with human melanoma transfected hPD-L1 (624/hPD-L1) cells in the presence of 10 μg/ml of TY101 or control IgG for 4 days. The expression of hPD-1 on lymphocytes was detected by flow cytometry.

Figure 14:
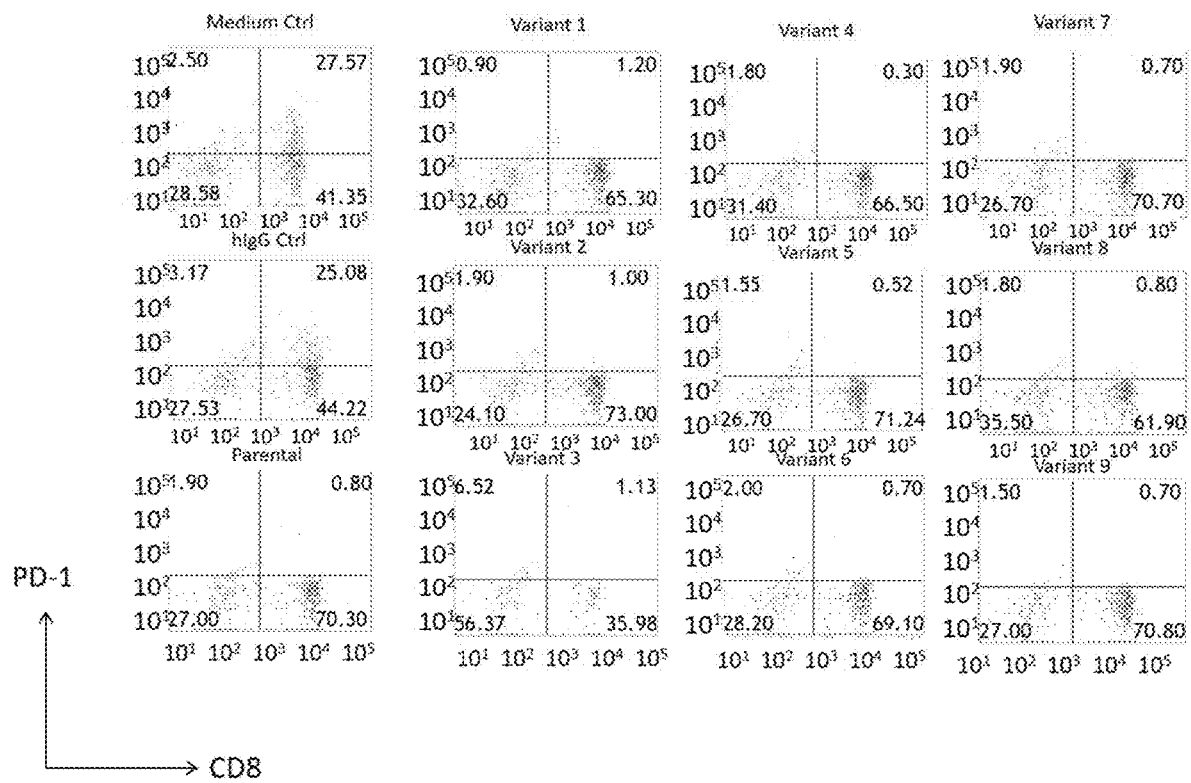
FIG. 14 shows that the expression of PD-L1 on lymphocytes was inhibited by PD-1 mAbs.

The results demonstrated that expression of PD-1 on lymphocytes was completely inhibited by the addition of TY101 compared to medium only and hIgG control (FIG. 14).

In vivo antitumor activity of humanized PD-1 antibody: The in vivo antitumor effect of TY101 was investigated. 8-week-old female human PD-1 knock-in mice (purchased from Shanghai Model Organisms Center, Inc.) were implanted subcutaneously (s.c) at right flank with MC38 transfected hPD-L1 (MC38/hPD-L1) tumor cells ($1 \times 10^6$/mouse) on day 0. TY101 or control Ig was administered (10 mg/kg) via i.p. injection on day 6, day 9 and day 13. The tumor size and survival were monitored.

Figure 15:
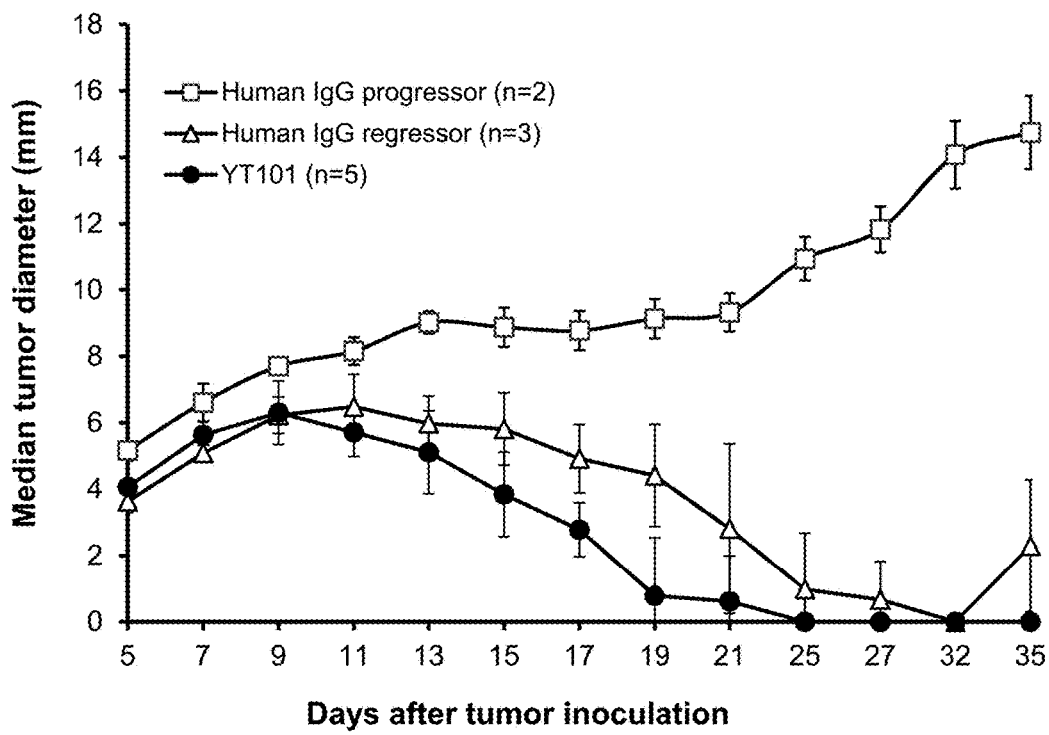
FIG. 15 shows in vivo antitumor activity of humanized PD-1 antibody.

All animals initially had detectable tumor (4-5 mm by day 6). However, after treatment of mice bearing MC38/hPD-L1 tumors with TY101, a complete response occurred in 100% of the mice. Tumors in all five mice treated with TY101 were regressed completely by day 25. In contrast, two of five mice treated control IgG developed progressively growing tumors. In another three mice treated control IgG, although tumors were also regressed on day 32, tumors in two mice were relapsed soon (FIG. 15). The results indicated that TY101 can enhance the antitumor efficacyin vivo.

Example 6

A Comparison of Functions of TY101 to Commercial PD-1 Antibodies

This example selected two anti-hPD-1 antibodies that are currently approved for clinical treatment of cancer patients for comparison with TY101: Merck's Keytruda (pembrolizumab) and Bristol-Myers Squibb's Opdivo (nivolumab).

Figure 16:
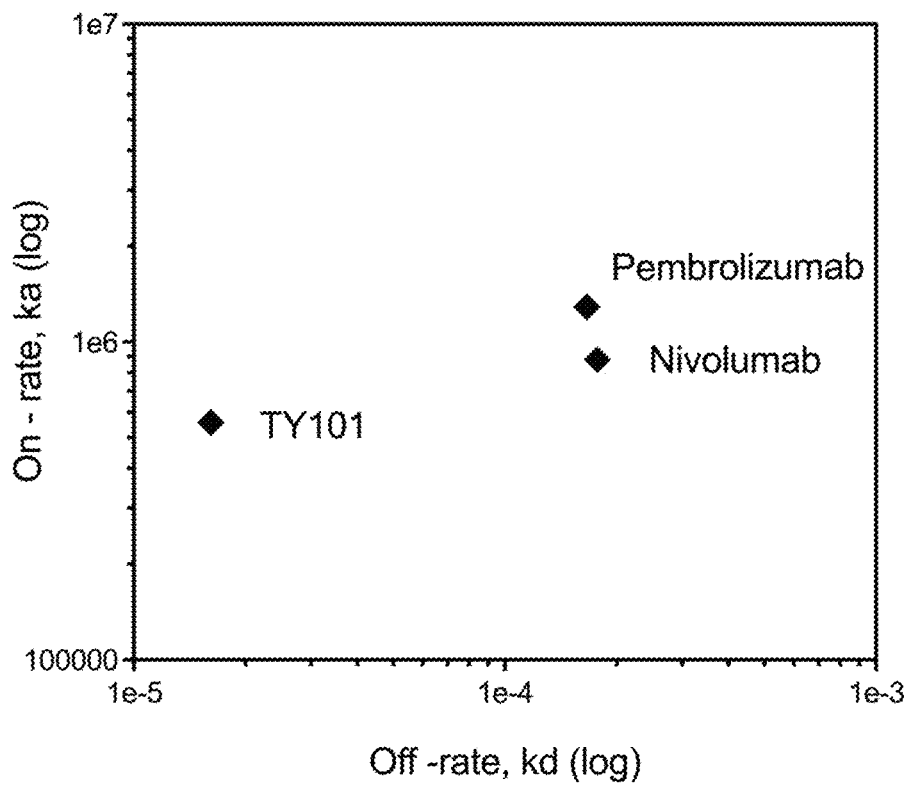
FIG. 16 presents a comparison of the antibodies binding affinity and kinetics.

Antibody binding affinity and kinetics: The affinity and kinetics of the TY101 was analyzed using the Biacore T200 instrument (GE Healthcare Life Sciences) and compared with two commercial antibodies. The hPD-1 mIg proteins were immobilized with low concentration (33RU) on the sensor chip CMS, the antibodies as an analyte (mobile phase) to detect the interaction. The data showed that the binding rates Ka of three antibodies are not significantly different. TY101 is slightly lower than the commercial antibodies. Dissociation rate Kd of TY101 is 10 times slower than two commercial antibodies and affinity KD of TY101 is 4-7 times stronger than commercial antibodies. The results indicated that TY101 is indicative of a stronger binding (FIG. 16).

Comparison of PD-1 Antibodies in PD-1/PD-L1 Blockade: The PD-1/PD-L1 blockade bioassay was assayed using PD-1/PD-L1 Blockade Bioassays Kit (Promega). Jurkat-PD1 cells at $1 \times 10^5$ cells/well were stimulated with overnight-cultured CHO-PD-L1 cells (culture started at $5 \times 10^4$ cells/well) in an opaque 96-well TC plate for 5 hours in the presence of serial dilutions (0-30 μg/ml) of TY101, Pembrolizumab, Nivolumab, or negative Ctrl hIgG4. After 5 hours of incubation, Jurkat-PD-1 cell activation was detected by measuring luciferase activity with ONE-Glo substrate (Promega) for relative light units (RLU) on a SpectraMAX L luminometer.

Figure 17:
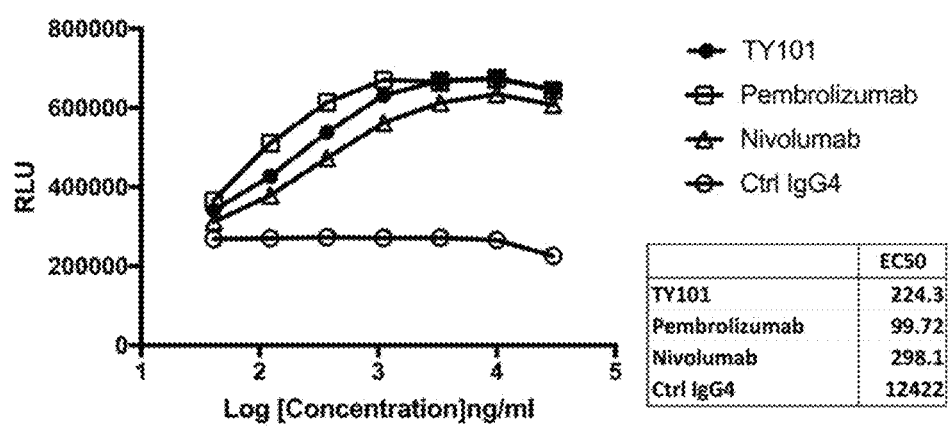
FIG. 17 shows comparison of PD-1 antibodies in PD-1/PD-L1 blockade.

The analysis data showed TY101 and two commercial antibodies can block the PD-1/PD-L1 path way. The block effect of TY101 is similar to that of Pembrolizumab and better than that of Nivolumab (FIG. 17).

Comparison of inhibitory effects of tumor cells growth in vitro: As described previously, allo CD8+ CTL cells were co-cultured with overnight-cultured 624 Mel/PD-L1 tumor cells in a 96-well plate for 5 days in the presence of different mAbs and control IgG. The cells were stained with 0.5% crystal violet and the plate was read with ELISA reader at 540 nm. The killing activity was calculated based on the survival of the tumor cells.

Figure 18:
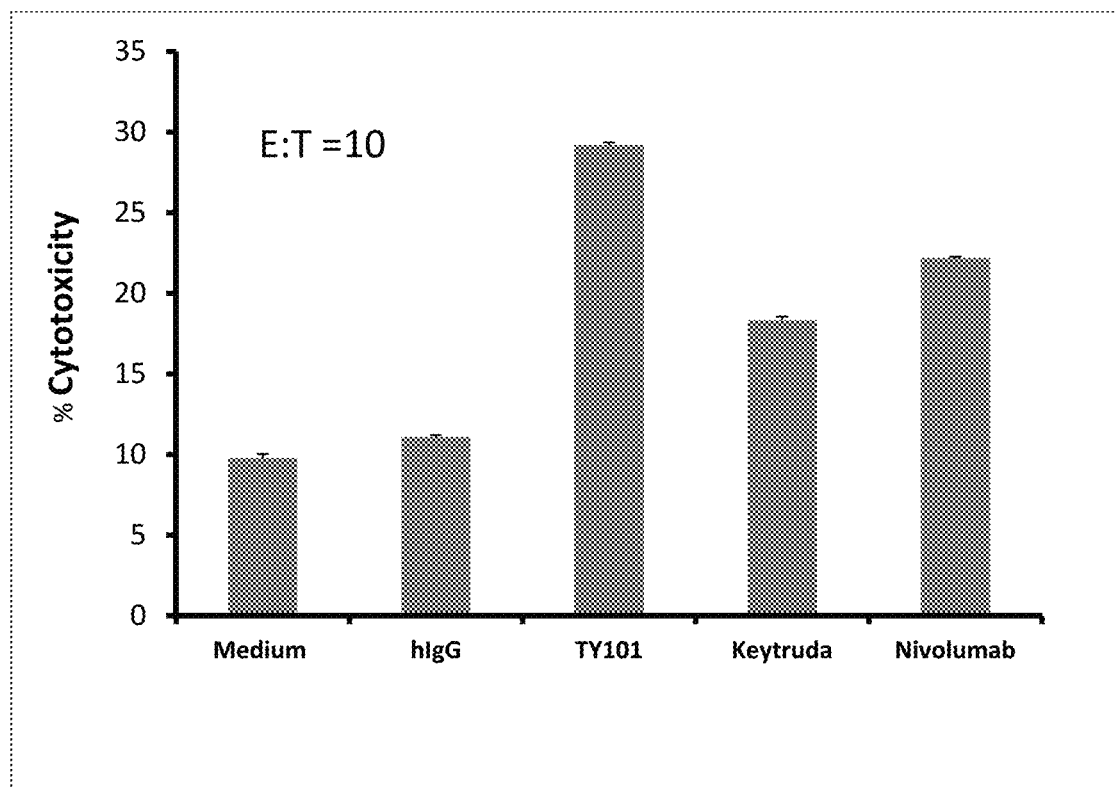
FIG. 18 shows comparison of mAbs to augment cytotoxicity of allo CD8+ CTL cells against cancer cells in vitro.

The results showed that all three anti-PD-1 mAbs were able to enhance the tumor killing ability of the allo CD8+ CTL. The enhance effect of TY101 was higher than that of two commercial antibodies (FIG. 18).

Example 7

Development Clones for TY101 and Their Activities

The sequence of TY101 was cloned into proprietary expression vectors and transfected CHO cells. Monoclonal cell lines were established by using ClonePix and/or limiting dilution. Multiple clones were established and antibodies produced by 3 such clones (TY101-01-09, TY101-04-T3-05 and TY101-4G1) were characterized.

Test Antibodies Binding Against hPD-1 or mPD-1 Proteins (ELISA)

Figure 19:
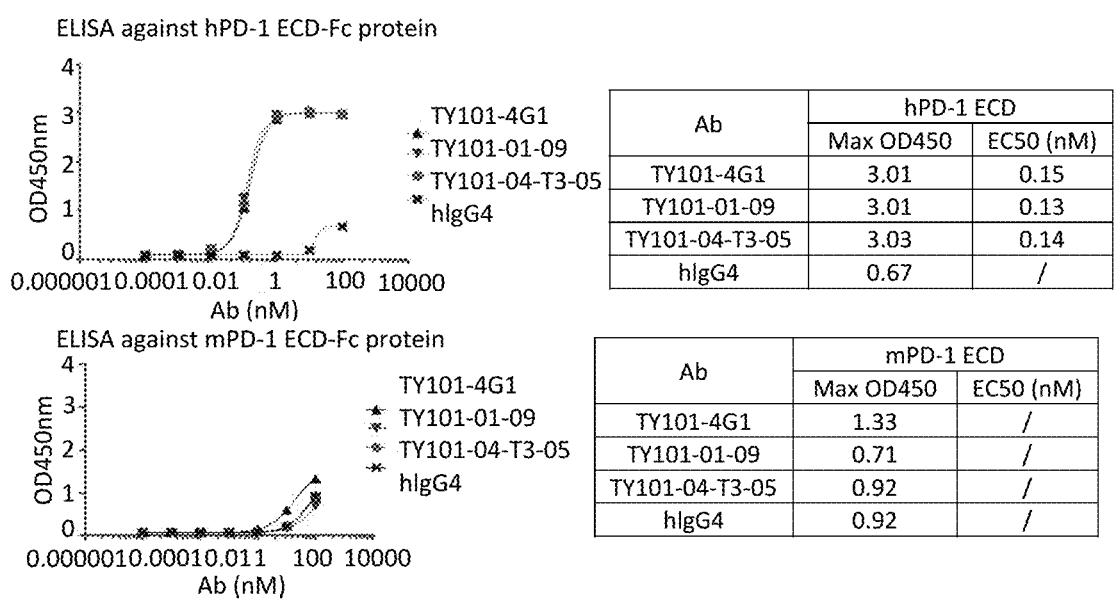
FIG. 19 shows test articles' binding to hPD-1 or mPD-1 (ELISA assays).

The bindings of the antibodies to hPD-1 and the cross-reactivity to mPD-1 proteins were tested by ELISA. A serial dilution of test antibodies were added to ELISA plates pre-coated with 1 μg/ml hPD-1 or mPD-1. HRP conjugated goat anti-human IgG or goat anti-mouse IgG antibody was then added, followed by the addition of substrate Tetramethylbenzidine (TMB) and quantification with a SpectraMax Plus 384 Microplate Reader (Molecular Device, LLC., Sunnyvale, Calif.) at 450 nm wavelength. TY101 clones tested TY101-01-09, TY101-04-T3-05 and TY101-4G1 showed good binding to hPD-1 protein with EC50s in the range of 0.01-0.15 nM. The antibodies did not exhibit binding to mPD-1 protein (FIG. 19).

Test Antibodies Binding to hPD-1 and cPD-1 Expressing CHOK1 Cells (Flow Cytometry)

Figure 20:
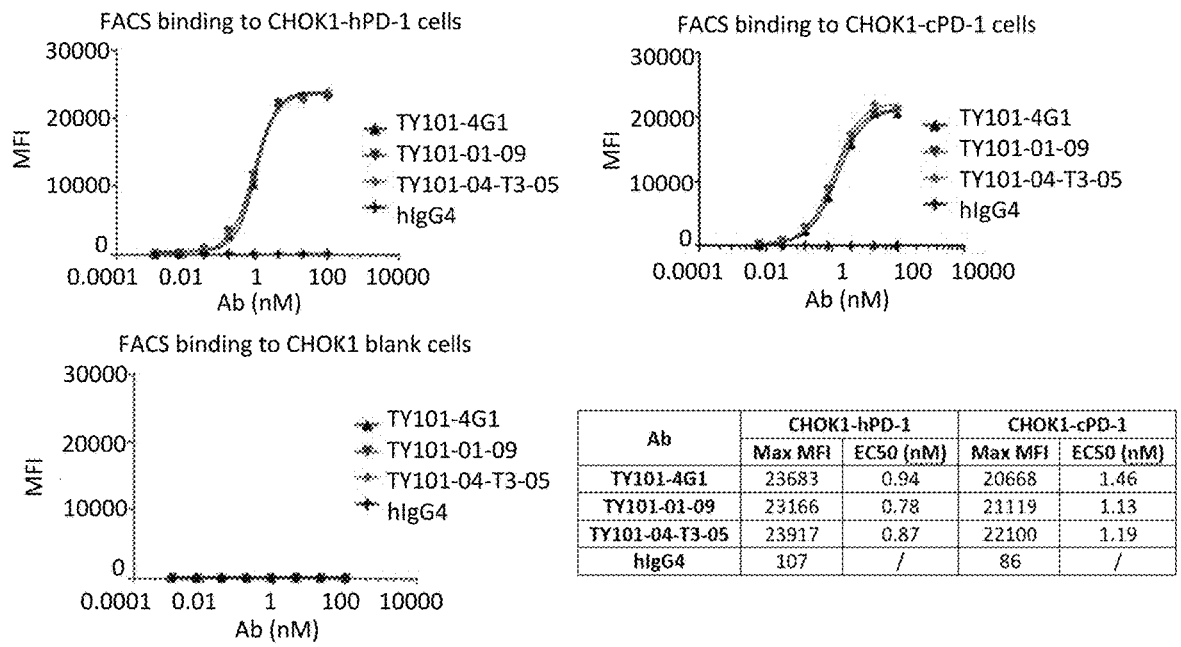
FIG. 20 shows test articles' binding against hPD-1- or cPD-1-expressing CHOK1 cells using flow cytometry.

The bindings of the antibodies to hPD-1 and cross-reactivity to cynomolgus monkey PD-1 (cPD-1) were tested using hPD-1 or cPD-1 expressing CHOK1 cells by flow cytometry. CHOK1-hPD-1, CHOK1-cPD-1 and CHOK1 blank cells were incubated with a serial dilution of test articles followed by Alexa Fluor® 488 conjugated goat anti-human IgG (H+L) antibody, and analyzed using a FACSCanto II (BD Biosciences, San Jose, Calif.). TY101 clones tested TY101-01-09, TY101-04-T3-05 and TY101-4G1 showed good binding to CHOK1-hPD-1 with sub-nanomolar EC50s and to CHOK1-cPD-1 cells with single digit nanomolar EC50s (FIG. 20).

Test Antibodies Blocking Activity on hPD-1/hPD-L1 or hPD-1/hPD-L2 Binding (Flow Cytometry)

Figure 21:
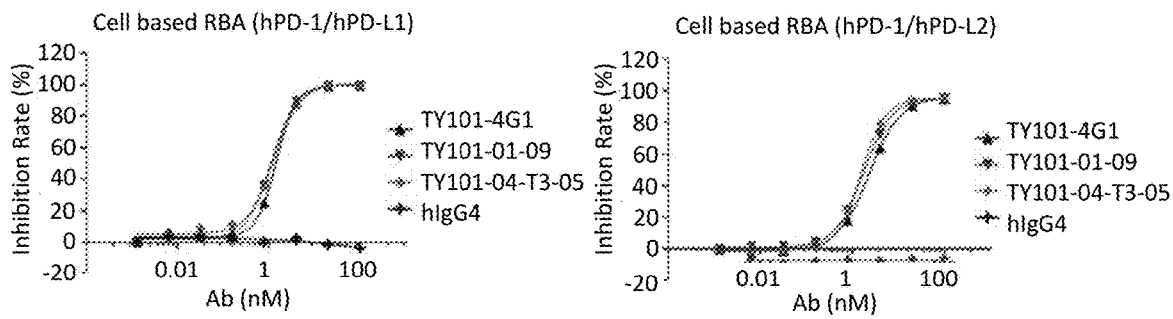
FIG. 21 shows the blocking activities of test articles on hPD-L1 (left) and hPD-L2 (right) binding to hPD-1-expressing CHOK1 cells.

These antibodies were further tested for their abilities to block hPD-1/hPD-L1 as well as hPD-1/hPD-L2 binding, which would be the key for potential effectiveness in cancer patient treatments. CHOK1-hPD-1 cells were incubated with a serial dilution of test articles mixed with Biotin-hPD-L1 or Biotin-hPD-L2. The cells were then incubated with Alexa 488 labeled Streptavidin and analyzed using a FACSCanto II. Anti-hPD-1 antibodies TY101-01-09, TY101-04-T3-05 and TY101-4G1 blocked the binding of hPD-L1 to hPD-1-expressing CHOK1 cells with 1.15-1.47 nM IC50s. They also blocked hPD-L2 binding to hPD-1-expressing CHOK1 cells with 1.52-2.33 nM IC50s (FIG. 21).

Figure 22:
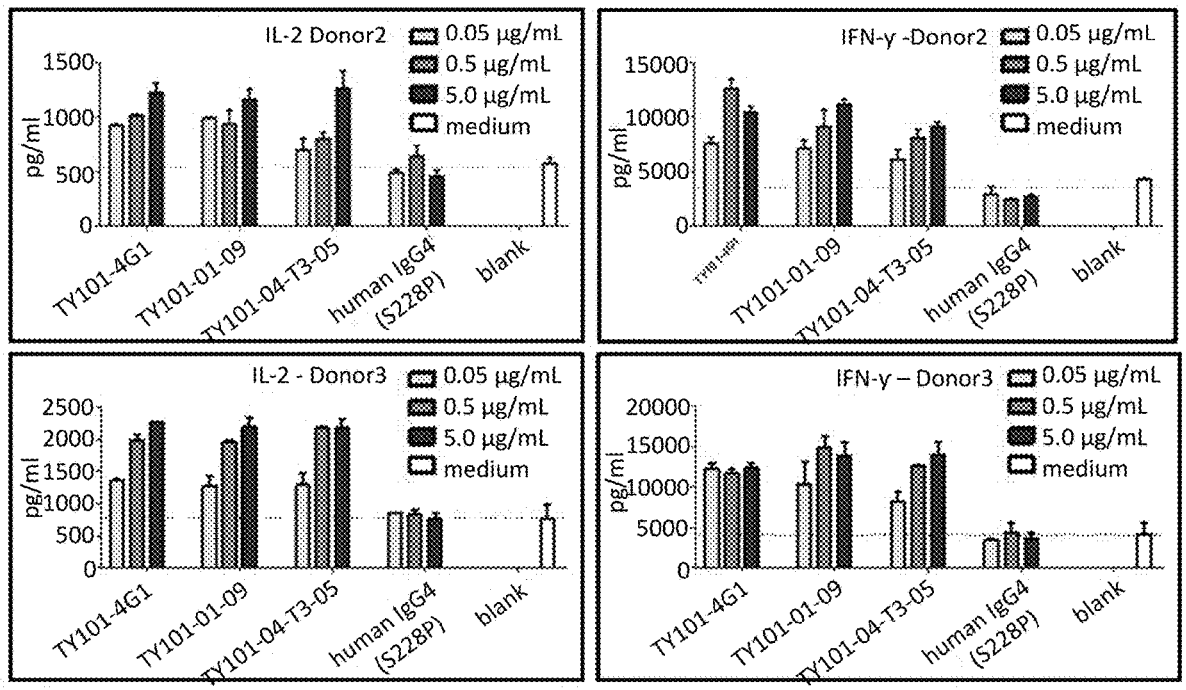
FIG. 22 shows IL-2 (left) and IFN-γ (right) levels in human MLR assays.

Human mixed leukocyte reaction (MLR) assay to test the effect of antibodies on T cells The effects of these antibodies on T cell functions were tested in human MLR assays with T cells isolated from 2 donors. Adherent PBMCs (mostly monocytes; isolated from donor 1 and plated in cell culture dish to allow to adhere) were cultured in the presence of 100 ng/mL of recombinant human (rh) GM-CSF and 50 ng/mL of rhIL-4 for 5 days with half volume of medium refreshed after 3 days and 1 µg/mL LPS added on day 6. At day 7, the resulting cells (mostly mature DCs) were harvested and treated with mitomycin C. CD3+ T cells were isolated from donors 2 and 3 by Easy-Sep™ Human T Cell Isolation Kit (negative selection, STEMCELL Technologies). DCs and T cells were co-cultured in the presence of 3 concentrations (5, 0.5, 0.05 µg/ml) of test antibodies for 5 days. The supernatants were harvested after 3 days to determine IL-2 levels and after 5 days (100 µL) to determine IFN-γ levels. Anti-hPD-1 antibodies TY101-01-09, TY101-04-T3-05 and TY101-4G1 promoted the secretion of IL-2 and IFN-γ by cells from both donors in a dose-dependent manner when compared to isotype control hIgG4 (FIG. 22).

Figure 23:
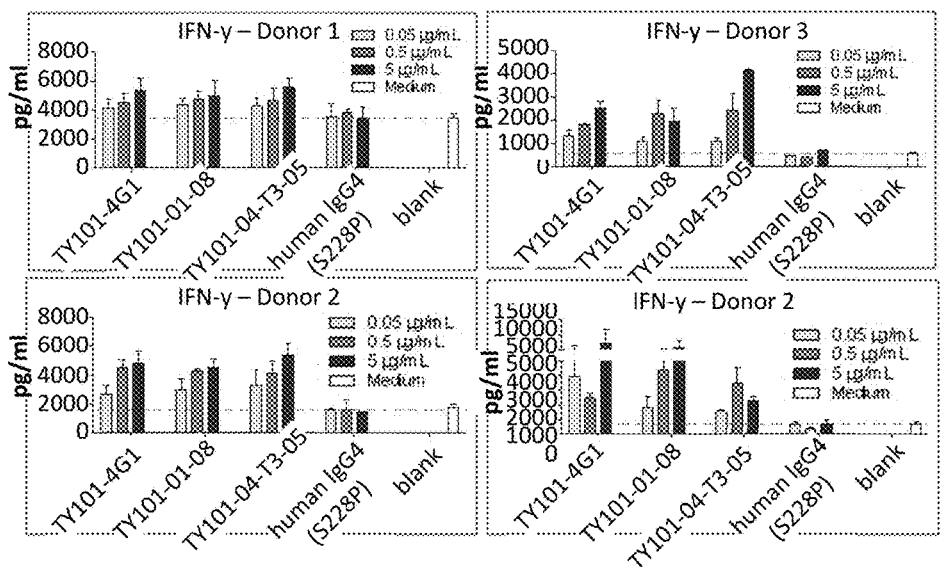
FIG. 23 shows IFN-γ levels in engineered tumor and T cell co-culture assays.

Engineered Tumor Cell-Human T cell Coculture Assay to Test the Effect of Antibodies on T Cells The effects of these antibodies on T cell functions were also tested in engineered tumor cell-human T cell co-culture assay using T cells isolated from 4 different donors. CD3+ T cells were isolated from PBMCs of the 4 donors by Easy-Sep™ Human T Cell Isolation Kit. Engineered tumor cells Hep3B-OS8-hPDL1, which are Hep3B cells (KCLB, catalog #: 88064) engineered to stably express 0S8 (anti-CD3 single chain variable fragment (scFv)) as well as hPD-L1, were treated with mitomycin C and co-cultured with CD3+ T cells in the presence of 3 concentrations (5, 0.5, 0.05 µg/ml) of test antibodies for 3 days and culture supernatants were harvested to determine IFN-γ levels. Anti-hPD-1 antibodies TY101-01-09, TY101-04-T3-05 and TY101-4G1 promoted the secretion of IFN-γ by cells from all 4 donors in a dose-dependent manner when compared to isotype control hIgG4 (FIG. 23).

Example 8

Figure 24:
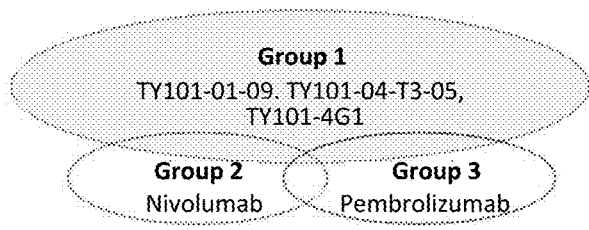
FIG. 24 shows epitope binding by ELISA results (upper panel) and schematics on epitope overlaps of different test articles (lower panel).

TY101 Clones Showed Better Binding Affinities Compared to FDA Approved Anti-hPD-1 Antibodies Competitive ELISA to Test Antibody Epitope Overlaps Whether these antibodies bind to the same epitopes as the FDA approved anti-hPD-1 antibodies Nivolumab or Pembrolizumab were tested in a competitive ELISA assay. A serial dilution of competing antibodies and Biotin-hPD-1 were added to ELISA plates pre-coated with 1 µg/ml a test antibody. HRP conjugated streptavidin was then added, followed by the addition of substrate TMB and quantification with a SpectraMax Plus 384 Microplate Reader at 450 nm wavelength. Anti-hPD-1 antibodies TY101-01-09, TY101-04-T3-05 and TY101-4G1 almost completely blocked the binding of each other to hPD-1, suggests they shared similar epitopes. The 3 antibodies also blocked the binding of Nivolumab and Pembrolizumab to hPD-1 nearly completely (93% to 94%), while Nivolumab and Pembrolizumab only partially blocked the binding of these antibodies to hPD-1 (77%-78% for Nivolumab and 46%-49% for Pembrolizumab). These data suggest that TY101-01-09, TY101-04-T3-05 and TY101-4G1 antibodies bind to epitopes different from those of Nivolumab and Pembrolizumab, and they may have higher affinity to hPD-1 than Nivolumab and Pembrolizumab (FIG. 24).

Binding Affinity of Test Antibodies to hPD-1 Determined by SPR

Figure 25:
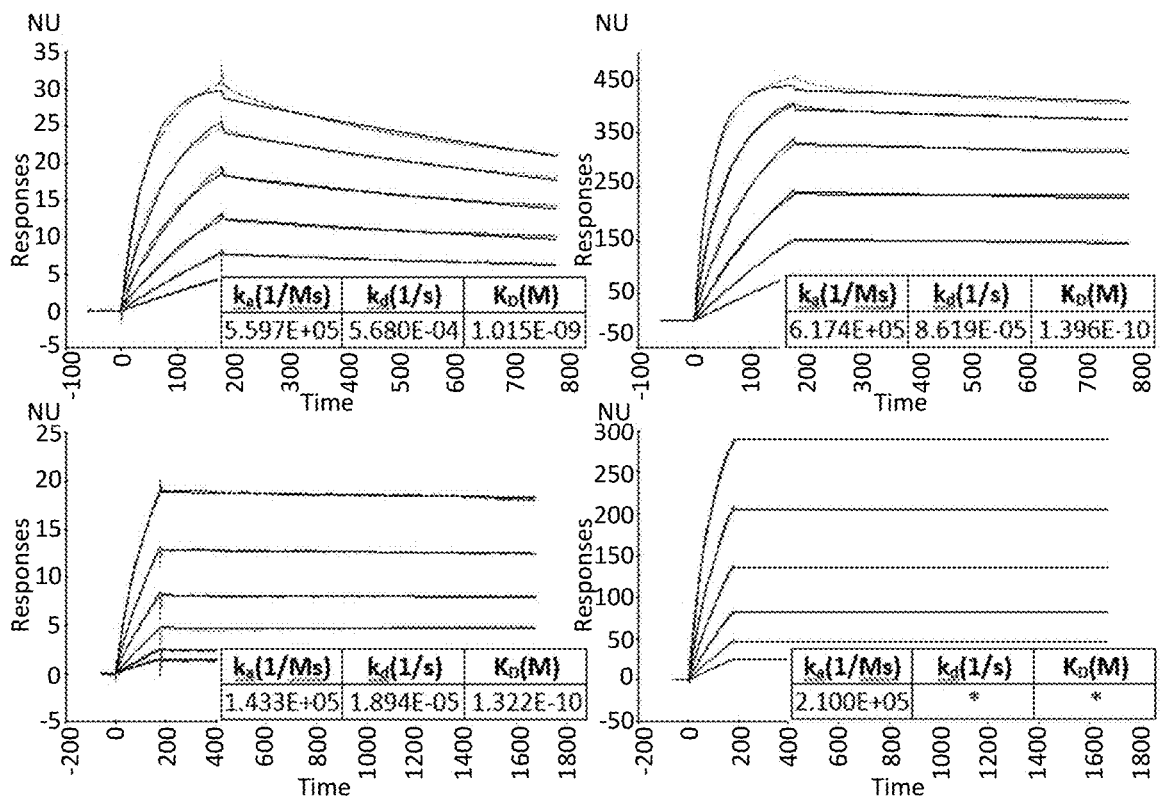
FIG. 25 shows the binding of Nivolumab (upper panels) or TY101-04-T3-05 (lower panels) antibodies to a recombinant hPD-1 at the low immobilization level (60 RU, left panels) and high immobilization level (960 RU, right panels).

To get an accurate measurement of the binding affinities to hPD-1, antibodies TY101-01-09, TY101-04-T3-05 and TY101-4G1 as well as Nivolumab and Pembrolizumab were analyzed with SPR. Human PD-1 ECD protein was immobilized on CM5 sensor chip for different length of time to achieve low immobilization level (at 60 RU) in flow cell 3 and high immobilization level (960 RU) in flow cell 4. Serially diluted (0, 1.5625, 3.125, 6.25, 12.5, 25 and 50 nM) antibodies were injected into flow cells. The association time were 180s and dissociation time were 600 s (for Nivolumab and Pembrolizumab) or 1500 s (for TY101-01-09, TY101-04-T3-05 and TY101-4G1). After signals of both the reference (flow cell 1) and the zero concentrations being subtracted from that of samples, binding kinetics was calculated using Biacore T200 evaluation software version 1.0 and a 1:1 binding model for curve fitting. There was no binding of control human IgG4 to the hPD-1. Based on data from the low immobilization level of hPD-1 (~60 RU; Table 3; FIG. 23), the rates of association to human PD-1 by anti-hPD-1 antibodies TY101-01-09, TY101-04-T3-05 and TY101-4G1 was slightly lower than those of Nivolumab and Pembrolizumab (by 2-4 folds). The rates of dissociation from human PD-1 of these 3 antibodies were slower than those of Nivolumab and Pembrolizumab by 12 to 30 folds, resulting in their affinity 4-8 folds better than those of Nivolumab and Pembrolizumab (lower KD corresponds to better affinity, and vice versa; Table 3). The binding affinities of anti-hPD-1 antibodies TY101-01-09, TY101-04-T3-05 and TY101-4G1 to hPD-1 were also tested at high immobilization level of hPD-1. Antibodies TY101-01-09, TY101-04-T3-05 and TY101-4G1 showed very slow disassociation rates with minimal disassociation observed even after 1500 s of disassociation time (FIG. 23). The data suggested the binding affinities of TY101-01-09, TY101-04-T3-05 and TY101-4G1 were better than those of Nivolumab and Pembrolizumab, mostly due to slow disassociation rate (FIG. 25).

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference

What is claimed is:

1. A method of treating a cancer in an individual in need thereof, comprising administering to the individual a composition comprising an effective amount of antibody or fragment thereof that specifically binds to PD-1,
  wherein the antibody or fragment thereof comprises a heavy chain variable region comprising heavy chain complementarity determining regions HCDR1, HCDR2, and HCDR3, and a light chain variable region comprising light chain complementarity determining regions LCDR1, LCDR2, and LCDR3, wherein the HCDR1, HCDR2, HCDR3, LCDR1, LCDR2, and LCDR3 are selected from the group consisting of:
  (a) HCDR1: GFTFSSYT (SEQ ID NO: 1), HCDR2: ISHGGGDT (SEQ ID NO: 2), HCDR3: ARHSGYER-GYYYVMDY (SEQ ID NO: 3), LCDR1: ESVDYYGFSF (SEQ ID NO: 4), LCDR2: AAS (SEQ ID NO: 5), LCDR3: QQSKEVPW (SEQ ID NO: 6);
  (b) HCDR1: GYTFTSYT (SEQ ID NO: 7), HCDR2: INPTTGYT (SEQ ID NO: 8), HCDR3: ARDDAYYSGY (SEQ ID NO: 9), LCDR1: ENIYSNL (SEQ ID NO: 10), LCDR2: AAK (SEQ ID NO: 11), LCDR3: QHFWGTPWT (SEQ ID NO: 12); and
  (c) HCDR1: GFAFSSYD (SEQ ID NO: 13), HCDR2: ITIGGGTT (SEQ ID NO: 14), HCDR3: ARHRYDYFAMDN (SEQ ID NO: 15), LCDR1: ENVDNYGINF (SEQ ID NO: 16), LCDR2: VSS (SEQ ID NO: 17), LCDR3: QQSKDVPW (SEQ ID NO: 18).

2. The method of claim 1, wherein the antibody or fragment thereof comprises a heavy chain constant region, a light chain constant region, an Fc region, or the combination thereof.

3. The method of claim 2, wherein the light chain constant region is a kappa or lambda chain constant region.

4. The method of claim 1, wherein the antibody or fragment thereof is of an isotype of IgG, IgM, IgA, IgE or IgD.

5. The method of claim 4, wherein the antibody or fragment thereof has an isotype of IgG1, IgG2, IgG3 or IgG4.

6. The method of claim 1, wherein the antibody or fragment thereof is a chimeric antibody or a humanized antibody.

7. The method of claim 6, wherein the antibody or fragment thereof is a humanized antibody.

8. The method of claim 1, wherein the antibody or fragment thereof comprises a heavy chain variable region comprising the amino acid sequence of SEQ ID NO: 35, SEQ ID NO: 37, or SEQ ID NO: 39, or an amino acid sequence having at least 80% sequence identity to SEQ ID NO: 35, SEQ ID NO: 37, or SEQ ID NO: 39.

9. The method of claim 1, wherein the antibody or fragment thereof comprises a light chain variable region comprising the amino acid sequence of SEQ ID NO: 41, SEQ ID NO: 43, or SEQ ID NO: 45, or an amino acid sequence having at least 80% sequence identity to SEQ ID NO: 41, SEQ ID NO: 43, or SEQ ID NO: 45.

10. The method of claim 8, wherein the antibody or fragment thereof comprises a light chain variable region comprising the amino acid sequence of SEQ ID NO: 41, SEQ ID NO: 43, or SEQ ID NO: 45, or an amino acid sequence having at least 80% sequence identity to SEQ ID NO: 41, SEQ ID NO: 43, or SEQ ID NO: 45.

11. The method of claim 1, wherein the antibody or fragment thereof comprises:
  (a) a heavy chain variable region comprising the amino acid sequence of SEQ ID NO: 35, and a light chain variable region comprising the amino acid sequence of SEQ ID NO: 41;
  (b) a heavy chain variable region comprising the amino acid sequence of SEQ ID NO: 37, and a light chain variable region comprising the amino acid sequence of SEQ ID NO: 43; or
  (c) a heavy chain variable region comprising the amino acid sequence of SEQ ID NO: 39, and a light chain variable region comprising the amino acid sequence of SEQ ID NO: 45.

12. The method of claim 1, wherein the individual is a human.

13. A method of treating an infection in an individual in need thereof, comprising administering to the individual a composition comprising an effective amount of antibody or fragment thereof that specifically binds to PD-1, wherein the antibody or fragment thereof comprises a heavy chain variable region comprising heavy chain complementarity determining regions HCDR1, HCDR2, and HCDR3, and a light chain variable region comprising light chain complementarity determining regions LCDR1, LCDR2, and LCDR3, and wherein the HCDR1, HCDR2, HCDR3, LCDR1, LCDR2, and LCDR3 are selected from the group consisting of:
  (a) HCDR1: GFTFSSYT (SEQ ID NO: 1), HCDR2: ISHGGGDT (SEQ ID NO: 2), HCDR3: ARHSGYER-GYYYVMDY (SEQ ID NO: 3), LCDR1: ESVDYYGFSF (SEQ ID NO: 4), LCDR2: AAS (SEQ ID NO: 5), LCDR3: QQSKEVPW (SEQ ID NO: 6);
  (b) HCDR1: GYTFTSYT (SEQ ID NO: 7), HCDR2: INPTTGYT (SEQ ID NO: 8), HCDR3: ARDDAYYSGY (SEQ ID NO: 9), LCDR1: ENIYSNL (SEQ ID NO: 10), LCDR2: AAK (SEQ ID NO: 11), LCDR3: QHFWGTPWT (SEQ ID NO: 12); and
  (c) HCDR1: GFAFSSYD (SEQ ID NO: 13), HCDR2: ITIGGGTT (SEQ ID NO: 14), HCDR3: ARHRYDYFAMDN (SEQ ID NO: 15), LCDR1: ENVDNYGINF (SEQ ID NO: 16), LCDR2: VSS (SEQ ID NO: 17), LCDR3: QQSKDVPW (SEQ ID NO: 18).

14. A method of treating an immune disorder in an individual in need thereof, comprising administering to the individual a composition comprising an effective amount of antibody or fragment thereof that specifically binds to PD-1, _wherein the antibody or fragment thereof comprises a heavy chain variable region comprising heavy chain complementarity determining regions HCDR1, HCDR2, and HCDR3, and a light chain variable region comprising light chain complementarity determining regions LCDR1, LCDR2, and LCDR3, and wherein the HCDR1, HCDR2, HCDR3, LCDR1, LCDR2, and LCDR3 are selected from the group consisting of:

(a) HCDR1: GFTFSSYT (SEQ ID NO: 1), HCDR2: ISHGGGDT (SEQ ID NO: 2), HCDR3: ARHSGYER-GYYYVMDY (SEQ ID NO: 3), LCDR1: ESVDYYGFSF (SEQ ID NO: 4), LCDR2: AAS (SEQ ID NO: 5), LCDR3: QQSKEVPW (SEQ ID NO: 6);
(b) HCDR1: GYTFTSYT (SEQ ID NO: 7), HCDR2: INPTTGYT (SEQ ID NO: 8), HCDR3: ARD-DAYYSGY (SEQ ID NO: 9), LCDR1: ENIYSNL (SEQ ID NO: 10), LCDR2: AAK (SEQ ID NO: 11), LCDR3: QHFWGTPWT (SEQ ID NO: 12); and
(c) HCDR1: GFAFSSYD (SEQ ID NO: 13), HCDR2: ITIGGGTT (SEQ ID NO: 14), HCDR3: ARHRYDYFAMDN (SEQ ID NO: 15), LCDR1: ENVDNYGINF (SEQ ID NO: 16), LCDR2: VSS (SEQ ID NO: 17), LCDR3: QQSKDVPW (SEQ ID NO: 18).

15. The method of claim 1, wherein the antibody or fragment thereof is administered intravenously.

16. The method of claim 1, wherein the method further comprises administering a second therapy.

17. A method of treating a cancer in an individual in need thereof, comprising administering to the individual a composition comprising an effective amount of antibody or fragment thereof that specifically binds to PD-1, and wherein the antibody or fragment thereof is selected from the group comprising:

(a) a HCDR1, a HCDR2, and a HCDR3, respectively comprising the amino acid sequences of a CDR1, a CDR2, and a CDR3 within a VH chain having the sequence set forth SEQ ID NOs: 35, and a LCDR1, a LCDR2, and a LCDR3, respectively comprising the amino acid sequences of a CDR1, a CDR2, and a CDR3 within a VL chain having the sequence set forth in SEQ ID NO: 41;

(b) a HCDR1, a HCDR2, and a HCDR3, respectively comprising the amino acid sequences of a CDR1, a CDR2, and a CDR3 within a VH chain having the sequence set forth in SEQ ID NO: 37, and a LCDR1, a LCDR2, and a LCDR3, respectively comprising the amino acid sequence of a CDR1, a CDR2, and a CDR3 within a VL chain having the sequence set forth in SEQ ID NO: 43;

(c) a HCDR1, a HCDR2, and a HCDR3, respectively comprising the amino acid sequences of a CDR1, a CDR2, and a CDR3 within a VH chain having the sequence set forth in SEQ ID NO: 39, and a LCDR1, a LCDR2, and a LCDR3, respectively comprising the amino acid sequences of a CDR1, a CDR2, and a CDR3 within a VL chain having the sequence set forth in SEQ ID NO: 45.

\* \* \* \* \*

SEQUENCE LISTING

<160> NUMBER OF SEQ ID NOS: 48

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Gly Phe Thr Phe Ser Ser Tyr Thr
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic Construct

<400> SEQUENCE: 2

Ile Ser His Gly Gly Gly Asp Thr
1               5

<210> SEQ ID NO 3
<211> LENGTH: 16
<212> TYPE: PRT
<213> ORGANISM: Artificial Sequence
<220> FEATURE:
<223> OTHER INFORMATION: Synthetic Construct

<400> SEQUENCE: 3

Ala Arg His Ser Gly Tyr Glu Arg Gly Tyr Tyr Tyr Val Met Asp Tyr
1               5                   10                  15

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct

<400> SEQUENCE: 4

Glu Ser Val Asp Tyr Tyr Gly Phe Ser Phe
1               5                   10

<210> SEQ ID NO 5
<211> LENGTH: 3
<212> TYPE: PRT
<213> ORGANISM: Artificial Sequence
<220> FEATURE:
<223> OTHER INFORMATION: Synthetic Construct

<400> SEQUENCE: 5

Ala Ala Ser
1

<210> SEQ ID NO 6
<211> LENGTH: 8
<212> TYPE: PRT
<213> ORGANISM: Artificial Sequence
<220> FEATURE:
<223> OTHER INFORMATION: Synthetic Construct

<400> SEQUENCE: 6

Gln Gln Ser Lys Glu Val Pro Trp
1               5

```
<210> SEQ ID NO 7
<211> LENGTH: 8
<212> TYPE: PRT
<213> ORGANISM: Artificial Sequence
<220> FEATURE:
<223> OTHER INFORMATION: Synthetic Construct

<400> SEQUENCE: 7

Gly Tyr Thr Phe Thr Ser Tyr Thr
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Construct

<400> SEQUENCE: 8

Ile Asn Pro Thr Thr Gly Tyr Thr
1               5

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct

<400> SEQUENCE: 9

Ala Arg Asp Asp Ala Tyr Tyr Ser Gly Tyr
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Synthetic Construct

<400> SEQUENCE: 10

Glu Asn Ile Tyr Ser Asn Leu
1               5

<210> SEQ ID NO 11
<211> LENGTH: 3
<212> TYPE: PRT
<213> ORGANISM: Artificial Sequence
<220> FEATURE:
<223> OTHER INFORMATION: Synthetic Construct

<400> SEQUENCE: 11

Ala Ala Lys
1

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Gln His Phe Trp Gly Thr Pro Trp Thr
1               5
```

```
<210> SEQ ID NO 13
<211> LENGTH: 8
<212> TYPE: PRT
<213> ORGANISM: Artificial Sequence
<220> FEATURE:
<223> OTHER INFORMATION: Synthetic Construct

<400> SEQUENCE: 13

Gly Phe Ala Phe Ser Ser Tyr Asp
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic Construct

<400> SEQUENCE: 14

Ile Thr Ile Gly Gly Gly Thr Thr
1               5

<210> SEQ ID NO 15
<211> LENGTH: 12
<212> TYPE: PRT
<213> ORGANISM: Artificial Sequence
<220> FEATURE:
<223> OTHER INFORMATION: Synthetic Construct

<400> SEQUENCE: 15

Ala Arg His Arg Tyr Asp Tyr Phe Ala Met Asp Asn
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic Construct

<400> SEQUENCE: 16

Glu Asn Val Asp Asn Tyr Gly Ile Asn Phe
1               5                   10

<210> SEQ ID NO 17
<211> LENGTH: 3
<212> TYPE: PRT
<213> ORGANISM: Artificial Sequence
<220> FEATURE:
<223> OTHER INFORMATION: Synthetic Construct

<400> SEQUENCE: 17

Val Ser Ser
1

<210> SEQ ID NO 18
<211> LENGTH: 8
<212> TYPE: PRT
<213> ORGANISM: Artificial Sequence
<220> FEATURE:
<223> OTHER INFORMATION: Synthetic Construct

<400> SEQUENCE: 18

Gln Gln Ser Lys Asp Val Pro Trp
1               5
```

<210> SEQ ID NO 19
<211> LENGTH: 135
<212> TYPE: PRT
<213> ORGANISM: Artificial Sequence
<220> FEATURE:
<223> OTHER INFORMATION: Synthetic Construct

<400> SEQUENCE: 19

```
Ser Gln Val Gln Leu Gln Gln Ser Gly Ala Glu Leu Ala Arg Pro Gly
1               5                   10                  15

Ala Ser Val Lys Met Ser Cys Lys Ala Ser Gly Tyr Thr Phe Thr Ser
            20                  25                  30

Tyr Thr Met His Trp Val Lys Gln Arg Pro Gly Gln Gly Leu Glu Trp
        35                  40                  45

Ile Gly Tyr Ile Asn Pro Thr Thr Gly Tyr Thr Asn Tyr Asn Gln Lys
    50                  55                  60

Phe Lys Asp Lys Ala Asn Pro Thr Thr Gly Tyr Thr Asn Tyr Asn Gln
65                  70                  75                  80

Lys Phe Lys Asp Lys Ala Thr Leu Thr Ala Asp Lys Ser Ser Ser Thr
                85                  90                  95

Ala Tyr Met Gln Leu Ser Ser Leu Thr Ser Glu Asp Ser Ala Val Tyr
            100                 105                 110

Tyr Cys Ala Arg Asp Asp Ala Tyr Tyr Ser Gly Tyr Trp Gly Gln Gly
        115                 120                 125

Thr Thr Leu Thr Val Ser Ser
    130                 135
```

<210> SEQ ID NO 20
<211> LENGTH: 354
<212> TYPE: DNA
<213> ORGANISM: Artificial Sequence
<220> FEATURE:
<223> OTHER INFORMATION: Synthetic Construct

<400> SEQUENCE: 20

```
tcccaggtcc agctgcagca gtctggggct gaactggcaa gacctggggc ctcagtgaag    60
atgtcctgca aggcttctgg ctacaccttt actagttaca cgatgcactg ggtaaaacag   120
aggcctggac agggtctgga atggattgga tacattaatc ctactactgg ttatactaat   180
tacaatcaga agttcaagga caaggccaca ttgactgcag acaaatcctc cagcacagcc   240
tacatgcaat tgagcagcct gacatctgag gactctgcag tctattactg tgcaagagat   300
gatgcttact actcgggcta ctggggccaa ggcaccactc tcacagtctc ctca         354
```

<210> SEQ ID NO 21
<211> LENGTH: 108
<212> TYPE: PRT
<213> ORGANISM: Artificial Sequence
<220> FEATURE:
<223> OTHER INFORMATION: Synthetic Construct

<400> SEQUENCE: 21

```
Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Arg Gln Lys Gln Gly Lys Ser Pro Gln Leu Leu Val
        35                  40                  45

Tyr Ala Ala Lys Asn Leu Ala Asp Gly Val Pro Ser Arg Phe Ser Gly
    50                  55                  60
```

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Trp
                85                  90                  95

Thr Phe Gly Gly Gly Thr Lys Leu Glu Ile Lys Arg
            100                 105

<210> SEQ ID NO 22
<211> LENGTH: 324
<212> TYPE: DNA
<213> ORGANISM: Artificial Sequence
<220> FEATURE:
<223> OTHER INFORMATION: Synthetic Construct

<400> SEQUENCE: 22
gacatccaga tgactcagtc tccagcctcc ctatctgtat ctgtgggaga aactgtcacc    60
atcacatgtc gagcaagtga gaatatttac agtaatttag catggtatcg cagaaacag   120 ggaaaatctc ctcagctcct ggtctatgct gcaaaaaact agcagatgg tgtgccatca   180 aggttcagtg gcagtggatc aggcacacag tattccctca agatcaacag cctgcagtct   240
gaagattttg ggagttatta ctgtcaacat ttttggggta ctccgtggac gttcggtgga   300
ggcaccaagc tggaaatcaa acgg                                          324

<210> SEQ ID NO 23
<211> LENGTH: 140
<212> TYPE: PRT
<213> ORGANISM: Artificial Sequence
<220> FEATURE:
<223> OTHER INFORMATION: Synthetic Construct

<400> SEQUENCE: 23

Val Gln Leu Val Glu Ser Gly Gly Gly Leu Val Lys Pro Gly Gly Ser
1               5                   10                  15

Leu Lys Leu Ser Cys Ala Ala Ser Gly Phe Ala Phe Ser Ser Tyr Asp
                20                  25                  30

Met Ser Trp Val Arg Gln Thr Pro Glu Lys Arg Leu Val Trp Val Ala
            35                  40                  45

Tyr Ile Thr Ile Gly Gly Gly Thr Thr Tyr Tyr Ser Asp Thr Val Lys
        50                  55                  60

Arg Leu Val Trp Val Ala Tyr Ile Thr Ile Gly Gly Thr Thr Tyr
65                  70                  75                  80

Tyr Ser Asp Thr Val Lys Gly Arg Phe Thr Ile Ser Arg Asp Asn Ala
                85                  90                  95

Lys Asn Thr Leu Tyr Leu Gln Met Ser Ser Leu Lys Ser Glu Asp Thr
            100                 105                 110

Ala Met Tyr Tyr Cys Ala Arg His Arg Tyr Asp Tyr Phe Ala Met Asp
        115                 120                 125

Asn Trp Gly His Gly Thr Ser Val Thr Val Ser Ser
    130                 135                 140

<210> SEQ ID NO 24
<211> LENGTH: 357
<212> TYPE: DNA
<213> ORGANISM: Artificial Sequence
<220> FEATURE:
<223> OTHER INFORMATION: Synthetic Construct

<400> SEQUENCE: 24

```
gaagtgcagc tggtggagtc gggggggaggc ttagtgaagc ctggagggtc cctgaaactc    60
tcctgtgcag cctctggatt cgctttcagt agctatgaca tgtcttgggt tcgccagact   120
ccggagaaga ggctggtgtg ggtcgcatac attactattg gtggtggcac cacctactat   180
tcagacactg tgaagggccg attcaccatc tccagagaca tgccaagaa cacccctgtac   240
ctgcaaatga gcagtctgaa gtctgaggac acagccatgt attactgtgc aagacatagg   300
tacgattact cgctatgga caactggggt catggaacct cagtcaccgt ctcctca      357
```

<210> SEQ ID NO 25
<211> LENGTH: 112
<212> TYPE: PRT
<213> ORGANISM: Artificial Sequence
<220> FEATURE:
<223> OTHER INFORMATION: Synthetic Construct

<400> SEQUENCE: 25

```
Asp Ile Val Leu Thr Gln Ser Pro Ala Ser Leu Ala Val Ser Leu Glu
1               5                   10                  15
His Arg Ala Thr Ile Ser Cys Gln Ala Ser Glu Asn Val Asp Asn Tyr
            20                  25                  30
Gly Ile Asn Phe Met Asn Trp Phe Gln His Lys Pro Ala Gln Pro Pro
        35                  40                  45
Gln Leu Leu Ile Tyr Val Ser Ser Asn Leu Gly Ser Gly Val Pro Ala
    50                  55                  60
Lys Phe Ser Gly Ser Gly Ser Gly Thr Asp Phe Ser Leu Asn Ile His
65                  70                  75                  80
Pro Met Glu Glu Asp Asp Thr Ala Met Tyr Phe Cys Gln Gln Ser Lys
                85                  90                  95
Asp Val Pro Trp Thr Phe Ser Gly Gly Thr Lys Leu Glu Ile Lys Arg
            100                 105                 110
```

<210> SEQ ID NO 26
<211> LENGTH: 336
<212> TYPE: DNA
<213> ORGANISM: Artificial Sequence
<220> FEATURE:
<223> OTHER INFORMATION: Synthetic Construct

<400> SEQUENCE: 26

```
gacattgtgc tgacccaatc tccagcttct ttggctgtgt ctctagagca cagggccacc    60
atctcctgcc aagccagcga aaatgttgat aattatggca ttaattttat gaactggttc   120
caacacaaac cagcacagcc acccaactc ctcatctatg tttcatccaa cctaggatcc   180
ggggtccctg ccaagtttag tggcagtggg tctggaacag acttcagcct caacatccat   240
cctatggaag aagatgatac tgcaatgtat ttctgtcagc aaagtaagga cgttccgtgg   300
acgttcagtg gaggcaccaa actggaaatc aaacgg                              336
```

<210> SEQ ID NO 27
<211> LENGTH: 123
<212> TYPE: PRT
<213> ORGANISM: Artificial Sequence
<220> FEATURE:
<223> OTHER INFORMATION: Synthetic Construct -continued

<400> SEQUENCE: 27

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Ile Arg Gln Thr Pro Glu Lys Arg Leu Glu Trp Val
        35                  40                  45

Ala Tyr Ile Ser His Gly Gly Asp Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Ser Gly Tyr Glu Arg Gly Tyr Tyr Tyr Val Met Asp Tyr
            100                 105                 110

Trp Gly Gln Gly Thr Ser Val Thr Val Ser Ser
        115                 120

<210> SEQ ID NO 28
<211> LENGTH: 369
<212> TYPE: DNA
<213> ORGANISM: Artificial Sequence
<220> FEATURE:
<223> OTHER INFORMATION: Synthetic Construct

<400> SEQUENCE: 28
gaagtgaagt tggtggagtc tgggggaggt ttagtgcagc ctggagggtc cctgaaactc      60
tcctgtgcag cctctggatt cactttcagt agctatacca tgtcttggat tcgccagact     120
ccagagaaga ggctggagtg gtcgcatac attagtcatg gtggtggtga cacctactat     180
ccagacactg taaagggccg attcaccatc tccagggaca atgccaagaa caccctgtac     240
ctgcaaatga gcagtctgaa gtctgaggac acggccatgt attactgtgc aagacatagt     300
ggttacgaga ggggatatta ctatgttatg gattactggg gtcaaggaac ctcagtcacc     360
gtctcctca                                                             369

<210> SEQ ID NO 29
<211> LENGTH: 111
<212> TYPE: PRT
<213> ORGANISM: Artificial Sequence
<220> FEATURE:
<223> OTHER INFORMATION: Synthetic Construct

<400> SEQUENCE: 29

Asp Ile Val Leu Thr Gln Phe Pro Thr Ser Leu Ala Val Ser Leu Gly
1               5                   10                  15

Gln Arg Ala Thr Ile Ser Cys Arg Ala Ser Glu Ser Val Asp Tyr Tyr
            20                  25                  30

Gly Phe Ser Phe Ile Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Gly Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
            85                  90                  95

Glu Val Pro Trp Thr Phe Gly Gly Gly Thr Lys Leu Glu Ile Lys
        100                 105                 110

<210> SEQ ID NO 30
<211> LENGTH: 336
<212> TYPE: DNA
<213> ORGANISM: Artificial Sequence
<220> FEATURE:
<223> OTHER INFORMATION: Synthetic Construct

<400> SEQUENCE: 30
gacattgtgc tgacccaatt tccaacttct ttggctgtgt ctctagggca gagggccacc     60
atctcctgca gagccagcga agtgttgat tactatggct ttagttttat aaactggttc    120
caacagaaac caggacagcc acccaaactc ctcatctatg ctgcatccaa ccagggatcc    180
ggggtccctg ccaggtttgg tggcagtggg tctgggacag acttcagcct caacatccat    240
cctatggagg aggatgatac tgcaatgtat ttctgtcagc aaagtaagga ggttccgtgg    300
acgttcggtg gaggcaccaa gctggaaatc aaacgg                              336

<210> SEQ ID NO 31
<211> LENGTH: 450
<212> TYPE: PRT
<213> ORGANISM: Artificial Sequence
<220> FEATURE:
<223> OTHER INFORMATION: Synthetic Construct

<400> SEQUENCE: 31

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Ile Arg Gln Thr Pro Glu Lys Arg Leu Glu Trp Val
        35                  40                  45

Ala Tyr Ile Ser His Gly Gly Gly Asp Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
            85                  90                  95

Ala Arg His Ser Gly Tyr Glu Arg Gly Tyr Tyr Tyr Val Met Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

```
Tyr Gly Pro Pro Cys Pro Cys Pro Ala Pro Glu Phe Leu Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450
```

```
<210> SEQ ID NO 32
<211> LENGTH: 1357
<212> TYPE: DNA
<213> ORGANISM: Artificial Sequence
<220> FEATURE:
<223> OTHER INFORMATION: Synthetic Construct

<400> SEQUENCE: 32
cgaagtgaag ttggtggagt ctgggggagg tttagtgcag cctggagggt ccctgaaact    60
ctcctgtgca gcctctggat tcactttcag tagctatacc atgtcttgga ttcgccagac   120
tccagagaag aggctggagt gggtcgcata cattagtcat ggtggtggtg acacctacta   180
tccagacact gtaaagggcc gattcaccat ctccagggac aatgccaaga acaccctgta   240
cctgcaaatg agcagtctga agtctgagga cacggccatg tattactgtg caagacatag   300
tggttacgag aggggatatt actatgttat ggattactgg ggtcaaggaa cctcagtcac   360
cgtctcctca gctagcacca agggcccag cgtgtttcct ctcgctccct gcagccggag   420
cacatccgag agcaccgctg ctctgggctg tctcgtgaag gactacttcc ctgaacccgt   480
caccgtcagc tggaatagcg cgccctgac atccggcgtc cacacattcc ccgctgtcct   540
gcagagcagc ggcctgtaca gcctgagctc cgtggtcacc gtgcctagca gcagcctggg   600
aacaaagacc tacacctgca acgtggacca taagccctcc aacaccaagg tggacaagcg   660
ggtggaatcc aagtatggac ccccctgtcc tccttgccct gctcctgaat tctcggagg   720
```

```
cccctccgtc ttcctgtttc cccccaagcc caaggacacc ctgatgatct cccggacacc      780
cgaagtcacc tgcgtcgtgg tggatgtcag ccaggaagat cccgaggtgc agttcaactg      840
gtacgtggac ggagtggagg tgcataacgc caaaaccaag cccagggaag agcagttcaa      900
cagcacctat cgggtcgtgt ccgtgctcac cgtcctgcat caggattggc tcaacggcaa      960
ggagtacaag tgcaaggtgt ccaacaaggg cctgccctcc tccatcgaga agaccatctc     1020
caaggctaag ggccaacctc gggagcccca agtgtatacc ctcccctccca gccaggagga    1080 gatgaccaag aatcaagtga gcctgacctg cctcgtgaag ggattttacc cctccgacat     1140
cgctgtggaa tgggaaagca atggccaacc tgagaacaac tacaagacca cccccccgt     1200 gctggactcc gatggctcct tcttcctgta cagcaggctg accgtggaca aatcccggtg     1260
gcaagaggga aacgtgttca gctgctccgt gatgcacgag gctctccaca accactacac     1320
ccagaagagc ctctcccctga gcctcggcaa gtagtaa                             1357
```

<210> SEQ ID NO 33
<211> LENGTH: 219
<212> TYPE: PRT
<213> ORGANISM: Artificial Sequence
<220> FEATURE:
<223> OTHER INFORMATION: Synthetic Construct

<400> SEQUENCE: 33

```
Asp Ile Val Leu Thr Gln Phe Pro Thr Ser Leu Ala Val Ser Leu Gly
1               5                   10                  15

Gln Arg Ala Thr Ile Ser Cys Arg Ala Ser Glu Ser Val Asp Tyr Tyr
            20                  25                  30

Gly Phe Ser Phe Ile Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Gly Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Gln Asp Ser Lys Asp Ser
                165                 170                 175

Thr Tyr Ser Leu Thr Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 34
<211> LENGTH: 661
<212> TYPE: DNA
<213> ORGANISM: Artificial Sequence
<220> FEATURE:
<223> OTHER INFORMATION: Synthetic Construct

<400> SEQUENCE: 34

```
agacattgtg ctgacccaat ttccaacttc tttggctgtg tctctagggc agagggccac      60
catctcctgc agagccagcg aaagtgttga ttactatggc tttagtttta taaactggtt     120
ccaacagaaa ccaggacagc acccaaact cctcatctat gctgcatcca accagggatc     180
cggggtccct gccaggtttg gtggcagtgg gtctgggaca gacttcagcc tcaacatcca     240
tcctatggag gaggatgata ctgcaatgta tttctgtcag caaagtaagg aggttccgtg     300
gacgttcggt ggaggcacca agctggaaat caagcggacc gtggccgccc ccagcgtgtt     360
catcttccct cccagcgacg agcagctgaa gtctggcacc gccagcgtgg tgtgcctgct     420
gaacaacttc tacccccgcg aggccaaggt gcagtggaag gtggacaacg ccctgcagag     480
cggcaacagc caggagagcg tgaccgagca acaggactcc aaggacagca cctacagcct     540
gaccagcacc ctgaccctga gcaaggccga ctacgaaag cacaaggtgt acgcctgcga     600
ggtgacccac cagggactgt ctagccccgt gaccaagagc ttcaaccggg gcgagtgcta     660
a                                                                     661
```

<210> SEQ ID NO 35
<211> LENGTH: 124
<212> TYPE: PRT
<213> ORGANISM: Artificial Sequence
<220> FEATURE:
<223> OTHER INFORMATION: Synthetic Construct

<400> SEQUENCE: 35

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ser Tyr Ile Ser His Gly Gly Gly Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ser Gly Tyr Glu Arg Gly Tyr Tyr Tyr Val Met Asp Tyr
            100                 105                 110

Trp Gly Gln Gly Thr Leu Val Thr Val Ser Ser Ala
        115                 120
```

<210> SEQ ID NO 36
<211> LENGTH: 373
<212> TYPE: DNA
<213> ORGANISM: Artificial Sequence
<220> FEATURE:
<223> OTHER INFORMATION: Synthetic Construct

<400> SEQUENCE: 36

```
cgaagtgcag ctggtggaat ctggcggcgg actggtgcag cctggcggat ctctgagact      60
gtcttgtgcc gcctccggct tcaccttctc cagctacacc atgtcctggg tgcgacaggc     120
tcctggcaag ggcctggaat gggtgtccta catctctcac ggcggaggcg acacctacta     180
```

```
cgccgactct gtgaagggcc ggttcaccat ctcccgggac aactccaaga acaccctgta      240
cctgcagatg aactccctgc gggccgagga caccgccgtg tactactgtg ctcggcactc      300
tggctacgag cggggctact actacgtgat ggactactgg ggccagggca ccctcgtgac      360
cgtgtcatct gct                                                        373
```

```
<210> SEQ ID NO 37
<211> LENGTH: 123
<212> TYPE: PRT
<213> ORGANISM: Artificial Sequence
<220> FEATURE:
<223> OTHER INFORMATION: Synthetic Construct

<400> SEQUENCE: 37
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ser Tyr Ile Ser His Gly Gly Asp Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ser Gly Tyr Glu Arg Gly Tyr Tyr Tyr Val Met Asp Tyr
            100                 105                 110

Trp Gly Gln Gly Thr Leu Val Thr Val Ser Ser
        115                 120

```
<210> SEQ ID NO 38
<211> LENGTH: 373
<212> TYPE: DNA
<213> ORGANISM: Artificial Sequence
<220> FEATURE:
<223> OTHER INFORMATION: Synthetic Construct

<400> SEQUENCE: 38
cgaagtgcag ctggtggaat ctggcggcgg actggtgcag cctggcggat ctctgagact      60
gtcttgtgcc gcctccggct tcaccttctc cagctacacc atgtcctggg tgcgacaggc      120
tcctggcaag ggcctggaat gggtgtccta catctctcac ggcggaggcg acacctacta      180
ccccgactct gtgaagggcc ggttcaccat ctcccgggac aactccaaga acaccctgta      240
cctgcagatg aactccctgc gggccgagga caccgccgtg tactactgtg ctcggcactc      300
tggctacgag cggggctact actacgtgat ggactactgg ggccagggca ccctcgtgac      360
cgtgtcatct gct                                                        373
```

```
<210> SEQ ID NO 39
<211> LENGTH: 146
<212> TYPE: PRT
<213> ORGANISM: Artificial Sequence
<220> FEATURE:
<223> OTHER INFORMATION: Synthetic Construct
```

<400> SEQUENCE: 39

| Glu | Val | Lys | Leu | Leu | Glu | Ser | Gly | Gly | Gly | Leu | Val | Gln | Pro | Gly | Gly |
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |

| Thr | Met | Ser | Trp | Val | Arg | Gln | Ala | Pro | Gly | Lys | Gly | Leu | Glu | Trp | Val |
| | | 35 | | | | | 40 | | | | | 45 | | | |

| Ser | Tyr | Ile | Ser | His | Gly | Gly | Asp | Thr | Tyr | Tyr | Pro | Asp | Ser | Val |
| 50 | | | | | 55 | | | | | 60 | | | | |

| Lys | Gly | Arg | Phe | Thr | Ile | Ser | Arg | Asp | Asn | Ser | Lys | Gly | Gly | Asp | Thr |
| 65 | | | | | 70 | | | | | 75 | | | | | 80 |

| Tyr | Tyr | Pro | Asp | Ser | Val | Lys | Gly | Arg | Phe | Thr | Ile | Ser | Arg | Asp | Asn |
| | | | | 85 | | | | | 90 | | | | | 95 | |

| Ser | Lys | Asn | Thr | Leu | Tyr | Leu | Gln | Met | Asn | Ser | Leu | Arg | Ala | Glu | Asp |
| | | | 100 | | | | | 105 | | | | | 110 | | |

| Thr | Ala | Val | Tyr | Tyr | Cys | Ala | Arg | His | Ser | Gly | Tyr | Glu | Arg | Gly | Tyr |
| | | 115 | | | | | 120 | | | | | 125 | | | |

| Tyr | Tyr | Val | Met | Asp | Tyr | Trp | Gly | Lys | Gly | Thr | Thr | Val | Thr | Val | Ser |
| | 130 | | | | | 135 | | | | | 140 | | | | |

Ser Ala
145

<210> SEQ ID NO 40
<211> LENGTH: 372
<212> TYPE: DNA
<213> ORGANISM: Artificial Sequence
<220> FEATURE:
<223> OTHER INFORMATION: Synthetic Construct

<400> SEQUENCE: 40

```
gaagtgaagc tgctggaatc tggcggcgga ctggtgcagc ctggcggatc tctgagactg      60
tcttgtgccg cctccggctt caccttctcc agctacacca tgtcctgggt gcgacaggct    120
cctggcaagg gcctggaatg ggtgtcctac atctctcacg gcggaggcga cacctactac    180
cccgactctg tgaagggccg gttcaccatc tcccgggaca actccaagaa cacccctgtac   240 ctgcagatga actccctgcg ggccgaggac accgccgtgt actactgtgc tcggcactct    300
ggctacgagc ggggctacta ctacgtgatg gactactggg gcaagggcac caccgtgacc    360
gtgtcatctg ct                                                         372
```

<210> SEQ ID NO 41
<211> LENGTH: 112
<212> TYPE: PRT
<213> ORGANISM: Artificial Sequence
<220> FEATURE:
<223> OTHER INFORMATION: Synthetic Construct

<400> SEQUENCE: 41

| Asp | Ile | Val | Met | Thr | Gln | Ser | Pro | Asp | Ser | Leu | Ala | Val | Ser | Leu | Gly |
| 1 | | | | 5 | | | | | 10 | | | | | 15 | |

| Glu | Arg | Ala | Thr | Ile | Asn | Cys | Lys | Ser | Ser | Glu | Ser | Val | Asp | Tyr | Tyr |
| | | | 20 | | | | | 25 | | | | | 30 | | |

| Gly | Phe | Ser | Phe | Leu | Asn | Trp | Phe | Gln | Gln | Lys | Pro | Gly | Gln | Pro | Pro |
| | | 35 | | | | | 40 | | | | | 45 | | | |

| Lys | Leu | Leu | Ile | Tyr | Ala | Ala | Ser | Asn | Arg | Glu | Ser | Gly | Val | Pro | Asp |
| 50 | | | | | 55 | | | | | 60 | | | | | |

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

<210> SEQ ID NO 42
<211> LENGTH: 337
<212> TYPE: DNA
<213> ORGANISM: Artificial Sequence
<220> FEATURE:
<223> OTHER INFORMATION: Synthetic Construct

<400> SEQUENCE: 42
agacatcgtg atgacccagt cccccgactc cctggctgtg tctctgggcg agagagccac      60
catcaactgc aagtcctccg agtccgtgga ctactacggc ttctccttcc tgaactggtt     120
ccagcagaag cccggccagc ccctaagct gctgatctac gccgcctcca accgcgagtc      180
tggcgtgccc gatagattct ccggctctgg ctctggcacc gactttaccc tgaccatcag     240
ctccctgcag gccgaggatg tggccgtgta ctactgccag cagtccaaag aggtgccctg     300
gaccttcggc cagggcacaa agctggaaat caagcgg                              337

<210> SEQ ID NO 43
<211> LENGTH: 112
<212> TYPE: PRT
<213> ORGANISM: Artificial Sequence
<220> FEATURE:
<223> OTHER INFORMATION: Synthetic Construct

<400> SEQUENCE: 43

Asp Ile Val Met Thr Gln Ser Pro Asp Ser Leu Ala Val Ser Leu Gly
1               5                   10                  15

Glu Arg Ala Thr Ile Asn Cys Lys Ala Ser Glu Ser Val Asp Tyr Tyr
                20                  25                  30

Gly Phe Ser Phe Leu Asn Trp Phe Gln Gln Lys Pro Gly Gln Pro Pro
            35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

<210> SEQ ID NO 44
<211> LENGTH: 337
<212> TYPE: DNA
<213> ORGANISM: Artificial Sequence
<220> FEATURE:
<223> OTHER INFORMATION: Synthetic Construct

<400> SEQUENCE: 44
agacatcgtg atgacccagt cccccgactc cctggctgtg tctctgggcg agagagccac      60
catcaactgc aaggcctccg agtccgtgga ctactacggc ttctccttcc tgaactggtt     120
ccagcagaag cccggccagc ccctaagct gctgatctac gccgcctcca accgcgagtc      180
tggcgtgccc gatagattct ccggctctgg ctctggcacc gactttaccc tgaccatcag     240
ctccctgcag gccgaggatg tggccgtgta ctactgccag cagtccaaag aggtgccctg    300
gaccttcggc cagggcacaa agctggaaat caagcgg    337

<210> SEQ ID NO 45
<211> LENGTH: 112
<212> TYPE: PRT
<213> ORGANISM: Artificial Sequence
<220> FEATURE:
<223> OTHER INFORMATION: Synthetic Construct

<400> SEQUENCE: 45

Asp Ile Gln Leu Thr Gln Ser Pro Asp Ser Leu Ser Val Ser Leu Gly
1               5                   10                  15

Glu Arg Ala Thr Ile Asn Cys Lys Ala Ser Glu Ser Val Asp Tyr Tyr
            20                  25                  30

Gly Phe Ser Phe Leu Asn Trp Phe Gln Gln Lys Pro Gly Gln Pro Pro
        35                  40                  45

Lys Leu Leu Ile Tyr Ala Ala Ser Asn Arg Gln Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Phe Cys Gln Gln Ser Lys
                85                  90                  95

Glu Val Pro Trp Thr Phe Gly Gln Gly Thr Lys Leu Glu Ile Lys Arg
            100                 105                 110

<210> SEQ ID NO 46
<211> LENGTH: 336
<212> TYPE: DNA
<213> ORGANISM: Artificial Sequence
<220> FEATURE:
<223> OTHER INFORMATION: Synthetic Construct

<400> SEQUENCE: 46
gacatccagc tgacccagtc ccccgactcc ctgtctgtgt ctctgggcga gagagccacc    60
atcaactgca aggcctccga gtccgtggac tactacggct ctccttcct gaactggttc    120 cagcagaagc ccggccagcc ccctaagctg ctgatctacg ccgcctccaa ccgccagtct    180
ggcgtgcccg atagattctc cggctctggc tctggcaccg actttaccct gaccatcagc    240
tccctgcagg ccgaggatgt ggccgtgtac ttctgccagc agtccaaaga ggtgccctgg    300
accttcggcc agggcacaaa gctggaaatc aagcgg    336

<210> SEQ ID NO 47
<211> LENGTH: 29
<212> TYPE: DNA
<213> ORGANISM: Artificial Sequence
<220> FEATURE:
<223> OTHER INFORMATION: Synthetic Construct

<400> SEQUENCE: 47
ctgtctagaa tgcagatccc acaggcgcc    29

<210> SEQ ID NO 48
<211> LENGTH: 26
<212> TYPE: DNA
<213> ORGANISM: Artificial Sequence
<220> FEATURE:
<223> OTHER INFORMATION: Synthetic Construct

```
<400> SEQUENCE: 48
ggatcctcag aggggccaag agcagt                                              26
```